(12) United States Patent
Han et al.

(10) Patent No.: US 9,637,485 B2
(45) Date of Patent: May 2, 2017

(54) 6,7-DIHYDROBENZO[A]QUINOLIZIN-2-ONE DERIVATIVES FOR THE TREATMENT AND PROPHYLAXIS OF HEPATITIS B VIRUS INFECTION

(71) Applicant: Hoffmann-La Roche Inc., Little Falls, NJ (US)

(72) Inventors: Xingchun Han, Shanghai (CN); Min Jiang, Shanghai (CN); Jianhua Wang, Shanghai (CN); Chengang Zhou, Shanghai (CN); Yongguang Wang, Shanghai (CN); Song Yang, Shanghai (CN)

(73) Assignee: Hoffmann-LA Roche Inc., Little Falls, NJ (US)

( * ) Notice: Subject to any disclaimer, the term of this patent is extended or adjusted under 35 U.S.C. 154(b) by 0 days.

(21) Appl. No.: 14/926,393

(22) Filed: Oct. 29, 2015

(65) Prior Publication Data

US 2016/0122344 A1 May 5, 2016

(30) Foreign Application Priority Data

Nov. 3, 2014 (WO) ................ PCT/CN2014/090156
Jul. 14, 2015 (WO) ................ PCT/CN2015/083939

(51) Int. Cl.
*A61K 31/4985* (2006.01)
*C07D 471/04* (2006.01)

(52) U.S. Cl.
CPC ................. *C07D 471/04* (2013.01)

(58) Field of Classification Search
USPC ................. 514/233.2, 253.03, 294
See application file for complete search history.

(56) References Cited

U.S. PATENT DOCUMENTS 3,983,122 A * 9/1976 Lundberg ............. C07D 471/04
546/150

FOREIGN PATENT DOCUMENTS

| CA | 2093107 A1 | 10/1993 |
| WO | 2015/113990 | 8/2015 |
| WO | 2015/173164 | 11/2015 |

OTHER PUBLICATIONS

Fecik (Journal of Medicinal Chemistry; 2005, 48, 4, 1229-1236).*
Chu (Journal of Medicinal Chemistry; 1985, 28, 11, 1558-1564).*
Acs et al., Proc Natl Acad Sci USA 84:4641-4644 ( 1987).
Ansel et al., "Pharmaceutical Dosage Forms and Drug Delivery Systems" 6th Ed.:456-457 (1995).
Bastin et al., "Salt Selection and Optimisation Procedures for Pharmaceutical New Chemical Entities" Organic Process Research & Development 4:427-435 ( 2000).
Belloni et al., "IFN-α inhibits HBV transcription and replication in cell culture and in humanized mice by targeting the epigenetic regulation of the nuclear cccDNa minichromosome" J Clin Invest 122(2):529-537 (Feb. 2012).
Buster et al., "Peginterferon alpha-2b is safe and effective in HBeAg-Positive chronic hepatitis B patients with advanced fibrosis" Hepatology 46:388-394 ( 2007).
CAS Registry Database, XP002736278, Jun. 9, 2008.
Fecik et al., "Chiral DNA gyrase inhibitors. 3. Probing the chiral preference of the active site of DNA gyrase. Synthesis of 10-fluoro-6-methyl-6,7-dihydro-9-piperazinyl-2H-benzo[a]quinolizin-20-one-3-carboxylic acid analogues" J Med Chem 48:1229-1236 ( 2005).
Fisicaro et al., "Antiviral intrahepatic T-cell responses can be restored by blocking programmed death-1 pathway in chronic hepatits B" Gastroenterology 138:682-693 ( 2010).
Geng Ca et al., "Small-molecule inhibitors for the treatment of hepatitis B virus documented in patents" Mini Reviews in Medicinal Chemistry 13(5):749-776 (Apr. 1, 2013).
Janssen et al., "Pegylated interferon alfa-2b alone or in combination with lamivudine for HBeAg-positive chronic hepatitis B: a randomised trial" LANCET 365:123-129 (Jan. 8, 2005).
Kondo et al., "Hepatitis B surface antigen could contribute to the immunopathogenesis of hepatitis B virus infection" ISRN Gastroenterology (Article ID 935295), 2013.
Kondo et al., "Recovery of functional cytotoxic T lymphocytes during lamivudine therapy by acquiring multi-specificity" J Med Virol 74:425-433 ( 2004).
Kumar et al., "Hepatitis B virus regulatory HBx protein binds to adaptor protein IPS-1 and inhibits the activation of beta interferon" J Virol 85(2):987-995 (Jan. 2011).
Lambert et al., "Posttranslational N-glycosylation of the hepatitis B virus large envelope protein" Virol J 4( Suppl 1-9):45 (May 2007).
Locarnini, S., "Molecular virology and the development of resistant mutants: implications for therapy" Semin Liver Dis 25( Suppl 1):9-19 ( 2005).
Mao et al., "Indoleamine 2,3-dioxygenase mediates the antiviral effect of gagamma interferon against hepatitis B virus in human hepatocyte-derived cells"J Virol 85(2):1048-1057 (Jan. 2011).
Mao et al., "Inhibition of hepatitis B virus replication by the host zinc finger antiviral protein" PLoS Pathogens 9(7 Suppl 1-18):e1003494 (Jul. 2013).
Marcellin et al., "Peginterferon alfa-2a alone, lamivudine alone, and the two in combination in patients with HBeAg-negative chronic hepatitis B" New E J Med 351(12):1206-1217 (Sep. 16, 2004).
Nayersina et al., "HLA A2 restricted cytotoxic T lymphocyte responses to multiple hepatitis B surface antigen epitopes during hepatitis B virus infection" J Immunol 150:4659-4671 (May 15, 1993).

(Continued)

*Primary Examiner* — Pancham Bakshi
(74) *Attorney, Agent, or Firm* — Jonathan Duffield

(57) ABSTRACT

The invention provides novel compounds having the general formula:

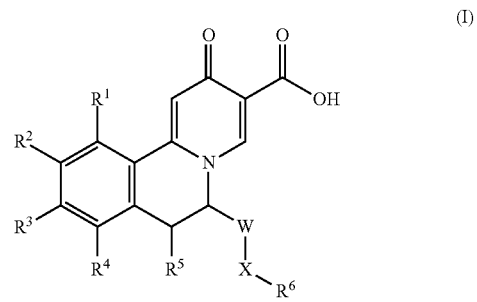

wherein $R^1$ to $R^6$, W and X are as described herein and their pharmaceutically acceptable salt, enantiomer or diastereomer thereof, and compositions including the compounds and methods of using the compounds.

25 Claims, No Drawings

(56) References Cited

OTHER PUBLICATIONS

Op den Brouw et al., "Hepatitis B virus surface antigen impairs myeloid dendritic cell function: a possible immune escape mechanism of hepatitis B virus" Immunol 216:280-290 ( 2008).

Quasdorff et al., "Control of hepatitis B virus at the level of transcription" J Viral Hepatitis 17:527-536 ( 2010).

Schulze et al., "Hepatitis B virus infection initiates with a large surface protein-dependent binding to heparan sulfate proteoglycans" Hepatology 46:1759-1768 ( 2007).

Shi et al., "Hepatitis B virus suppresses the functional interaction between natural killer cells and plasmacytoid dendritic cells" J Viral Hepatitis 19:e26-e33 ( 2012).

Wieland et al., "Stealth and cunning: hepatitis B and hepatitis C viruses" J Virol 79(15):9369-9380 (Aug. 2005).

Woltman et al., "Hepatitis B virus lacks immune activating capacity, but actively inhibits plasmacytoid dendritic cell function" PLoS ONE 6(1 Suppl 1-14):e15324 (Jan. 2011).

Yan et al., "Molecular determinants of hepatitis B and D virus entry restriction in mouse sodium taurocholate cotransporting polypeptide" J Virol 87(14):7977-7991 (Jul. 2013).

\* cited by examiner

6,7-DIHYDROBENZO[A]QUINOLIZIN-2-ONE DERIVATIVES FOR THE TREATMENT AND PROPHYLAXIS OF HEPATITIS B VIRUS INFECTION

This application claims the benefit under 35 U.S.C. 119(a) to International Application No. PCT/CN2015/083939, filed Jul. 14, 2015, and claims the benefit under 35 U.S.C. §119 to International Application No. PCT/CN2014/090156, filed Nov. 3, 2014, the entire contents of both are incorporated herein by reference.

The present invention relates to organic compounds useful for therapy and/or prophylaxis in a mammal, and in particular to HBsAg (HBV Surface antigen) inhibitors useful for treating HBV infection.

FIELD OF THE INVENTION

The present invention relates to novel 6,7-dihydrobenzo[a]quinolizin-2-one derivatives having pharmaceutical activity, their manufacture, pharmaceutical compositions containing them and their potential use as medicaments.

The present invention relates to compounds of formula (I)

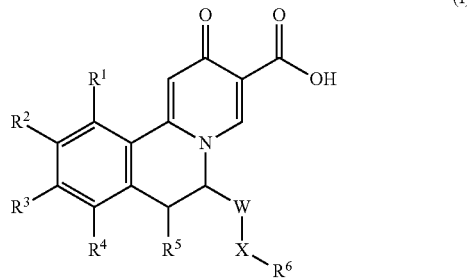

(I)

wherein $R^1$ to $R^6$, W and X are as described below, or to pharmaceutically acceptable salts, or to enantiomers thereof.

The hepatitis B virus (HBV) is an enveloped, partially double-stranded DNA virus. The compact 3.2 kb HBV genome consists of four overlapping open reading frames (ORF), which encode for the core, polymerase (Pol), envelope and X-proteins. The Pol ORF is the longest and the envelope ORF is located within it, while the X and core ORFs overlap with the Pol ORF. The lifecycle of HBV has two main events: 1) generation of closed circular DNA (cccDNA) from relaxed circular (RC DNA), and 2) reverse transcription of pregenomic RNA (pgRNA) to produce RC DNA. Prior to the infection of host cells, the HBV genome exists within the virion as RC DNA. It has been determined that HBV virions are able to gain entry into host cells by non-specifically binding to the negatively charged proteoglycans present on the surface of human hepatocytes (Schulze, A., P. Gripon & S. Urban. *Hepatology*, 46, (2007), 1759-68) and via the specific binding of HBV surface antigens (HBsAg) to the hepatocyte sodium-taurocholate cotransporting polypeptide (NTCP) receptor (Yan, H. et al. *J Virol*, 87, (2013), 7977-91). Once the virion has entered the cell, the viral cores and the encapsidated RC DNA are transported by host factors, via a nuclear localization signal, into the nucleus through the Impβ/Impα nuclear transport receptors. Inside the nucleus, host DNA repair enzymes convert the RC DNA into cccDNA. cccDNA acts as the template for all viral mRNAs and as such, is responsible for HBV persistence in infected individuals. The transcripts produced from cccDNA are grouped into two categories; Pregenomic RNA (pgRNA) and subgenomic RNA. Subgenomic transcripts encode for the three envelopes (L, M and S) and X proteins, and pgRNA encodes for Pre-Core, Core, and Pol proteins (Quasdorff, M. & U. Protzer. *J Viral Hepat*, 17, (2010), 527-36) Inhibition of HBV gene expression or HBV RNA synthesis leads to the inhibition of HBV viral replication and antigens production (Mao, R. et al. *PLoS Pathog*, 9, (2013), e1003494; Mao, R. et al. *J Virol*, 85, (2011), 1048-57). For instance, IFN-α was shown to inhibit HBV replication and viral HBsAg production by decreasing the transcription of pgRNA and subgenomic RNA from the HBV covalently closed circular DNA (cccDNA) minichromosome. (Belloni, L. et al. *J Clin Invest*, 122, (2012), 529-37; Mao, R. et al. *J Virol*, 85, (2011), 1048-57). All HBV viral mRNAs are capped and polyadenylated, and then exported to the cytoplasm for translation. In the cytoplasm, the assembly of new virons is initiated and nascent pgRNA is packaged with viral Pol so that reverse transcription of pgRNA, via a single stranded DNA intermediate, into RC DNA can commence. The mature nucleocapsids containing RC DNA are enveloped with cellular lipids and viral L, M, and S proteins and then the infectious HBV particles are then released by budding at the intracellular membrane (Locarnini, S. *Semin Liver Dis*, (2005), 25 Suppl 1, 9-19). Interestingly, non-infectious particles are also produced that greatly outnumber the infectious virions. These empty, enveloped particles (L, M and S) are referred to as subviral particles. Importantly, since subviral particles share the same envelope proteins and as infectious particles, it has been surmised that they act as decoys to the host immune system and have been used for HBV vaccines. The S, M, and L envelope proteins are expressed from a single ORF that contains three different start codons. All three proteins share a 226aa sequence, the S-domain, at their C-termini. M and L have additional pre-S domains, Pre-S2 and Pre-S2 and Pre-S1, respectively. However, it is the S-domain that has the HBsAg epitope (Lambert, C. & R. Prange. *Virol J*, (2007), 4, 45).

The control of viral infection needs a tight surveillance of the host innate immune system which could respond within minutes to hours after infection to impact on the initial growth of the virus and limit the development of a chronic and persistent infection. Despite the available current treatments based on IFN and nucleos(t)ide analogues, the Hepatitis B virus (HBV) infection remains a major health problem worldwide which concerns an estimated 350 million chronic carriers who have a higher risk of liver cirrhosis and hepatocellular carcinoma.

The secretion of antiviral cytokines in response to HBV infection by the hepatocytes and/or the intra-hepatic immune cells plays a central role in the viral clearance of infected liver. However, chronically infected patients only display a weak immune response due to various escape strategies adopted by the virus to counteract the host cell recognition systems and the subsequent antiviral responses.

Many observations showed that several HBV viral proteins could counteract the initial host cellular response by interfering with the viral recognition signaling system and subsequently the interferon (IFN) antiviral activity. Among these, the excessive secretion of HBV empty subviral particles (SVPs, HBsAg) may participate to the maintenance of the immunological tolerant state observed in chronically infected patients (CHB). The persistent exposure to HBsAg and other viral antigens can lead to HBV-specific T-cell deletion or to progressive functional impairment (Kondo et al. *Journal of Immunology* (1993), 150, 4659-4671; Kondo et al. *Journal of Medical Virology* (2004), 74, 425-433; Fisicaro et al. *Gastroenterology*, (2010), 138, 682-93). Moreover HBsAg has been reported to suppress the function of immune cells such as monocytes, dendritic cells (DCs) and natural killer (NK) cells by direct interaction (Op den Brouw et al. *Immunology*, (2009b), 126, 280-9; Woltman et al. *PLoS One*, (2011), 6, e15324; Shi et al. *J Viral Hepat*. (2012), 19, e26-33; Kondo et al. *ISRN Gasteroenterology*, (2013), Article ID 935295).

HBsAg quantification is a significant biomarker for prognosis and treatment response in chronic hepatitis B. However the achievement of HBsAg loss and seroconversion is rarely observed in chronically infected patients but remains the ultimate goal of therapy. Current therapy such as Nucleos(t)ide analogues are molecules that inhibit HBV DNA synthesis but are not directed at reducing HBsAg level. Nucleos(t)ide analogs, even with prolonged therapy, have demonstrated rates of HBsAg clearance comparable to those observed naturally (between −1%-2%) (Janssen et al. *Lancet*, (2005), 365, 123-9; Marcellin et al. *N. Engl. J. Med.*, (2004), 351, 1206-17; Buster et al. *Hepatology*, (2007), 46, 388-94). Therefore, targeting HBsAg together with HBV DNA levels in CHB patients may significantly improve CHB patient immune reactivation and remission (Wieland, S. F. & F. V. Chisari. *J Virol*, (2005), 79, 9369-80; Kumar et al. *J Virol*, (2011), 85, 987-95; Woltman et al. *PLoS One*, (2011), 6, e15324; Op den Brouw et al. *Immunology*, (2009b), 126, 280-9).

SUMMARY OF THE INVENTION

The present invention relates to novel compounds of formula (I)

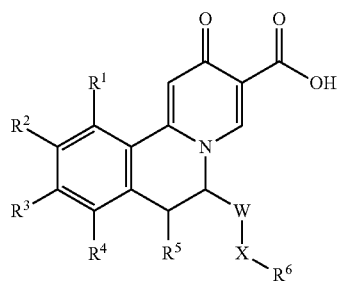

(I)

wherein
$R^1$, $R^2$, $R^3$ and $R^4$ are independently selected from hydrogen, halogen, $C_{1-6}$alkyl, di$C_{1-6}$alkylamino, cyano, N-containing monocyclic heterocycloalkyl and $OR^7$, wherein
  $R^7$ is hydrogen; $C_{1-6}$alkyl; or $C_{1-6}$alkyl which is substituted once or more times by fluoro, $C_{3-7}$cycloalkyl, phenyl, hydroxyl, amino, $C_{1-6}$alkoxy, $C_{1-6}$alkylsulfanyl, $C_{1-6}$alkylsulfonyl, di$C_{1-6}$alkylamino, $C_{1-6}$alkoxycarbonylamino, monocyclic heterocycloalkyl, pyrazoyl or imidazolyl;
$R^5$ is hydrogen or $C_{1-6}$alky;
$R^6$ is hydrogen, $C_{1-6}$alkyl, phenyl-$C_xH_{2x}$—, $C_{1-6}$alkylcarbonyl, $C_{1-6}$alkylsulfonyl, benzoyl or monocyclic heterocycloalkyl, wherein
  x is 1-6;
W is a bond, $C_yH_{2y}$, $C(R^8)(R^9)C_zH_{2z}$ or $C_yH_{2y}CH(R^8)CH(R^9)C_zH_{2z}$, wherein
  $R^8$ and $R^9$ are independently selected from hydrogen, fluoro, hydroxy and $C_{1-6}$alkyl,
  y is 0-6;
  z is 0-6;

X is a bond; O; S; $S(O)_2$; or $NR^{10}$, wherein $R^{10}$ is hydrogen, $C_{1-6}$alkyl;
or $R^6$ and $R^{10}$, together with the nitrogen to which they are attached, form monocyclic heterocycloalkyl;
with the proviso that when X is a bond, $R^6$ is not hydrogen, $C_{1-6}$alkyl or phenyl-$C_xH_{2x}$—;
or pharmaceutically acceptable salts, enantiomers or diastereomers thereof.

The invention also relates to their manufacture, medicaments based on a compound in accordance with the invention and their production as well as the use of compounds of formula (I) as HBsAg inhibitors. Accordingly, the compounds of formula (I) are useful for the treatment or prophylaxis of HBV infection.

DETAILED DESCRIPTION OF THE INVENTION

Unless otherwise defined, all technical and scientific terms used herein have the same meaning as commonly understood by one of ordinary skill in the art to which this invention belongs. Furthermore, the following definitions are set forth to illustrate and define the meaning and scope of the various terms used to describe the invention.

DEFINITIONS

As used herein, the term "$C_{1-6}$alkyl" alone or in combination signifies a saturated, linear- or branched chain alkyl group containing 1 to 6, particularly 1 to 4 carbon atoms, for example methyl, ethyl, propyl, isopropyl, 1-butyl, 2-butyl, tert-butyl and the like. Particular "$C_{1-6}$alkyl" groups are methyl, ethyl, isopropyl and tert-butyl.

The term "$C_xH_{2x}$" alone or in combination signifies a saturated, linear- or branched chain alkyl group containing 1 to 6, particularly 1 to 4 carbon atoms.

The term "$C_{1-6}$alkoxy" alone or in combination signifies a group $C_{1-6}$alkyl-O—, wherein the "$C_{1-6}$alkyl" is as defined above; for example methoxy, ethoxy, propoxy, iso-propoxy, n-butoxy, iso-butoxy, 2-butoxy, tert-butoxy and the like. Particular "$C_{1-6}$alkoxy" groups are methoxy and ethoxy and more particularly methoxy.

The term "$C_{3-7}$cycloalkyl", alone or in combination, refers to a saturated carbon ring containing from 3 to 7 carbon atoms, particularly from 3 to 6 carbon atoms, for example, cyclopropyl, cyclobutyl, cyclopentyl, cyclohexyl, cycloheptyl and the like. Particular "$C_{3-7}$cycloalkyl" groups are cyclopropyl, cyclopentyl and cyclohexyl.

The term "monocyclic heterocycloalkyl" refers to a monocyclic ring system of 4 to 7 ring atoms, comprising 1, 2, or 3 ring heteroatoms selected from N, O and S, the remaining ring atoms being carbon. Examples for monocyclic heterocycloalkyl are aziridinyl, oxiranyl, azetidinyl, oxetanyl, pyrrolidinyl, tetrahydrofuranyl, tetrahydro-thienyl, pyrazolidinyl, imidazolidinyl, oxazolidinyl, isoxazolidinyl, thiazolidinyl, piperidinyl, tetrahydropyranyl, tetrahydrothiopyranyl, piperazinyl, morpholinyl, thiomorpholinyl, 1,1-dioxo-thiomorpholin-4-yl, azepanyl, diazepanyl, homopiperazinyl, or oxazepanyl. Particular "monocyclic heterocycloalkyl" groups are pyrrolidinyl, 2-oxo-pyrrolidinyl and tetrahydropyranyl, and more particularly pyrrolidin-1-yl, 2-oxo-pyrrolidin-1-yl and tetrahydropyran-4-yl.

The term "N-containing monocyclic heterocycloalkyl" refers to a monocyclic heterocycloalkyl wherein at least one of the heteroatoms is N. Examples for N-containing monocyclic heterocycloalkyl are azetidinyl, pyrrolidinyl, pyrazolidinyl, imidazolidinyl, oxazolidinyl, isoxazolidinyl, thiazolidinyl, piperidinyl, piperazinyl, morpholinyl, azepanyl, diazepanyl, homopiperazinyl or oxazepanyl. Particular "N-containing monocyclic heterocycloalkyl" groups are pyrrolidinyl, 2-oxo-pyrrolidinyl, piperidinyl, piperazinyl, and morpholinyl, and more particularly pyrrolidin-1-yl and 2-oxo-pyrrolidin-1-yl.

The term "amino", alone or in combination, refers to primary (—NH$_2$), secondary (—NH—) or tertiary amino

The term "halogen" means fluorine, chlorine, bromine or iodine. Halogen is particularly fluorine or chlorine.

The term "hydroxy" alone or in combination refers to the group OH.

The term "sulfonyl" alone or in combination refers to the group SO$_2$.

The term "C$_{1-6}$alkylcarbonyl" refers to a group C$_{1-6}$alkyl-C(O)—, wherein the "C$_{1-6}$alkyl" is as defined above.

The term "C$_{1-6}$alkylsulfanyl" refers to a group C$_{1-6}$alkyl-S—, wherein the "C$_{1-6}$alkyl" is as defined above.

The term "C$_{1-6}$alkylsulfonyl" refers to a group C$_{1-6}$alkyl-S(O)$_2$—, wherein the "C$_{1-6}$alkyl" is as defined above.

The term "enantiomer" denotes two stereoisomers of a compound which are non-superimposable mirror images of one another.

The compounds according to the present invention may exist in the form of their pharmaceutically acceptable salts. The term "pharmaceutically acceptable salt" refers to conventional acid-addition salts or base-addition salts that retain the biological effectiveness and properties of the compounds of formula (I) and are formed from suitable non-toxic organic or inorganic acids or organic or inorganic bases. Acid-addition salts include for example those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, and the like. Base-addition salts include those derived from ammonium, potassium, sodium and, quaternary ammonium hydroxides, such as for example, tetramethyl ammonium hydroxide. The chemical modification of a pharmaceutical compound into a salt is a technique well known to pharmaceutical chemists in order to obtain improved physical and chemical stability, hygroscopicity, flowability and solubility of compounds. It is for example described in Bastin R. J., et al., Organic Process Research & Development 2000, 4, 427-435; or in Ansel, H., et al., In: Pharmaceutical Dosage Forms and Drug Delivery Systems, 6th ed. (1995), pp. 196 and 1456-1457. Particular are the sodium salts of the compounds of formula (I).

The term "therapeutically effective amount" denotes an amount of a compound or molecule of the present invention that, when administered to a subject, (i) treats or prevents the particular disease, condition or disorder, (ii) attenuates, ameliorates or eliminates one or more symptoms of the particular disease, condition, or disorder, or (iii) prevents or delays the onset of one or more symptoms of the particular disease, condition or disorder described herein. The therapeutically effective amount will vary depending on the compound, the disease state being treated, the severity of the disease treated, the age and relative health of the subject, the route and form of administration, the judgement of the attending medical or veterinary practitioner, and other factors.

The term "pharmaceutical composition" denotes a mixture or solution comprising a therapeutically effective amount of an active pharmaceutical ingredient together with pharmaceutically acceptable excipients to be administered to a mammal, e.g., a human in need thereof.

Compounds of the general formula (I) which contain one or several chiral centers can either be present as racemates, diastereomeric mixtures, or optically active single isomers. The racemates can be separated according to known methods into the enantiomers. Particularly, diastereomeric salts which can be separated by crystallization are formed from the racemic mixtures by reaction with an optically active acid such as e.g. D- or L-tartaric acid, mandelic acid, malic acid, lactic acid or camphorsulfonic acid.

Inhibitors of HBsAg

The present invention relates to (i) a compound of formula (I):

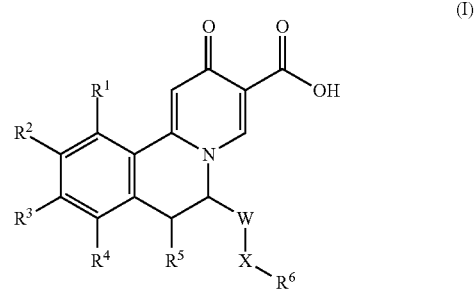

wherein
R$^1$, R$^2$, R$^3$ and R$^4$ are independently selected from hydrogen, halogen, C$_{1-6}$alkyl, diC$_{1-6}$alkylamino, cyano, N-containing monocyclic heterocycloalkyl and OR$^7$, wherein
R$^7$ is hydrogen; C$_{1-6}$alkyl; or C$_{1-6}$alkyl which is substituted once or more times by fluoro, C$_{3-7}$cycloalkyl, phenyl, hydroxyl, amino, C$_{1-6}$alkoxy, C$_{1-6}$alkylsulfanyl, C$_{1-6}$alkylsulfonyl, diC$_{1-6}$alkylamino, C$_{1-6}$alkoxycarbonylamino, monocyclic heterocycloalkyl, pyrazoyl or imidazolyl;
R$^5$ is hydrogen or C$_{1-6}$alky;
R$^6$ is hydrogen, C$_{1-6}$alkyl, phenyl-C$_x$H$_{2x}$—, C$_{1-6}$alkylcarbonyl, C$_{1-6}$alkylsulfonyl, benzoyl or monocyclic heterocycloalkyl, wherein
x is 1-6;
W is a bond, C$_y$H$_{2y}$C(R$^8$)(R$^9$)C$_z$H$_{2z}$ or C$_y$H$_{2y}$CH(R$^8$)CH(R$^9$)C$_z$H$_{2z}$, wherein
R$^8$ and R$^9$ are independently selected from hydrogen, fluoro, hydroxy and C$_{1-6}$alkyl,
y is 0-6;
z is 0-6;
X is a bond; O; S; S(O)$_2$; or NR$^{10}$, wherein R$^{10}$ is hydrogen, C$_{1-6}$alkyl;
or R$^6$ and R$^{10}$, together with the nitrogen to which they are attached, form monocyclic heterocycloalkyl;
with the proviso that when X is a bond, R$^6$ is not hydrogen, C$_{1-6}$alkyl or phenyl-C$_x$H$_{2x}$—;
or pharmaceutically acceptable salts, or enantiomers thereof.

Another embodiment of present invention is (ii) a compound of formula (I) wherein R$^1$, R$^2$, R$^3$ and R$^4$ are independently selected from hydrogen, fluoro, chloro, methyl, ethyl, methoxy, ethoxy, benzyloxy, trifluoromethylmethoxy, methoxyethoxy, methoxypropoxy, ethoxyethoxy, cyclopropylmethoxy, hydroxypropoxy, hydroxydimethylpropoxy, hydoxyhexoxy, (methylpyrrolidinyl)ethoxy, aminohexoxy, dimethylamino-propoxy, (tert-butoxycarbonylamino) hexoxy, methylsulfanylpropoxy, methylsulfonylpropoxy, pyrrolidinylpropoxy, (2-oxo-pyrrolidinyl)propoxy, pyrazoylpropoxy, imidazolylpropoxy, morpholinyl-propoxy, dimethylamino, cyano or pyrrolidinyl;

$R^5$ is hydrogen;

$R^6$ is hydrogen, methyl, benzyl, acetyl, methylsulfonyl, benzoyl, pyrrolidin-1-yl, 2-oxo-pyrrolidinyl or tetrahydropyranyl;

W is a bond, $CH_2$, $C(CH_3)_2$ or $C(CH_3)_2CH_2$;

X is a bond; O; S; $S(O)_2$; or $NR^{10}$, wherein $R^{10}$ is hydrogen, methyl;

or $R^6$ and $R^{10}$, together with the nitrogen to which they are attached, form pyrrolidinyl or 2-oxo-pyrrolidinyl;

or pharmaceutically acceptable salts, enantiomers or diastereomers thereof.

Another embodiment of present invention is (iii) a compound of formula (I), wherein $R^1$ is hydrogen;

$R^2$ is halogen or $C_{1-6}$alkoxy;

$R^3$ is cyano, $C_{1-6}$alkyl, pyrrolidinyl or $OR^7$, wherein
  $R^7$ is $C_{1-6}$alkyl; or $C_{1-6}$alkyl which is substituted once or more times by fluoro, hydroxy, amino, $C_{3-7}$cycloalkyl, phenyl, $C_{1-6}$alkoxy, $C_{1-6}$alkylsulfanyl, $C_{1-6}$alkylsulfonyl, morpholinyl, 2-oxo-pyrrolidinyl, pyrrolidinyl, $diC_{1-6}$alkylamino, $C_{1-6}$alkoxycarbonylamino, pyrazoyl or $C_{1-6}$alkylpyrrolidinyl;

$R^4$ is hydrogen;

$R^5$ is hydrogen;

$R^6$ is hydrogen, $C_{1-6}$alkyl, phenyl-$C_xH_{2x}$, $C_{1-6}$alkylcarbonyl, $C_{1-6}$alkylsulfonyl, benzoyl or tetrahydropyranyl, wherein
  x is 1-6;

W is $C(R^8)(R^9)C_zH_{2z}$, wherein
  $R^8$ and $R^9$ are independently selected from hydrogen and $C_{1-6}$alkyl,
  z is 0-6;

X is a bond; O; S; $S(O)_2$; or $NR^{10}$, wherein $R^{10}$ is hydrogen, $C_{1-6}$alkyl;

or $R^6$ and $R^{10}$, together with the nitrogen to which they are attached, form pyrrolidinyl or 2-oxo-pyrrolidinyl;

or pharmaceutically acceptable salts, enantiomers or diastereomers thereof.

A further embodiment of present invention is (iv) a compound of formula (I), wherein $R^1$ is hydrogen;

$R^2$ is chloro, methoxy or ethoxy;

$R^3$ is cyano, ethyl, pyrrolidinyl, methoxy, ethoxy, benzyloxy, trifluoromethylmethoxy, methoxyethoxy, methoxypropoxy, ethoxyethoxy, cyclopropylmethoxy, hydroxypropoxy, hydroxy-dimethylpropoxy, hydoxyhexoxy, (methylpyrrolidinyl)ethoxy, aminohexoxy, dimethylaminopropoxy, morpholinylpropoxy, pyrrolidinylpropoxy, (2-oxo-pyrrolidinyl)propoxy, (tert-butoxycarbonylamino) hexoxy, methylsulfanylpropoxy, methylsulfonylpropoxy or pyrazoylpropoxy;

$R^4$ is hydrogen;

$R^5$ is hydrogen;

$R^6$ is hydrogen, methyl, benzyl, acetyl, methylsulfonyl, benzoyl or tetrahydropyranyl;

W is a bond, $CH_2$, $C(CH_3)_2$ or $C(CH_3)_2CH_2$;

X is a bond; O; S; $S(O)_2$; or $NR^{10}$, wherein $R^{10}$ is hydrogen, methyl;

or $R^6$ and $R^{10}$, together with the nitrogen to which they are attached, form pyrrolidinyl or 2-oxo-pyrrolidinyl;

or pharmaceutically acceptable salts, enantiomers or diastereomers thereof.

Another embodiment of present invention is (v) a compound of formula (IA), wherein

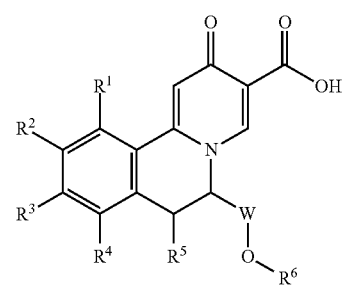

$R^1$ is hydrogen;

$R^2$ is halogen or $C_{1-6}$alkoxy;

$R^3$ is cyano, $C_{1-6}$alkyl, pyrrolidinyl or $OR^7$, wherein
  $R^7$ is $C_{1-6}$alkyl; or $C_{1-6}$alkyl which is substituted once or more times by fluoro, hydroxy, amino, $C_{3-7}$cycloalkyl, phenyl, $C_{1-6}$alkoxy, $C_{1-6}$alkylsulfanyl, $C_{1-6}$alkylsulfonyl, morpholinyl, 2-oxo-pyrrolidinyl, pyrrolidinyl, $diC_{1-6}$alkylamino, $C_{1-6}$alkoxycarbonylamino, $C_{1-6}$alkylpyrrolidinyl or pyrazoyl;

$R^4$ is hydrogen;

$R^5$ is hydrogen;

$R^6$ is hydrogen, $C_{1-6}$alkyl, phenyl-$C_xH_{2x}$ or $C_{1-6}$alkylcarbonyl, wherein
  x is 1-6;

W is $C(R^8)(R^9)C_zH_{2z}$, wherein
  $R^8$ and $R^9$ are independently selected from hydrogen and $C_{1-6}$alkyl,
  z is 0-6;

or pharmaceutically acceptable salts, enantiomers or diastereomers thereof.

A further embodiment of present invention is (vi) a compound of formula (IA), wherein $R^1$ is hydrogen;

$R^2$ is chloro, methoxy or ethoxy;

$R^3$ is cyano, ethyl, pyrrolidinyl, methoxy, ethoxy, benzyloxy, trifluoromethylmethoxy, methoxypropoxy, ethoxyethoxy, cyclopropylmethoxy, hydroxypropoxy, hydroxydimethylpropoxy, hydoxyhexoxy, (methylpyrrolidinyl)ethoxy, aminohexoxy, dimethylamino-propoxy, morpholinylpropoxy, pyrrolidinylpropoxy, (2-oxo-pyrrolidinyl)propoxy, (tert-butoxycarbonylamino)hexoxy, methylsulfanylpropoxy, methylsulfonylpropoxy or pyrazoylpropoxy;

$R^4$ is hydrogen;

$R^5$ is hydrogen;

$R^6$ is hydrogen, methyl, benzyl or acetyl;

W is $CH_2$, $C(CH_3)_2$ or $C(CH_3)_2CH_2$;

or pharmaceutically acceptable salts, enantiomers or diastereomers thereof.

Another embodiment of present invention is (vii) a compound of formula (I), wherein $R^1$, $R^2$, $R^3$ and $R^4$ are independently selected from hydrogen, halogen, $C_{1-6}$alkyl, $diC_{1-6}$alkylamino, cyano, N-containing monocyclic heterocycloalkyl and $OR^7$, wherein
  $R^7$ is hydrogen; $C_{1-6}$alkyl; or $C_{1-6}$alkyl which is substituted once or more times by fluoro, $C_{3-7}$cycloalkyl, phenyl, hydroxyl, amino, $C_{1-6}$alkoxy, $C_{1-6}$alkylsulfanyl, $C_{1-6}$alkylsulfonyl, di$C_{1-6}$alkylamino, $C_{1-6}$alkoxycarbonylamino, monocyclic heterocycloalkyl or imidazolyl;

$R^5$ is hydrogen or $C_{1-6}$alky;

$R^6$ is hydrogen, $C_{1-6}$alkyl, phenyl-$C_xH_{2x}$—, $C_{1-6}$alkylcarbonyl, $C_{1-6}$alkylsulfonyl, benzoyl or monocyclic heterocycloalkyl, wherein
x is 1-6;

W is a bond, $C_yH_{2y}C(R^8)(R^9)C_zH_{2z}$ or $C_yH_{2y}CH(R^8)CH(R^9)C_zH_{2z}$, wherein
$R^8$ and $R^9$ are independently selected from hydrogen, fluoro, hydroxy and $C_{1-6}$alkyl,
y is 0-6;
z is 0-6;

X is a bond; O; S; $S(O)_2$; or $NR^{10}$, wherein $R^{10}$ is hydrogen, $C_{1-6}$alkyl;

or $R^6$ and $R^{10}$, together with the nitrogen to which they are attached, form monocyclic heterocycloalkyl;

with the proviso that when X is a bond, $R^6$ is not hydrogen, $C_{1-6}$alkyl or phenyl-$C_xH_{2x}$—;

or pharmaceutically acceptable salts, enantiomers or diastereomers thereof.

Another embodiment of present invention is (viii) a compound of formula (I) wherein $R^1$, $R^2$, $R^3$ and $R^4$ are independently selected from hydrogen, fluoro, chloro, methyl, ethyl, methoxy, ethoxy, benzyloxy, trifluoromethylmethoxy, methoxyethoxy, methoxypropoxy, ethoxyethoxy, cyclopropylmethoxy, hydroxypropoxy, hydroxydimethylpropoxy, hydoxyhexoxy, (methylpyrrolidinyl)ethoxy, aminohexoxy, dimethylamino-propoxy, (tert-butoxycarbonylamino)hexoxy, methylsulfanylpropoxy, methylsulfonylpropoxy, pyrrolidinylpropoxy, (2-oxo-pyrrolidinyl)propoxy, imidazolylpropoxy, morpholinyl-propoxy, dimethylamino, cyano or pyrrolidinyl;

$R^5$ is hydrogen;

$R^6$ is hydrogen, methyl, benzyl, acetyl, methylsulfonyl, benzoyl, pyrrolidin-1-yl, 2-oxo-pyrrolidinyl or tetrahydropyranyl;

W is a bond, $CH_2$, $C(CH_3)_2$ or $C(CH_3)_2CH_2$;

X is a bond; O; S; $S(O)_2$; or $NR^{10}$, wherein $R^{10}$ is hydrogen, methyl;

or $R^6$ and $R^{10}$, together with the nitrogen to which they are attached, form pyrrolidinyl or 2-oxo-pyrrolidinyl;

with the proviso that when X is a bond, $R^6$ is not hydrogen, $C_{1-6}$alkyl or phenyl-$C_xH_{2x}$—;

or pharmaceutically acceptable salts, enantiomers or diastereomers thereof.

Another embodiment of present invention is ix) a compound of formula (I) wherein
$R^1$ is hydrogen;
$R^2$ is halogen or $C_{1-6}$alkoxy;
$R^3$ is $OR^7$, wherein
$R^7$ is $C_{1-6}$alkyl; or $C_{1-6}$alkyl which is substituted once or more times by fluoro, hydroxy, amino, $C_{3-7}$cycloalkyl, phenyl, $C_{1-6}$alkoxy, $C_{1-6}$alkylsulfanyl, $C_{1-6}$alkylsulfonyl, morpholinyl, 2-oxo-pyrrolidinyl, pyrrolidinyl, di$C_{1-6}$alkylamino, $C_{1-6}$alkoxycarbonylamino, or $C_{1-6}$alkylpyrrolidinyl;
$R^4$ is hydrogen;
$R^5$ is hydrogen;
$R^6$ is hydrogen, $C_{1-6}$alkyl, phenyl-$C_xH_{2x}$, $C_{1-6}$alkylcarbonyl, $C_{1-6}$alkylsulfonyl, benzoyl or tetrahydropyranyl, wherein
x is 1-6;
W is a bond, $C(R^8)(R^9)C_zH_{2z}$, wherein
$R^8$ and $R^9$ are independently selected from hydrogen and $C_{1-6}$alkyl,
z is 0-6;

X is a bond; O; S; $S(O)_2$; or $NR^{10}$, wherein $R^{10}$ is hydrogen, $C_{1-6}$alkyl;

or $R^6$ and $R^{10}$, together with the nitrogen to which they are attached, form pyrrolidinyl or 2-oxo-pyrrolidinyl;

with the proviso that $R^6$ is not hydrogen, $C_{1-6}$alkyl or phenyl-$C_xH_{2x}$— when X is a bond; or pharmaceutically acceptable salts, enantiomers or diastereomers thereof.

A further embodiment of present invention is (x) a compound of formula (I) wherein
$R^1$ is hydrogen;
$R^2$ is chloro, methoxy or ethoxy;
$R^3$ is methoxy, ethoxy, benzyloxy, trifluoromethylmethoxy, methoxyethoxy, methoxypropoxy, ethoxyethoxy, cyclopropylmethoxy, hydroxypropoxy, hydroxy-dimethylpropoxy, hydoxyhexoxy, (methylpyrrolidinyl)ethoxy, aminohexoxy, dimethylaminopropoxy, morpholinylpropoxy, pyrrolidinylpropoxy, (2-oxo-pyrrolidinyl)propoxy, (tert-butoxycarbonylamino)hexoxy, methylsulfanylpropoxy, methylsulfonylpropoxy;
$R^4$ is hydrogen;
$R^5$ is hydrogen;
$R^6$ is hydrogen, methyl, benzyl, acetyl, methylsulfonyl, benzoyl or tetrahydropyranyl;
W is a bond, $CH_2$, $C(CH_3)_2$ or $C(CH_3)_2CH_2$;
X is a bond; O; S; $S(O)_2$; or $NR^{10}$, wherein $R^{10}$ is hydrogen, methyl;

or $R^6$ and $R^{10}$, together with the nitrogen to which they are attached, form pyrrolidinyl or 2-oxo-pyrrolidinyl;

with the proviso that $R^6$ is not hydrogen, methyl or benzyl when X is a bond; or pharmaceutically acceptable salts, enantiomers or diastereomers thereof.

Another embodiment of present invention is (xi) a compound of formula (IA), wherein,

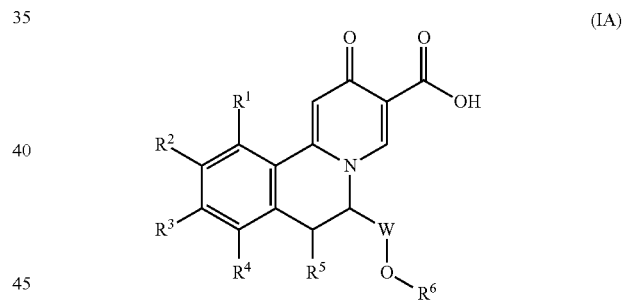

(IA)

$R^1$ is hydrogen;
$R^2$ is halogen or $C_{1-6}$alkoxy;
$R^3$ is $OR^7$, wherein
$R^7$ is $C_{1-6}$alkyl; or $C_{1-6}$alkyl which is substituted once or more times by fluoro, hydroxy, amino, $C_{3-7}$cycloalkyl, phenyl, $C_{1-6}$alkoxy, $C_{1-6}$alkylsulfanyl, $C_{1-6}$alkylsulfonyl, morpholinyl, 2-oxo-pyrrolidinyl, pyrrolidinyl, di$C_{1-6}$alkylamino, $C_{1-6}$alkoxycarbonylamino or $C_{1-6}$alkylpyrrolidinyl;
$R^4$ is hydrogen;
$R^5$ is hydrogen;
$R^6$ is hydrogen, $C_{1-6}$alkyl, phenyl-$C_xH_{2x}$ or $C_{1-6}$alkylcarbonyl, wherein
x is 1-6;
W is $C(R^8)(R^9)C_zH_{2z}$, wherein
$R^8$ and $R^9$ are independently selected from hydrogen and $C_{1-6}$alkyl,
z is 0-6;
or pharmaceutically acceptable salts, enantiomers or diastereomers thereof.

A further embodiment of present invention is (xii) a compound of formula (IA), wherein,
$R^1$ is hydrogen;
$R^2$ is chloro, methoxy or ethoxy;
$R^3$ is methoxy, ethoxy, benzyloxy, trifluoromethylmethoxy, methoxypropoxy, ethoxyethoxy, cyclopropylmethoxy, hydroxypropoxy, hydroxydimethylpropoxy, hydoxyhexoxy, (methylpyrrolidinyl)ethoxy, aminohexoxy, dimethylamino-propoxy, morpholinylpropoxy, pyrrolidinylpropoxy, (2-oxo-pyrrolidinyl)propoxy, (tert-butoxycarbonylamino)hexoxy, methylsulfanylpropoxy, methylsulfonylpropoxy;
$R^4$ is hydrogen;
$R^5$ is hydrogen;
$R^6$ is hydrogen, methyl, benzyl or acetyl;
W is $CH_2$, $C(CH_3)_2$ or $C(CH_3)_2CH_2$;
or pharmaceutically acceptable salts, enantiomers or diastereomers thereof.

Another embodiment of present invention is (xiii) a compound of formula (I) or pharmaceutically acceptable salts, enantiomers or diastereomers thereof, wherein
$R^1$ is hydrogen;
$R^2$ is halogen or $C_{1-6}$alkoxy;
$R^3$ is $OR^7$, wherein
  $R^7$ is $C_{1-6}$alkyl; or $C_{1-6}$alkyl which is substituted once or more times by fluoro, hydroxy, amino, $C_{3-7}$cycloalkyl, phenyl, $C_{1-6}$alkoxy, $C_{1-6}$alkylsulfanyl, morpholinyl or $C_{1-6}$alkoxycarbonylamino;
$R^4$ is hydrogen;
$R^5$ is hydrogen;
$R^6$ is hydrogen or $C_{1-6}$alkyl;
W is $C(R^8)(R^9)C_zH_{2z}$, wherein
  $R^8$ and $R^9$ are independently selected from hydrogen and $C_{1-6}$alkyl,
  z is 0-6;
X is O.

A further embodiment of present invention is (xiv) a compound of formula (I) or pharmaceutically acceptable salts, enantiomers or diastereomers thereof, wherein
$R^1$ is hydrogen;
$R^2$ is chloro or methoxy;
$R^3$ is methoxy, benzyloxy, trifluoromethylmethoxy, methoxypropoxy, ethoxyethoxy, cyclopropylmethoxy, hydroxypropoxy, hydroxydimethylpropoxy, aminohexoxy, morpholinylpropoxy, (tert-butoxycarbonylamino)hexoxy or methylsulfanylpropoxy;
$R^4$ is hydrogen;
$R^5$ is hydrogen;
$R^6$ is hydrogen or methyl;
W is $C(CH_3)_2CH_2$;
X is O.

Another embodiment of present invention is (xv) a compound of formula (I) or pharmaceutically acceptable salts, enantiomers or diastereomers thereof, wherein $R^2$ is halogen or $C_{1-6}$alkoxy.

A further embodiment of present invention is (xvi) a compound of formula (I) or pharmaceutically acceptable salts, enantiomers or diastereomers thereof, wherein $R^2$ is methoxy or chloro.

Another embodiment of present invention is (xvii) a compound of formula (I) or pharmaceutically acceptable salts, enantiomers or diastereomers thereof, wherein $R^3$ is $C_{1-6}$alkoxy$C_{1-6}$alkoxy.

Another embodiment of present invention is (xviii) a compound of formula (I) or pharmaceutically acceptable salts, enantiomers or diastereomers thereof, wherein $R^3$ is methoxypropoxy.

Another embodiment of present invention is (xix) a compound of formula (I) or pharmaceutically acceptable salts, enantiomers or diastereomers thereof, wherein $R^6$ is hydrogen or $C_{1-6}$alkyl.

A further embodiment of present invention is (xx) a compound of formula (I) or pharmaceutically acceptable salts, enantiomers or diastereomers thereof, wherein $R^6$ is methyl.

Another embodiment of present invention is (xxi) a compound of formula (I) or pharmaceutically acceptable salts, enantiomers or diastereomers thereof, wherein W $C(CH_3)_2CH_2$.

A further embodiment of present invention is (xxii) a compound of formula (I), wherein
$R^1$ is hydrogen;
$R^2$ is chloro or methoxy;
$R^3$ is methoxy, benzyloxy, trifluoromethylmethoxy, 3-methoxypropoxy, 2-ethoxyethoxy, cyclopropylmethoxy, 3-hydroxypropoxy, 3-hydroxy-2,2-dimethylpropoxy, 6-aminohexoxy, 3-morpholinyl-propoxy, (tert-butoxycarbonylamino)hexoxy or 3-methylsulfanylpropoxy;
$R^4$ is hydrogen;
$R^5$ is hydrogen;
$R^6$ is hydrogen or methyl;
W is $C(CH_3)_2CH_2$;
X is O;
or pharmaceutically acceptable salts, enantiomers or diastereomers thereof.

Particular compounds of formula (I) according to the invention are the following:
9-Benzyloxy-10-methoxy-6-(2-methoxy-1,1-dimethyl-ethyl)-2-oxo-6,7-dihydrobenzo[a]quinolizine-3-carboxylic acid;
9,10-Dimethoxy-6-(2-methoxy-1,1-dimethyl-ethyl)-2-oxo-6,7-dihydrobenzo[a]quinolizine-3-carboxylic acid;
10-Methoxy-6-(2-methoxy-1,1-dimethyl-ethyl)-2-oxo-9-(2,2,2-trifluoroethoxy)-6,7-dihydrobenzo[a]quinolizine-3-carboxylic acid;
10-Methoxy-6-(2-methoxy-1,1-dimethyl-ethyl)-9-(3-morpholinopropoxy)-2-oxo-6,7-dihydrobenzo[a]quinolizine-3-carboxylic acid;
9-(6-Hydroxyhexoxy)-10-methoxy-6-(2-methoxy-1,1-dimethyl-ethyl)-2-oxo-6,7-dihydrobenzo[a]quinolizine-3-carboxylic acid;
9-(3-Hydroxypropoxy)-10-methoxy-6-(2-methoxy-1,1-dimethyl-ethyl)-2-oxo-6,7-dihydrobenzo[a]quinolizine-3-carboxylic acid;
9-(3-Hydroxy-2,2-dimethyl-propoxy)-10-methoxy-6-(2-methoxy-1,1-dimethyl-ethyl)-2-oxo-6,7-dihydrobenzo[a]quinolizine-3-carboxylic acid;
9-(2-Ethoxyethoxy)-10-methoxy-6-(2-methoxy-1,1-dimethyl-ethyl)-2-oxo-6,7-dihydrobenzo[a]quinolizine-3-carboxylic acid;
9-(Cyclopropylmethoxy)-10-methoxy-6-(2-methoxy-1,1-dimethyl-ethyl)-2-oxo-6,7-dihydrobenzo[a]quinolizine-3-carboxylic acid;
10-Methoxy-6-(2-methoxy-1,1-dimethyl-ethyl)-9-(3-methylsulfanylpropoxy)-2-oxo-6,7-dihydrobenzo[a]quinolizine-3-carboxylic acid;
10-Methoxy-6-(2-methoxy-1,1-dimethyl-ethyl)-2-oxo-9-(3-pyrrolidin-1-ylpropoxy)-6,7-dihydrobenzo[a]quinolizine-3-carboxylic acid;
10-Methoxy-6-(2-methoxy-1,1-dimethyl-ethyl)-2-oxo-9-[3-(2-oxopyrrolidin-1-yl)propoxy]-6,7-dihydrobenzo[a]quinolizine-3-carboxylic acid;

9-[3-(Dimethylamino)propoxy]-10-methoxy-6-(2-methoxy-1,1-dimethyl-ethyl)-2-oxo-6,7-dihydrobenzo[a]quinolizine-3-carboxylic acid;

9-[6-(tert-Butoxycarbonylamino)hexoxy]-10-methoxy-6-(2-methoxy-1,1-dimethyl-ethyl)-2-oxo-6,7-dihydrobenzo[a]quinolizine-3-carboxylic acid;

10-Methoxy-6-(2-methoxy-1,1-dimethyl-ethyl)-9-(3-methylsulfonylpropoxy)-2-oxo-6,7-dihydrobenzo[a]quinolizine-3-carboxylic acid;

9-(6-Aminohexoxy)-10-methoxy-6-(2-methoxy-1,1-dimethyl-ethyl)-2-oxo-6,7-dihydrobenzo[a]quinolizine-3-carboxylic acid;

10-Methoxy-6-(2-methoxy-1,1-dimethyl-ethyl)-9-[2-(1-methylpyrrolidin-2-yl)ethoxy]-2-oxo-6,7-dihydrobenzo[a]quinolizine-3-carboxylic acid;

10-Methoxy-6-(methoxymethyl)-9-(3-methoxypropoxy)-2-oxo-6,7-dihydrobenzo[a]quinolizine-3-carboxylic acid;

6-(1-Hydroxy-1-methyl-ethyl)-10-methoxy-9-(3-methoxypropoxy)-2-oxo-6,7-dihydrobenzo[a]quinolizine-3-carboxylic acid;

(+)-6-(1-Hydroxy-1-methyl-ethyl)-10-methoxy-9-(3-methoxypropoxy)-2-oxo-6,7-dihydrobenzo[a]quinolizine-3-carboxylic acid;

(−)-6-(1-Hydroxy-1-methyl-ethyl)-10-methoxy-9-(3-methoxypropoxy)-2-oxo-6,7-dihydrobenzo[a]quinolizine-3-carboxylic acid;

6-(2-Benzyloxy-1,1-dimethyl-ethyl)-10-methoxy-9-(3-methoxypropoxy)-2-oxo-6,7-dihydrobenzo[a]quinolizine-3-carboxylic acid;

6-(2-Hydroxy-1,1-dimethyl-ethyl)-10-methoxy-9-(3-methoxypropoxy)-2-oxo-6,7-dihydrobenzo[a]quinolizine-3-carboxylic acid;

(+)-6-(2-Hydroxy-1,1-dimethyl-ethyl)-10-methoxy-9-(3-methoxypropoxy)-2-oxo-6,7-dihydrobenzo[a]quinolizine-3-carboxylic acid;

(−)-6-(2-Hydroxy-1,1-dimethyl-ethyl)-10-methoxy-9-(3-methoxypropoxy)-2-oxo-6,7-dihydrobenzo[a]quinolizine-3-carboxylic acid;

10-Methoxy-6-(2-methoxy-1,1-dimethyl-ethyl)-9-(3-methoxypropoxy)-2-oxo-6,7-dihydrobenzo[a]quinolizine-3-carboxylic acid;

(+)-10-Methoxy-6-(2-methoxy-1,1-dimethyl-ethyl)-9-(3-methoxypropoxy)-2-oxo-6,7-dihydrobenzo[a]quinolizine-3-carboxylic acid;

(−)-10-Methoxy-6-(2-methoxy-1,1-dimethyl-ethyl)-9-(3-methoxypropoxy)-2-oxo-6,7-dihydrobenzo[a]quinolizine-3-carboxylic acid;

10-Chloro-6-(2-methoxy-1,1-dimethyl-ethyl)-9-(3-methoxypropoxy)-2-oxo-6,7-dihydrobenzo[a]quinolizine-3-carboxylic acid;

(+)-10-Chloro-6-(2-methoxy-1,1-dimethyl-ethyl)-9-(3-methoxypropoxy)-2-oxo-6,7-dihydrobenzo[a]quinolizine-3-carboxylic acid;

(−)-10-Chloro-6-(2-methoxy-1,1-dimethyl-ethyl)-9-(3-methoxypropoxy)-2-oxo-6,7-dihydrobenzo[a]quinolizine-3-carboxylic acid;

9,10-Diethoxy-6-(hydroxymethyl)-2-oxo-6,7-dihydrobenzo[a]quinolizine-3-carboxylic acid;

6-(Acetoxymethyl)-9,10-diethoxy-2-oxo-6,7-dihydrobenzo[a]quinolizine-3-carboxylic acid;

10-Methoxy-6-(2-methoxy-1,1-dimethyl-ethyl)-2-oxo-9-(3-pyrazol-1-ylpropoxy)-6,7-dihydrobenzo[a]quinolizine-3-carboxylic acid;

9-Ethyl-10-methoxy-6-(2-methoxy-1,1-dimethyl-ethyl)-2-oxo-6,7-dihydrobenzo[a]quinolizine-3-carboxylic acid;

10-Methoxy-6-(2-methoxy-1,1-dimethyl-ethyl)-2-oxo-9-pyrrolidin-1-yl-6,7-dihydrobenzo[a]quinolizine-3-carboxylic acid;

9-Cyano-10-methoxy-6-(2-methoxy-1,1-dimethyl-ethyl)-2-oxo-6,7-dihydrobenzo[a]quinolizine-3-carboxylic acid;

or pharmaceutically acceptable salt, enantiomer or diastereomer thereof.

More particularly, the invention relates to the following compounds of formula (I):

9-Benzyloxy-10-methoxy-6-(2-methoxy-1,1-dimethyl-ethyl)-2-oxo-6,7-dihydrobenzo[a]quinolizine-3-carboxylic acid;

9,10-Dimethoxy-6-(2-methoxy-1,1-dimethyl-ethyl)-2-oxo-6,7-dihydrobenzo[a]quinolizine-3-carboxylic acid;

10-Methoxy-6-(2-methoxy-1,1-dimethyl-ethyl)-2-oxo-9-(2,2,2-trifluoroethoxy)-6,7-dihydrobenzo[a]quinolizine-3-carboxylic acid;

10-Methoxy-6-(2-methoxy-1,1-dimethyl-ethyl)-9-(3-morpholinopropoxy)-2-oxo-6,7-dihydrobenzo[a]quinolizine-3-carboxylic acid;

9-(3-Hydroxypropoxy)-10-methoxy-6-(2-methoxy-1,1-dimethyl-ethyl)-2-oxo-6,7-dihydrobenzo[a]quinolizine-3-carboxylic acid;

9-(3-Hydroxy-2,2-dimethyl-propoxy)-10-methoxy-6-(2-methoxy-1,1-dimethyl-ethyl)-2-oxo-6,7-dihydrobenzo[a]quinolizine-3-carboxylic acid;

9-(2-Ethoxyethoxy)-10-methoxy-6-(2-methoxy-1,1-dimethyl-ethyl)-2-oxo-6,7-dihydrobenzo[a]quinolizine-3-carboxylic acid;

9-(Cyclopropylmethoxy)-10-methoxy-6-(2-methoxy-1,1-dimethyl-ethyl)-2-oxo-6,7-dihydrobenzo[a]quinolizine-3-carboxylic acid;

10-Methoxy-6-(2-methoxy-1,1-dimethyl-ethyl)-9-(3-methylsulfanylpropoxy)-2-oxo-6,7-dihydrobenzo[a]quinolizine-3-carboxylic acid;

9-[6-(tert-Butoxycarbonylamino)hexoxy]-10-methoxy-6-(2-methoxy-1,1-dimethyl-ethyl)-2-oxo-6,7-dihydrobenzo[a]quinolizine-3-carboxylic acid;

9-(6-Aminohexoxy)-10-methoxy-6-(2-methoxy-1,1-dimethyl-ethyl)-2-oxo-6,7-dihydrobenzo[a]quinolizine-3-carboxylic acid;

6-(2-Hydroxy-1,1-dimethyl-ethyl)-10-methoxy-9-(3-methoxypropoxy)-2-oxo-6,7-dihydrobenzo[a]quinolizine-3-carboxylic acid;

(+)-6-(2-Hydroxy-1,1-dimethyl-ethyl)-10-methoxy-9-(3-methoxypropoxy)-2-oxo-6,7-dihydrobenzo[a]quinolizine-3-carboxylic acid;

10-Methoxy-6-(2-methoxy-1,1-dimethyl-ethyl)-9-(3-methoxypropoxy)-2-oxo-6,7-dihydrobenzo[a]quinolizine-3-carboxylic acid;

(+)-10-Methoxy-6-(2-methoxy-1,1-dimethyl-ethyl)-9-(3-methoxypropoxy)-2-oxo-6,7-dihydrobenzo[a]quinolizine-3-carboxylic acid;

10-Chloro-6-(2-methoxy-1,1-dimethyl-ethyl)-9-(3-methoxypropoxy)-2-oxo-6,7-dihydrobenzo[a]quinolizine-3-carboxylic acid;

(+)-10-Chloro-6-(2-methoxy-1,1-dimethyl-ethyl)-9-(3-methoxypropoxy)-2-oxo-6,7-dihydrobenzo[a]quinolizine-3-carboxylic acid;

or pharmaceutically acceptable salt, enantiomer or diastereomer thereof.

Another embodiment of present invention is (xxiii) a compound of formula (I), wherein $R^1$ is hydrogen;

$R^2$ is halogen or $C_{1-6}$alkoxy;

$R^3$ is $C_{1-6}$alkoxy or $C_{1-6}$alkoxy$C_{1-6}$alkoxy;

$R^4$ is hydrogen;

$R^5$ is hydrogen;
$R^6$ is hydrogen, $C_{1-6}$alkyl, $C_{1-6}$alkylcarbonyl, $C_{1-6}$alkylsulfonyl, benzoyl or tetrahydropyranyl;
W is a bond, $C(R^8)(R^9)C_zH_{2z}$, wherein
$R^8$ and $R^9$ are independently selected from hydrogen and $C_{1-6}$alkyl,
z is 0-6;
X is a bond; S; $S(O)_2$; or $NR^{10}$, wherein $R^{10}$ is hydrogen, $C_{1-6}$alkyl;
or $R^6$ and $R^{10}$, together with the nitrogen to which they are attached, form pyrrolidinyl or 2-oxo-pyrrolidinyl;
or pharmaceutically acceptable salts, enantiomers or diastereomers thereof.

A further embodiment of present invention is (xxiv) a compound of formula (I), wherein
$R^1$ is hydrogen;
$R^2$ is chloro or ethoxy;
$R^3$ is ethoxy, methoxyethoxy or methoxypropoxy;
$R^4$ is hydrogen;
$R^5$ is hydrogen;
$R^6$ is hydrogen, methyl, acetyl, methylsulfonyl, benzoyl or tetrahydropyranyl;
W is a bond or $CH_2$;
X is a bond; S; $S(O)_2$; or $NR^{10}$, wherein $R^{10}$ is hydrogen, methyl;
or $R^6$ and $R^{10}$, together with the nitrogen to which they are attached, form pyrrolidinyl or 2-oxo-pyrrolidinyl;
or pharmaceutically acceptable salts, enantiomers or diastereomers thereof.

Particular compounds of formula (I) according to the invention are the following:
10-Chloro-9-(3-methoxypropoxy)-2-oxo-6-tetrahydropyran-4-yl-6,7-dihydrobenzo[a]quinolizine-3-carboxylic acid;
10-Chloro-9-(2-methoxyethoxy)-6-(methylsulfanylmethyl)-2-oxo-6,7-dihydrobenzo[a]quinolizine-3-carboxylic acid;
10-Chloro-9-(2-methoxyethoxy)-6-(methylsulfonylmethyl)-2-oxo-6,7-dihydrobenzo[a]quinolizine-3-carboxylic acid;
6-(Aminomethyl)-9,10-diethoxy-2-oxo-6,7-dihydrobenzo[a]quinolizine-3-carboxylic acid;
9,10-Diethoxy-6-(methanesulfonamidomethyl)-2-oxo-6,7-dihydrobenzo[a]quinolizine-3-carboxylic acid;
6-(Benzamidomethyl)-9,10-diethoxy-2-oxo-6,7-dihydrobenzo[a]quinolizine-3-carboxylic acid;
9,10-Diethoxy-2-oxo-6-[(2-oxopyrrolidin-1-yl)methyl]-6,7-dihydrobenzo[a]quinolizine-3-carboxylic acid;
6-[[Acetyl(methyl)amino]methyl]-9,10-diethoxy-2-oxo-6,7-dihydrobenzo[a]quinolizine-3-carboxylic acid;
9,10-Diethoxy-2-oxo-6-(pyrrolidin-1-ylmethyl)-6,7-dihydrobenzo[a]quinolizine-3-carboxylic acid;
6-[(Dimethylamino)methyl]-9,10-diethoxy-2-oxo-6,7-dihydrobenzo[a]quinolizine-3-carboxylic acid;
or pharmaceutically acceptable salt, enantiomer or diastereomer thereof.

It will be appreciated, that the compounds of general formula (I) in this invention may be derivatised at functional groups to provide derivatives which are capable of conversion back to the parent compound in vivo. Physiologically acceptable and metabolically labile derivatives, which are capable of producing the parent compounds of general formula (I) in vivo are also within the scope of this invention.

SYNTHESIS

The compounds of the present invention can be prepared by any conventional means. Suitable processes for synthesizing these compounds as well as their starting materials are provided in the schemes below and in the examples. All substituents, in particular, $R^1$ to $R^6$, $R^{10}$, W and X are as defined above unless otherwise indicated. Furthermore, and unless explicitly otherwise stated, all reactions, reaction conditions, abbreviations and symbols have the meanings well known to a person of ordinary skill in organic chemistry.

General synthetic route for intermediates (Scheme 1)

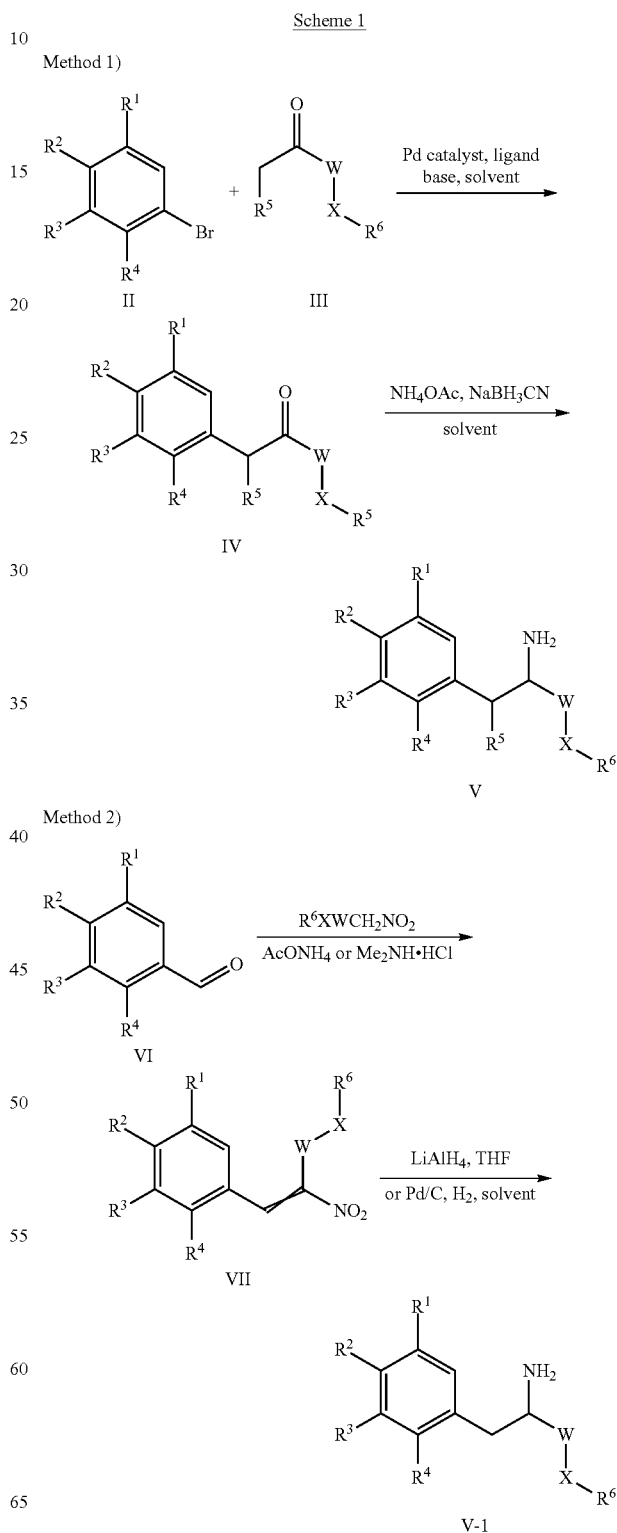

Method 3)

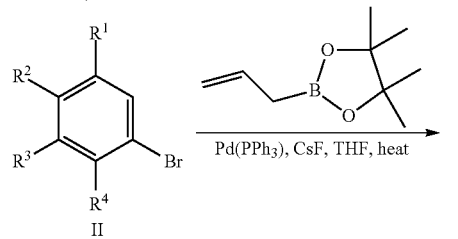

II

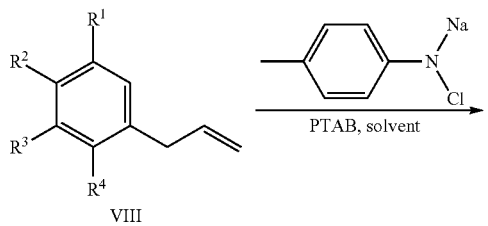

VIII

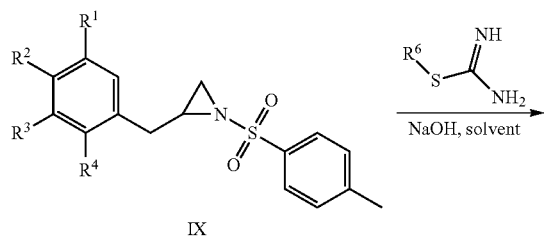

IX

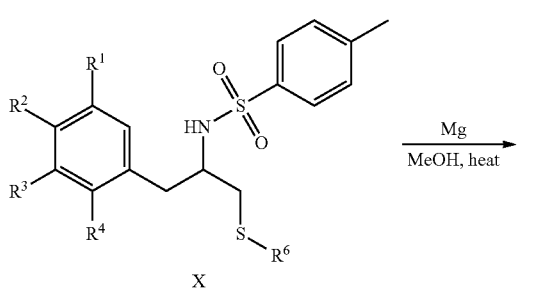

X $R^6$ is $C_{1-6}$alkyl

Method 4)

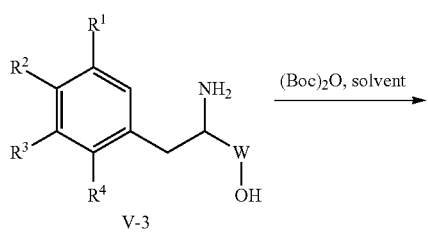

V-3

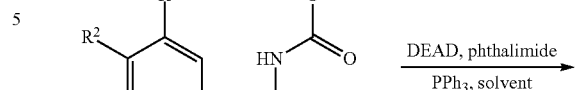

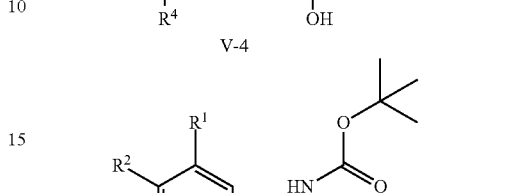

V-4

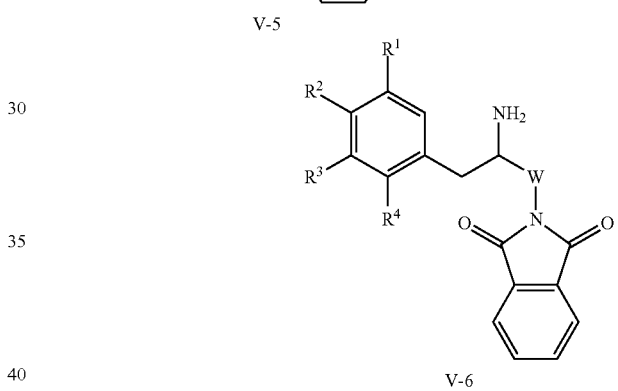

V-5

V-6

Intermediates can be prepared according to Scheme 1.

By Method 1), coupling reaction of II with III affords IV. The reaction can be carried out in the presence of a Pd catalyst such as $Pd_2(dba)_3$, $Pd(PPh_3)_4$ or $PdCl_2(PPh_3)_2$, a ligand such as Xantphos, and a suitable base such as tert-BuONa, $Na_2CO_3$ or $Cs_2CO_3$, in a suitable solvent such as THF, toluene or 1,4-dioxane at a temperature between room temperature and 130° C. Reductive amination of IV affords Compound V.

By Method 2), Compound VI reacts with nitroalkane in the presence of ammonium acetate or dimethylamine hydrochloride affords VII, which is reduced by $LiAlH_4$ or undergoes hydrogenation in the presence of Pd/C to give V-1.

By Method 3), coupling reaction of II with 2-allyl-4,4,5,5-tetramethyl-1,3,2-dioxaborolane affords VIII. The reaction can be carried out in the presence of a Pd catalyst such as $Pd(PPh_3)_4$, and a suitable base such as CsF and $Cs_2CO_3$, in a suitable solvent such as THF at a temperature between room temperature and 100° C. Then VIII is treated with [chloro(p-tolylsulfonyl)amino]sodium at room temperature in the presence of PTAB in a suitable solvent such as acetonitrile to give IX. Compound IX reacts with S—$C_{1-6}$alkylisothiourea in the presence of NaOH in a suitable solvent such as $THF/H_2O$ to afford X. After heating X with magnesium in methanol at a temperature between 50° C. and 100° C., compound V-2 is obtained.

By Method 4), the amino group of Compound V-3 is protected by Boc group to give V-4. Then Compound V-4 reacts with phthalimide in the presence DEAD and PPh₃ in a solvent such as THF at a temperature between −10° C. and 80° C. to give V-5, which is de-protected by treating with HCl/dioxane, HCl/EtOAc, or TFA to give V-6.
General Synthetic Route for Compounds I, Ia, Ib, Ic and Id (Scheme 2)
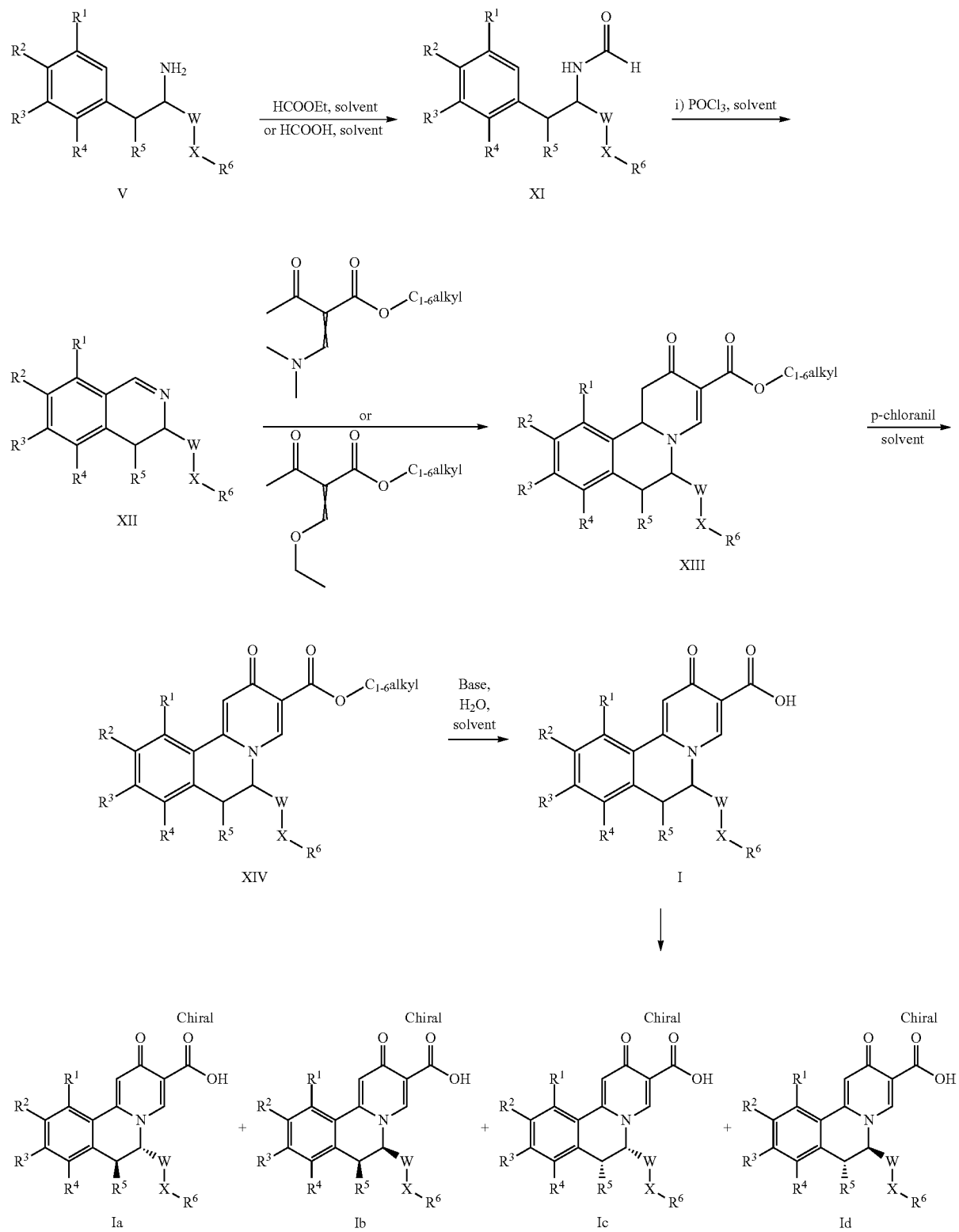

The compound of formula I, Ia, Ib, Ic and Id can be prepared according to Scheme 2. Compound V is heated with ethyl formate or formic acid in a solvent such as ethanol or dioxane affords Compound XI. Compound XI is treated with $POCl_3$ in a suitable solvent such as acetonitrile or DCM at a temperature between room temperature and 100° C. to give Compound XII. Compound XII reacts with $C_{1-6}$alkyl 2-(dimethylaminomethylene)-3-oxo-butanoate in a solvent such as DMSO, DMF, or reacts with $C_{1-6}$alkyl 2-(ethoxymethylene)-3-oxo-butanoate in a solvent such as ethanol to give Compound XIII. After dehydrogenation of XIII by p-chloranil, compound XIV is obtained. Hydrolyzation of XIV by lithium hydroxide or sodium hydroxide in a suitable solvent such as $THF/H_2O$, $EtOH/H_2O$ or $MeOH/H_2O$ affords Compound I. Compound I can be separated by prep-HPLC and chiral HPLC to give Compounds Ia, Ib, Ic and Id.

General Synthetic Route for Compounds I-1
(Scheme 3)

General Synthetic Route for Compounds I-2
(Scheme 4)

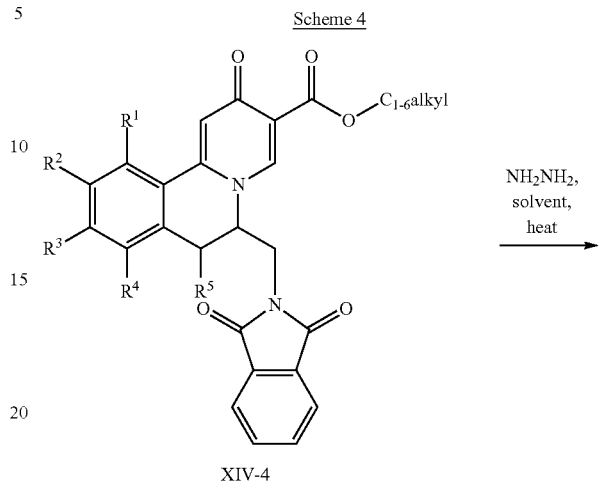

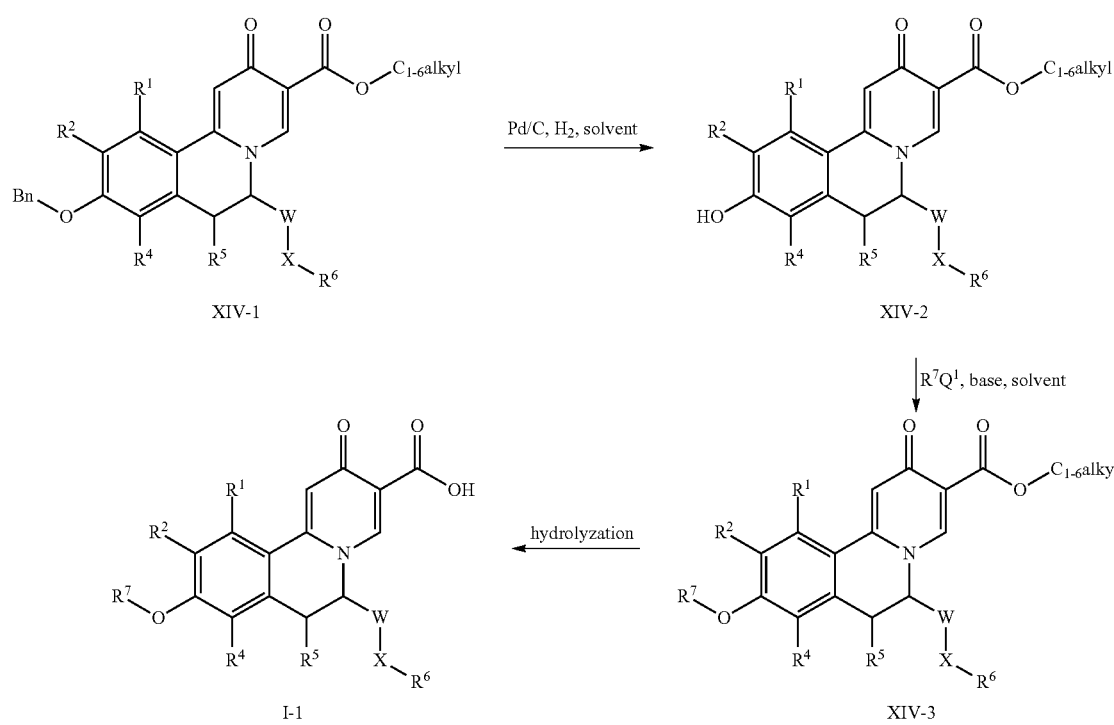

$Q^1$ is halogen, —O—S(O)$_2$CH$_3$ or —O—S(O)$_2$-(4-CH$_3$-Ph).

The compound of formula I-1 can be prepared according to Scheme 3. Debenzylation of Compound XIV-1 by hydrogenation is carried out in the presence of Pd/C in a solvent such as ethanol, THF, methanol to afford XIV-2. Then XIV-2 reacts with halides, mesylates or tosylates in the presence of a base such as $K_2CO_3$ in a solvent such as acetone or DMF to give XIV-3. Hydrolyzation of XIV by lithium hydroxide or sodium hydroxide in a suitable solvent such as $THF/H_2O$, $EtOH/H_2O$ or $MeOH/H_2O$ affords I-1.

-continued

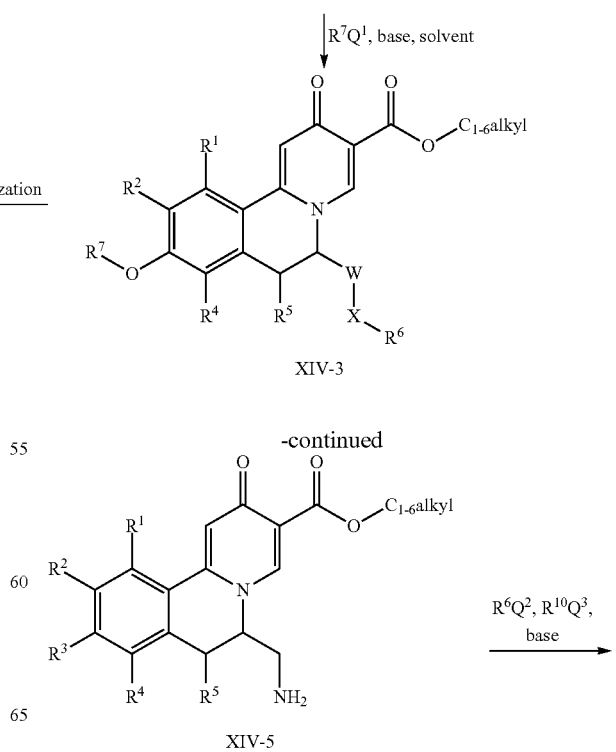

-continued

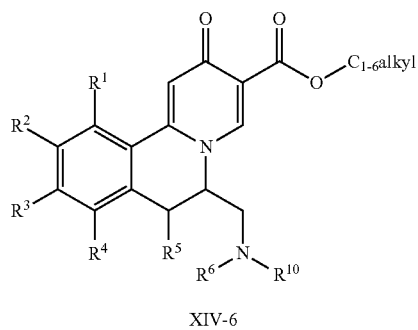

XIV-6

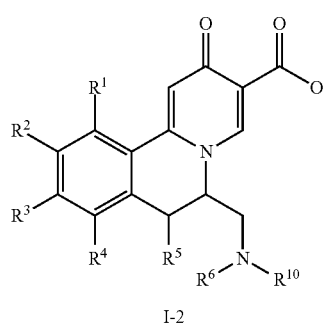

I-2

$Q^2$ is halogen, —O—S(O)$_2$CH$_3$ or —O—S(O)$_2$-(4-CH$_3$-Ph);

$Q^3$ is halogen, —O—S(O)$_2$CH$_3$ or —O—S(O)$_2$-(4-CH$_3$-Ph).

The compound of formula I-2 can be prepared according to Scheme 4. Compound XIV-4 reacts with hydrazine in a solvent such as ethanol at a temperature between room temperature and 100° C. to give XIV-5. Compound XIV-5 reacts with halides, mesylates, tosylates, acids, acyl chlorides to give XIV-6. Hydrolyzation of XIV-6 by lithium hydroxide or sodium hydroxide in a suitable solvent such as THF/H$_2$O, EtOH/H$_2$O or MeOH/H$_2$O affords Compound I-2.

This invention also relates to a process for the preparation of a compound of formula (I) comprising (a) hydrolysis of a compound of formula (A)

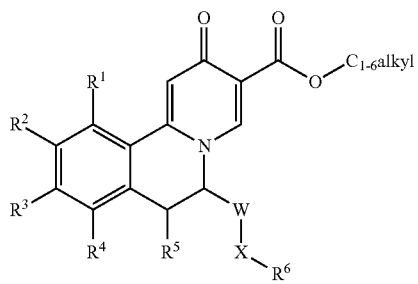

in the presence of a base;

(b) hydrolyzation of a compound of formula (B)

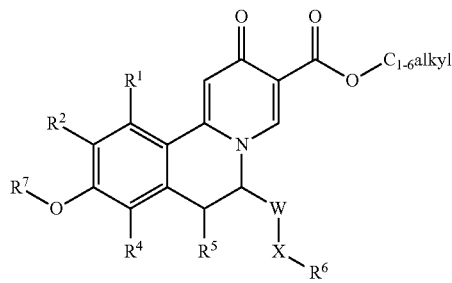

in the presence of a base; or
(c) hydrolyzation of a compound of formula (C)

[structure C]

in the presence of a base;
wherein a base can be for example lithium hydroxide or sodium hydroxide. $R^1$ to $R^6$, $R^{10}$, W and X are defined above unless otherwise indicated.

A compound of formula (I) when manufactured according to the above process is also an object of the invention.

Pharmaceutical Compositions and Administration

The invention also relates to a compound of formula (I) for use as therapeutically active substance.

Another embodiment provides pharmaceutical compositions or medicaments containing the compounds of the invention and a therapeutically inert carrier, diluent or excipient, as well as methods of using the compounds of the invention to prepare such compositions and medicaments. In one example, compounds of formula (I) may be formulated by mixing at ambient temperature at the appropriate pH, and at the desired degree of purity, with physiologically acceptable carriers, i.e., carriers that are non-toxic to recipients at the dosages and concentrations employed into a galenical administration form. The pH of the formulation depends mainly on the particular use and the concentration of compound, but preferably ranges anywhere from about 3 to about 8. In one example, a compound of formula (I) is formulated in an acetate buffer, at pH 5. In another embodiment, the compounds of formula (I) are sterile. The compound may be stored, for example, as a solid or amorphous composition, as a lyophilized formulation or as an aqueous solution.

Compositions are formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "effective amount" of the compound to be administered will be governed by such considerations, and is the minimum amount necessary to inhibit HBsAg. For example, such amount may be below the amount that is toxic to normal cells, or the mammal as a whole.

In one example, the pharmaceutically effective amount of the compound of the invention administered parenterally per dose will be in the range of about 0.01 to 100 mg/kg, alternatively about 0.01 to 100 mg/kg of patient body weight per day, with the typical initial range of compound used being 0.3 to 15 mg/kg/day. In another embodiment, oral unit dosage forms, such as tablets and capsules, preferably contain from about 0.1 to about 1000 mg of the compound of the invention.

The compounds of the invention may be administered by any suitable means, including oral, topical (including buccal and sublingual), rectal, vaginal, transdermal, parenteral, subcutaneous, intraperitoneal, intrapulmonary, intradermal, intrathecal and epidural and intranasal, and, if desired for local treatment, intralesional administration. Parenteral infusions include intramuscular, intravenous, intraarterial, intraperitoneal, or subcutaneous administration.

The compounds of the present invention may be administered in any convenient administrative form, e.g., tablets, powders, capsules, solutions, dispersions, suspensions, syrups, sprays, suppositories, gels, emulsions, patches, etc. Such compositions may contain components conventional in pharmaceutical preparations, e.g., diluents, carriers, pH modifiers, sweeteners, bulking agents, and further active agents.

A typical formulation is prepared by mixing a compound of the present invention and a carrier or excipient. Suitable carriers and excipients are well known to those skilled in the art and are described in detail in, e.g., Ansel, Howard C., et al., *Ansel's Pharmaceutical Dosage Forms and Drug Delivery Systems*. Philadelphia: Lippincott, Williams & Wilkins, 2004; Gennaro, Alfonso R., et al. *Remington: The Science and Practice of Pharmacy*. Philadelphia: Lippincott, Williams & Wilkins, 2000; and Rowe, Raymond C. *Handbook of Pharmaceutical Excipients*. Chicago, Pharmaceutical Press, 2005. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound of the present invention or pharmaceutical composition thereof) or aid in the manufacturing of the pharmaceutical product (i.e., medicament).

An example of a suitable oral dosage form is a tablet containing about 0.1 to 1000 mg of the compound of the invention compounded with about 0 to 2000 mg anhydrous lactose, about 0 to 2000 mg sodium croscarmellose, about 0 to 2000 mg polyvinylpyrrolidone (PVP) K30, and about 0 to 2000 mg magnesium stearate. The powdered ingredients are first mixed together and then mixed with a solution of the PVP. The resulting composition can be dried, granulated, mixed with the magnesium stearate and compressed to tablet form using conventional equipment. An example of an aerosol formulation can be prepared by dissolving the compound, for example 0.1 to 1000 mg, of the invention in a suitable buffer solution, e.g. a phosphate buffer, adding a tonicifier, e.g. a salt such sodium chloride, if desired. The solution may be filtered, e.g., using a 0.2 micron filter, to remove impurities and contaminants.

An embodiment, therefore, includes a pharmaceutical composition comprising a compound of formula (I), or a stereoisomer or pharmaceutically acceptable salt thereof. In a further embodiment includes a pharmaceutical composition comprising a compound of formula (I), or a stereoisomer or pharmaceutically acceptable salt thereof, together with a pharmaceutically acceptable carrier or excipient.

The following example A and B illustrate typical compositions of the present invention, but serve merely as representative thereof.

Example A

A compound of formula (I) can be used in a manner known per se as the active ingredient for the production of tablets of the following composition:

|  | Per tablet |
|---|---|
| Active ingredient | 200 mg |
| Microcrystalline cellulose | 155 mg |
| Corn starch | 25 mg |
| Talc | 25 mg |
| Hydroxypropylmethylcellulose | 20 mg |
|  | 425 mg |

Example B

A compound of formula (I) can be used in a manner known per se as the active ingredient for the production of capsules of the following composition:

|  | Per capsule |
|---|---|
| Active ingredient | 100.0 mg |
| Corn starch | 20.0 mg |
| Lactose | 95.0 mg |
| Talc | 4.5 mg |
| Magnesium stearate | 0.5 mg |
|  | 220.0 mg |

Indications and Methods of Treatment

The compounds of the invention can inhibit HBsAg production or secretion and inhibit HBV gene expression. Accordingly, the compounds of the invention are useful for the treatment or prophylaxis of HBV infection.

The invention relates to the use of a compound of formula (I) for the inhibition of HBsAg production or secretion.

The invention relates to the use of a compound of formula (I) for the inhibition of HBV gene expression.

The invention relates to the use of a compound of formula (I) for the treatment or prophylaxis of HBV infection.

The use of a compound of formula (I) for the preparation of medicaments useful in the treatment or prophylaxis diseases that are related to HBV infection is an object of the invention.

The invention relates in particular to the use of a compound of formula (I) for the preparation of a medicament for the treatment or prophylaxis of HBV infection.

Another embodiment includes a method for the treatment or prophylaxis of HBV infection, which method comprises administering an effective amount of a compound of formula (I), a stereoisomer, tautomer, prodrug, conjugates or pharmaceutically acceptable salt thereof.

EXAMPLES

The invention will be more fully understood by reference to the following examples. They should not, however, be construed as limiting the scope of the invention.

Abbreviations used herein are as follows:
μL: microliter
μm: micrometer
μM: micromoles per liter
(Boc)$_2$O: di-tert-butyl dicarbonate
BSA: bovine serum albumin
DEAD: diethyl azodicarboxylate
DIPEA: N,N-diisopropylethylamine
DMAP: 4-dimethylaminopyridine
DME: 1,2-dimethoxyethane
DMF: dimethylformamide
IC$_{50}$: the half maximal inhibitory concentration
HATU: O-(7-aza-1H-benzotriazole-1-yl)-N,N,N',N'-tetramethyluronium hexafluorophosphate
HMDS: hex amethyldisilazane
LiBH$_4$: lithium borohydride
LC/MS: liquid chromatography/mass spectrometry
LiHMDS: lithium bis(trimethylsilyl)amide
M: molarity
MHz: megahertz
min: minute
mM: millimoles per liter
Me$_3$SiCl: chlorotrimethylsilane
MS (ESI): mass spectroscopy (electron spray ionization)
NaBH$_3$CN: sodium cyanotrihydroborate
nM: nanomoles per liter
NMR: nuclear magnetic resonance
obsd. observed
rt: room temperature
Pd/C: palladium on activated carbon
Pd(PPh$_3$)$_4$: tetrakis(triphenylphosphine)palladium(0)
Pd(PPh$_3$)$_2$Cl$_2$: bis(triphenylphosphine)palladium(II) chloride
Pd(dppf)Cl$_2$: [1,1'-bis(diphenylphosphino)ferrocene]dichloropalladium(II)
PPh$_3$: triphenylphosphine
PTAB: phenyltrimethylammonium tribromide
TFA: trifluoroacetic acid
δ: chemical shift
Xantphos: 4,5-bis(diphenylphosphino)-9,9-dimethylxanthene
XPhos: 2-dicyclohexylphosphino-2',4',6'-triisopropylbiphenyl
Pd(dppf)Cl$_2$.CH$_2$Cl$_2$: [1,1'-bis(diphenylphosphino)ferrocene]dichloropalladium(II), complex with dichloromethane General Experimental Conditions Intermediates and final compounds were purified by flash chromatography using one of the following instruments: i) Biotage SP1 system and the Quad 12/25 Cartridge module. ii) ISCO combi-flash chromatography instrument. Silica gel Brand and pore size: i) KP-SIL 60 Å, particle size: 40-60 μM; ii) CAS registry NO: Silica Gel: 63231-67-4, particle size: 47-60 micron silica gel; iii) ZCX from Qingdao Haiyang Chemical Co., Ltd, pore: 200-300 or 300-400.

Intermediates and final compounds were purified by preparative HPLC on reversed phase column using X Bridge™ Perp C$_{18}$ (5 μm, OBD™ 30×100 mm) column or SunFire™ Perp C$_{18}$ (5 μm, OBD™ 30×100 mm) column.

LC/MS spectra were obtained using an Acquity Ultra Performance LC-3100 Mass Detector or Acquity Ultra Performance LC-SQ Detector. Standard LC/MS conditions were as follows (running time 3 minutes):
Acidic condition: A: 0.1% formic acid in H$_2$O; B: 0.1% formic acid in acetonitrile;
Basic condition: A: 0.05% NH$_3$—H$_2$O in H$_2$O; B: acetonitrile;
Neutral condition: A: H$_2$O; B: acetonitrile.

Mass spectra (MS): generally only ions which indicate the parent mass are reported, and unless otherwise stated the mass ion quoted is the positive mass ion (M+H)$^+$.

The microwave assisted reactions were carried out in a Biotage Initiator Sixty or CEM Discover.

NMR Spectra were obtained using Bruker Avance 400 MHz.

All reactions involving air-sensitive reagents were performed under an argon atmosphere. Reagents were used as received from commercial suppliers without further purification unless otherwise noted.

PREPARATIVE EXAMPLES

Example 1

9-Benzyloxy-10-methoxy-6-(2-methoxy-1,1-dimethyl-ethyl)-2-oxo-6,7-dihydrobenzo[a]quinolizine-3-carboxylic acid

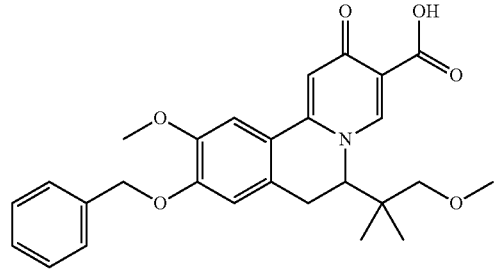 [SMILES: COCC(C)(C)C1Cc2cc(OCc3ccccc3)c(OC)cc2-c2cc(=O)c(C(=O)O)cn21]

Step 1: Preparation of 4-hydroxy-3,3-dimethyl-butan-2-one

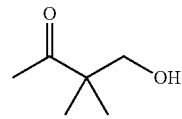

To a mixture of 3-methylbutan-2-one (400 g, 4.64 mol) in TFA (720 mL) was added paraformaldehyde (139.2 g, 4.64 mol). The resulting mixture was stirred at 80° C. for 7 h. To this mixture was added NaHCO$_3$ aqueous solution (20 L) and the whole mixture was stirred at 25° C. for 12 h. The reaction was conducted at 400 g scale three times in parallel. The combined reaction mixtures were extracted with DCM (7.5 L) 10 times, and the organic layers were combined, dried over anhydrous Na$_2$SO$_4$ and concentrated. The residue was purified by column chromatography to give 4-hydroxy-3,3-dimethyl-butan-2-one (1200 g).

Step 2: Preparation of 4-methoxy-3,3-dimethyl-butan-2-one

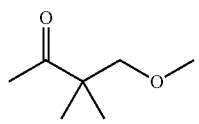

To a mixture of 4-hydroxy-3,3-dimethyl-butan-2-one (150 g, 1.3 mol) and dimethylsulfate (220 g, 1.75 mol) was added 20 N NaOH aqueous solution (88 mL, 1.75 mol) at 40° C. The mixture was stirred at 40° C. for 16 h. The reaction was conducted at 150 g scale 8 times in parallel. The combined mixtures were quenched with water (8 L), and then extracted with methyl tertiary-butyl ether (16 L). The organic layer was washed with water (4 L) 10 times, dried over anhydrous Na$_2$SO$_4$ and concentrated to give 4-methoxy-3,3-dimethyl-butan-2-one (543 g) as a yellow oil.

Step 3: Preparation of 2-benzyloxy-4-bromo-1-methoxy-benzene

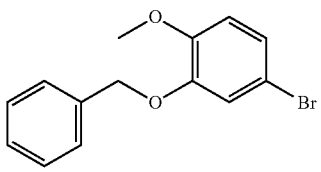 [SMILES: COc1ccc(Br)cc1OCc1ccccc1]

A 2 L round-bottomed flask was charged with 5-bromo-2-methoxyphenol (40.6 g, 0.2 mol, Accela), benzyl bromide (39.3 g, 0.23 mol), K$_2$CO$_3$ (55.2 g, 0.4 mol) and acetonitrile (0.5 L). The resulting mixture was stirred at 80° C. for 10 h. After being cooled to rt, the mixture was filtered and the filtrate was concentrated under reduced pressure to give 2-benzyloxy-4-bromo-1-methoxy-benzen as a white solid (52 g) which was used in the next step without further purification.

Step 4: Preparation of 1-(3-benzyloxy-4-methoxy-phenyl)-4-methoxy-3,3-dimethyl-butan-2-one

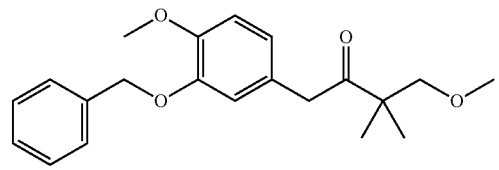 [SMILES: COCC(C)(C)C(=O)Cc1ccc(OC)c(OCc2ccccc2)c1]

To a solution of 2-benzyloxy-4-bromo-1-methoxy-benzene (14.6 g, 0.05 mol) in 1,4-dioxane (150 mL) was added 4-methoxy-3,3-dimethyl-butan-2-one (13 g, 0.1 mol, prepared from step 2), Pd(OAc)$_2$ (0.17 g, 0.75 mmol), Xantphos (0.87 g, 1.5 mmol) and LiHMDS (1.3 M in THF, 115 mL, 0.15 mol, TCI). The resulting mixture was stirred for 6 h at 70° C. under argon atmosphere. After being cooled to rt, the suspension was poured into ice water and acidified to pH=3 with 2 M hydrochloride acid. The mixture was extracted with ethyl acetate (300 mL) 2 times. The combined organic layers were washed with water (200 mL) and brine, dried over anhydrous Na$_2$SO$_4$ and concentrated to give 1-(3-benzyloxy-4-methoxy-phenyl)-4-methoxy-3,3-dimethyl-butan-2-one (15 g) as a red oil.

Step 5: Preparation of 1-(3-benzyloxy-4-methoxy-phenyl)-4-methoxy-3,3-dimethyl-butan-2-amine

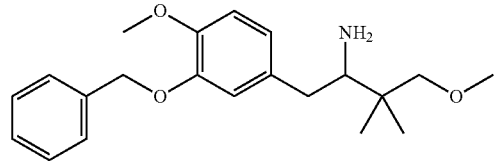 [SMILES: COCC(C)(C)C(N)Cc1ccc(OC)c(OCc2ccccc2)c1]

To a solution of 1-(3-benzyloxy-4-methoxy-phenyl)-4-methoxy-3,3-dimethyl-butan-2-one (15 g, 45 mmol) in methanol (200 mL) was added ammonium acetate (34.5 g, 0.45 mol) and sodium cyanoborohydride (5.6 g, 90 mmol). The resulting mixture was stirred for 12 h at room temperature. The reaction was quenched with water, and then to the mixture 2.0 M NaOH aqueous solution (200 mL) was added. The resulting mixture was stirred for 1 h, and extracted with ethyl acetate (300 mL) 2 times. The combined organic layers were washed with water (200 mL) 2 times and brine, dried over anhydrous Na$_2$SO$_4$ and concentrated to give 1-(3-benzyloxy-4-methoxy-phenyl)-4-methoxy-3,3-dimethyl-butan-2-amine (12 g) as a yellow oil which was used in the next step without purification.

Step 6: Preparation of N-[1-[(3-benzyloxy-4-methoxy-phenyl)methyl]-3-methoxy-2,2-dimethyl-propyl]formamide

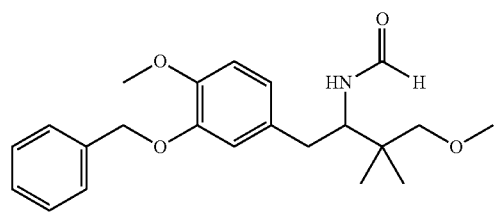 [SMILES: COCC(C)(C)C(Cc1ccc(OC)c(OCc2ccccc2)c1)NC=O]

A mixture of 1-(3-benzyloxy-4-methoxy-phenyl)-4-methoxy-3,3-dimethyl-butan-2-amine (9 g, 26 mmol) and formic acid (3.6 g, 78 mmol) in 1,4-dioxane (100 mL) was refluxed for 22 h, and then concentrated under reduced pressure. The residue was dissolved in ethyl acetate (250 mL). The solution was washed with water (100 mL) 2 times and brine, dried over anhydrous Na$_2$SO$_4$ and concentrated to give N-[1-[(3-benzyloxy-4-methoxy-phenyl)methyl]-3-methoxy-2,2-dimethyl-propyl]formamide (8.9 g).

Step 7: Preparation of 6-benzyloxy-7-methoxy-3-(2-methoxy-1,1-dimethyl-ethyl)-3,4-dihydroisoquinoline

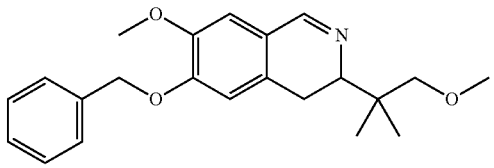 [SMILES: COCC(C)(C)C1Cc2cc(OCc3ccccc3)c(OC)cc2C=N1]

To a solution of N-[1-[(3-benzyloxy-4-methoxy-phenyl)methyl]-3-methoxy-2,2-dimethyl-propyl]formamide (8.9 g, 24 mmol) in acetonitrile (100 mL) was added POCl₃ (7.4 g, 48 mmol, Sinopharm Chemical) dropwise at 0-5° C. The resulting mixture was refluxed for 2 h. After being cooled to rt, the mixture was concentrated. Then to the residue, ethyl acetate (100 mL) was added, followed by addition of ammonia water to adjust the pH of the aqueous solution to around 11. The mixture was extracted with ethyl acetate (200 mL) 2 times, and the combined organic layers were concentrated to give 6-benzyloxy-7-methoxy-3-(2-methoxy-1,1-dimethyl-ethyl)-3,4-dihydroisoquinoline (8 g).

Step 8: Preparation of ethyl 9-benzyloxy-10-methoxy-6-(2-methoxy-1,1-dimethyl-ethyl)-2-oxo-1,6,7,11b-tetrahydrobenzo[a]quinolizine-3-carboxylate

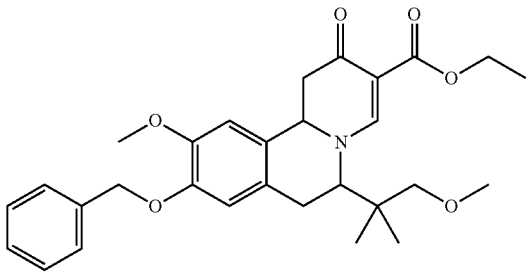 [SMILES: CCOC(=O)C1=CN2C(CC1=O)c1cc(OC)c(OCc3ccccc3)cc1CC2C(C)(C)COC]

A mixture of 6-benzyloxy-7-methoxy-3-(2-methoxy-1,1-dimethyl-ethyl)-3,4-dihydroisoquinoline (8 g, 22.6 mmol) and ethyl 2-(ethoxymethylene)-3-oxo-butanoate (12.6 g, 67.8 mmol, General Material Company Limited) in ethanol (100 mL) was refluxed overnight. The mixture was concentrated to give crude ethyl 9-benzyloxy-10-methoxy-6-(2-methoxy-1,1-dimethyl-ethyl)-2-oxo-1,6,7,11b-tetrahydrobenzo[a]quinolizine-3-carboxylate (11 g) as a dark brown oil which was used in the next step without purification.

Step 9: Preparation of ethyl 9-benzyloxy-10-methoxy-6-(2-methoxy-1,1-dimethyl-ethyl)-2-oxo-6,7-dihydrobenzo[a]quinolizine-3-carboxylate

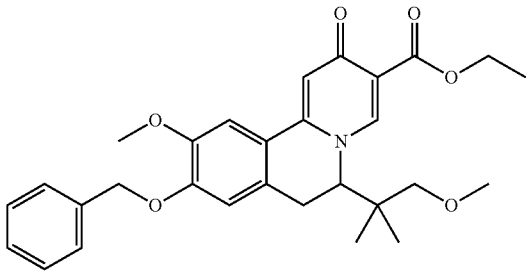 [SMILES: CCOC(=O)c1cn2c(cc1=O)-c1cc(OC)c(OCc3ccccc3)cc1CC2C(C)(C)COC]

A mixture of crude ethyl 9-benzyloxy-10-methoxy-6-(2-methoxy-1,1-dimethyl-ethyl)-2-oxo-1,6,7,11b-tetrahydrobenzo[a]quinolizine-3-carboxylate (11 g, 22 mmol) and p-chloranil (4.2 g, 16.5 mmol, TCI) in DME (100 mL) was refluxed for 2 h. After being cooled to rt, the suspension was filtered with suction. The filter cake was washed with cold DME and dried under vacuum to give ethyl 9-benzyloxy-10-methoxy-6-(2-methoxy-1,1-dimethyl-ethyl)-2-oxo-6,7-dihydrobenzo[a]quinolizine-3-carboxylate as a yellow solid (9.2 g)

Step 10: Preparation of 9-benzyloxy-10-methoxy-6-(2-methoxy-1,1-dimethyl-ethyl)-2-oxo-6,7-dihydrobenzo[a]quinolizine-3-carboxylic acid

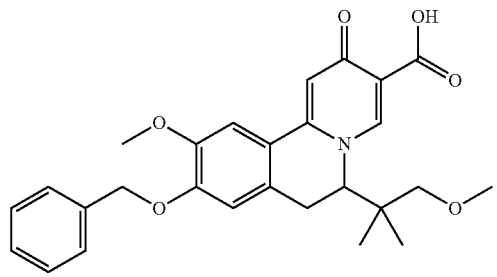 [SMILES: COCC(C)(C)C1Cc2cc(OCc3ccccc3)c(OC)cc2-c2cc(=O)c(C(=O)O)cn21]

To a solution of ethyl 9-benzyloxy-10-methoxy-6-(2-methoxy-1,1-dimethyl-ethyl)-2-oxo-6,7-dihydrobenzo[a]quinolizine-3-carboxylate (150 mg, 0.3 mmol) in THF (10 mL) and ethanol (2 mL) was added 2.0 M LiOH aqueous solution (0.75 mL) at rt. The resulting mixture was stirred for 4 h, and then acidified to pH=1-2 with 2 M hydrochloric acid. The mixture was extracted with DCM (30 mL) 2 times. The combined organic layers were washed with water and brine, dried over anhydrous Na₂SO₄ and concentrated. The residue was purified by prep-HPLC to give 9-benzyloxy-10-methoxy-6-(2-methoxy-1,1-dimethyl-ethyl)-2-oxo-6,7-dihydrobenzo[a]quinolizine-3-carboxylic acid (5 mg). $^1$H NMR (400 MHz, CDCl₃): δ 8.57-8.61 (m, 1H), 7.35-7.48 (m, 5H), 7.15-7.19 (m, 1H), 7.05-7.09 (m, 1H), 6.72-6.77 (m, 1H), 5.25 (s, 2H), 4.48-4.53 (m, 1H), 3.96 (s, 3H), 3.39-3.42 (m, 1H), 3.36 (s, 3H), 3.00-3.07 (m, 1H), 2.90 (s, 2H), 0.94 (s, 3H), 0.39 (s, 3H). MS obsd. (ESI⁺) [(M+H)⁺]: 464.

Example 2

9,10-Dimethoxy-6-(2-methoxy-1,1-dimethyl-ethyl)-2-oxo-6,7-dihydrobenzo[a]quinolizine-3-carboxylic acid

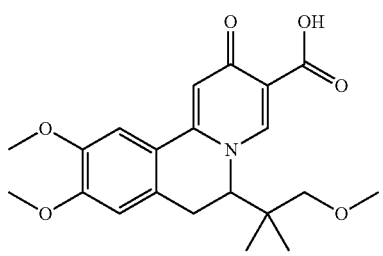

Step 1: Preparation of ethyl 9-hydroxy-10-methoxy-6-(2-methoxy-1,1-dimethyl-ethyl)-2-oxo-6,7-dihydrobenzo[a]quinolizine-3-carboxylate

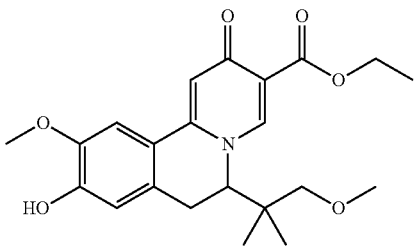 [SMILES: CCOC(=O)c1cn2c(cc1=O)-c1cc(OC)c(O)cc1CC2C(C)(C)COC]

A mixture of ethyl 9-benzyloxy-10-methoxy-6-(2-methoxy-1,1-dimethyl-ethyl)-2-oxo-6,7-dihydrobenzo[a]quinolizine-3-carboxylate (9 g, 18.3 mmol) and 10% palladium on carbon (200 mg) in ethanol (100 mL) was stirred under a balloon of hydrogen atmosphere for 12 h. The mixture was filtered through celite and the filtrate was concentrated under reduced pressure to afford ethyl 9-hydroxy-10-methoxy-6-(2-methoxy-1,1-dimethyl-ethyl)-2-oxo-6,7-dihydrobenzo[a]quinolizine-3-carboxylate (4.9 g).

Step 2: Preparation of ethyl 9,10-dimethoxy-6-(2-methoxy-1,1-dimethyl-ethyl)-2-oxo-6,7-dihydrobenzo[a]quinolizine-3-carboxylate

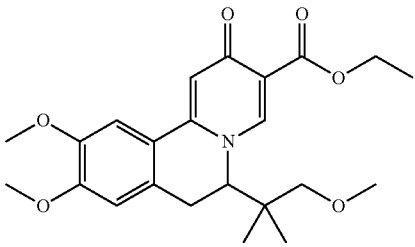 [SMILES: CCOC(=O)c1cn2c(cc1=O)-c1cc(OC)c(OC)cc1CC2C(C)(C)COC]

To a solution of ethyl 9-hydroxy-10-methoxy-6-(2-methoxy-1,1-dimethyl-ethyl)-2-oxo-6,7-dihydrobenzo[a]quinolizine-3-carboxylate (160 mg, 0.4 mmol) in DMF (5 mL) was added potassium carbonate (110 mg, 0.8 mmol) and iodomethane (114 mg, 0.8 mmol, Sinopharm Chemical). The resulting mixture was heated at 90° C. for 6 h. After being cooled to room temperature, the dark-brown mixture was poured into water (50 mL). The mixture was extracted with DCM (50 mL) 2 times. The combined organic layers were washed with brine, dried over anhydrous Na$_2$SO$_4$, and concentrated under reduced pressure to give crude ethyl 9,10-dimethoxy-6-(2-methoxy-1,1-dimethyl-ethyl)-2-oxo-6,7-dihydrobenzo[a]quinolizine-3-carboxylate (150 mg), which was used directly in the next step without further purification.

Step 3: Preparation of 9,10-dimethoxy-6-(2-methoxy-1,1-dimethyl-ethyl)-2-oxo-6,7-dihydrobenzo[a]quinolizine-3-carboxylic acid

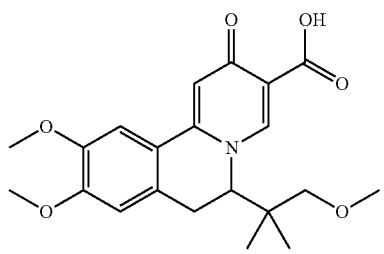

To a solution of ethyl 9,10-dimethoxy-6-(2-methoxy-1,1-dimethyl-ethyl)-2-oxo-6,7-dihydrobenzo[a]quinolizine-3-carboxylate (150 mg, 0.36 mmol) in THF (10 mL) and ethanol (2 mL) was added 2.0 M LiOH aqueous solution (0.9 mL) at rt. The resulting mixture was stirred for 4 h, and then acidified to pH=1-2 with 2 M hydrochloric acid. The mixture was extracted with DCM (30 mL) 2 times. The combined organic layers were washed with water and brine, dried over anhydrous Na$_2$SO$_4$ and concentrated to give a yellow solid, which was purified by prep-HPLC to give 9,10-dimethoxy-6-(2-methoxy-1,1-dimethyl-ethyl)-2-oxo-6,7-dihydrobenzo[a]quinolizine-3-carboxylic acid (20 mg). $^1$H NMR (400 MHz, CDCl$_3$): δ 8.59-8.65 (m, 1H), 7.13-7.19 (m, 1H), 7.05-7.10 (m, 1H), 6.71-6.77 (m, 1H), 4.53-4.59 (m, 1H), 3.97 (d, 6H), 3.42-3.51 (m, 1H), 3.38 (s, 3H), 3.09-3.18 (m, 1H), 2.90-2.97 (m, 2H), 1.01 (s, 3H), 0.45 (s, 3H). MS obsd. (ESI$^+$) [(M+H)$^+$]: 388.

Example 3

10-Methoxy-6-(2-methoxy-1,1-dimethyl-ethyl)-2-oxo-9-(2,2,2-trifluoroethoxy)-6,7-dihydrobenzo[a]quinolizine-3-carboxylic acid

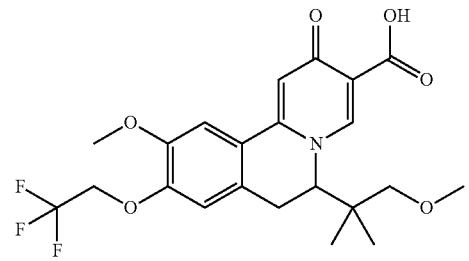 [SMILES: COCC(C)(C)C1Cc2cc(OCC(F)(F)F)c(OC)cc2-c2cc(=O)c(C(=O)O)cn21]

Step 1: Preparation of ethyl 10-methoxy-6-(2-methoxy-1,1-dimethyl-ethyl)-2-oxo-9-(2,2,2-trifluoroethoxy)-6,7-dihydrobenzo[a]quinolizine-3-carboxylate

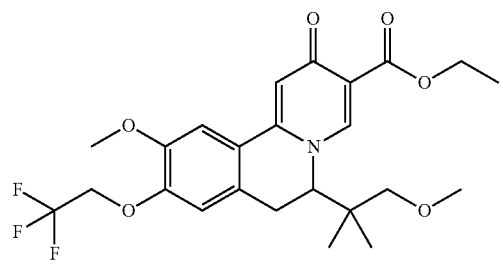 [SMILES: CCOC(=O)c1cn2c(cc1=O)-c1cc(OC)c(OCC(F)(F)F)cc1CC2C(C)(C)COC]

To a solution of ethyl 9-hydroxy-10-methoxy-6-(2-methoxy-1,1-dimethyl-ethyl)-2-oxo-6,7-dihydrobenzo[a]quinolizine-3-carboxylate (160 mg, 0.4 mmol) in DMF (5 mL) was added potassium carbonate (110 mg, 0.8 mmol) and 2-iodo-1,1,1-trifluoroethane (168 mg, 0.8 mmol, Accela). The resulting mixture was heated at 90° C. for 6 h. After being cooled to room temperature, the dark-brown mixture was poured into water (50 mL) and the aqueous solution was extracted with DCM (50 mL) 2 times. The organic layers were combined and washed with brine, dried over anhydrous Na$_2$SO$_4$, and concentrated under reduced pressure to give crude ethyl 10-methoxy-6-(2-methoxy-1,1-dimethyl-ethyl)-2-oxo-9-(2,2,2-trifluoroethoxy)-6,7-dihydrobenzo[a]quinolizine-3-carboxylate (175 mg), which was used in the next step without purification.

Step 2: Preparation of 10-methoxy-6-(2-methoxy-1,1-dimethyl-ethyl)-2-oxo-9-(2,2,2-trifluoroethoxy)-6,7-dihydrobenzo[a]quinolizine-3-carboxylic acid

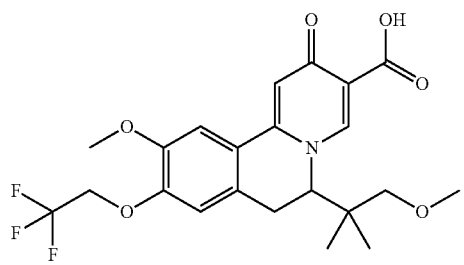 [SMILES: COCC(C)(C)C1Cc2cc(OCC(F)(F)F)c(OC)cc2-c2cc(=O)c(C(=O)O)cn21]

To a solution of ethyl 10-methoxy-6-(2-methoxy-1,1-dimethyl-ethyl)-2-oxo-9-(2,2,2-trifluoroethoxy)-6,7-dihydrobenzo[a]quinolizine-3-carboxylate (175 mg, 0.36 mmol) in THF (10 mL) and ethanol (2 mL) was added 2.0 M LiOH aqueous solution (0.9 mL) at rt. The resulting mixture was stirred for 4 h, and then acidified to pH=1-2 with 2 M hydrochloric acid. The mixture was extracted with DCM (30 mL) 2 times. The combined organic layers were washed with water and brine, dried over anhydrous Na$_2$SO$_4$ and concentrated. The residue was purified by prep-HPLC to give 10-methoxy-6-(2-methoxy-1,1-dimethyl-ethyl)-2-oxo-9-(2,2,2-trifluoroethoxy)-6,7-dihydrobenzo[a]quinolizine-3-carboxylic acid (8 mg). $^1$H NMR (400 MHz, CDCl$_3$): δ 8.62-8.65 (m, 1H), 7.22-7.25 (m, 1H), 7.09-7.13 (m, 1H), 6.86-6.90 (m, 1H), 4.46-4.58 (m, 3H), 3.97 (s, 3H), 3.40-3.47 (m, 1H), 3.38 (s, 3H), 3.09-3.17 (m, 1H), 2.94 (s, 2H), 1.00 (s, 3H), 0.44 (s, 3H). MS obsd. (ESI$^+$) [(M+H)$^+$]: 456.

Example 4

10-Methoxy-6-(2-methoxy-1,1-dimethyl-ethyl)-9-(3-morpholinopropoxy)-2-oxo-6,7-dihydrobenzo[a]quinolizine-3-carboxylic acid

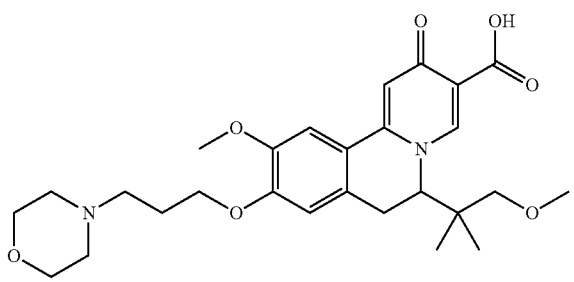 [SMILES: COCC(C)(C)C1Cc2cc(OCCCN3CCOCC3)c(OC)cc2-c2cc(=O)c(C(=O)O)cn21]

Step 1: Preparation of ethyl 10-methoxy-6-(2-methoxy-1,1-dimethyl-ethyl)-9-(3-morpholinopropoxy)-2-oxo-6,7-dihydrobenzo[a]quinolizine-3-carboxylate

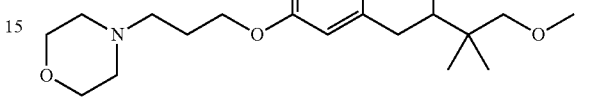

To a solution of ethyl 9-hydroxy-10-methoxy-6-(2-methoxy-1,1-dimethyl-ethyl)-2-oxo-6,7-dihydrobenzo[a]quinolizine-3-carboxylate (160 mg, 0.4 mmol) in DMF (5 mL) was added potassium carbonate (165 mg, 1.2 mmol) and 4-(3-chloropropyl) morpholine hydrochloride (130 mg, 0.8 mmol, Accela). The resulting mixture was heated at 90° C. for 6 h. After being cooled to room temperature, the dark-brown mixture was poured into water (50 mL) and the aqueous solution was extracted with DCM (50 mL) 2 times. The organic layers were combined and washed with brine, dried over anhydrous Na$_2$SO$_4$, and concentrated under reduced pressure to give crude ethyl 10-methoxy-6-(2-methoxy-1,1-dimethyl-ethyl)-9-(3-morpholinopropoxy)-2-oxo-6,7-dihydrobenzo[a]quinolizine-3-carboxylate (190 mg), which was used in the next step without further purification.

Step 2: Preparation of 10-methoxy-6-(2-methoxy-1,1-dimethyl-ethyl)-9-(3-morpholinopropoxy)-2-oxo-6,7-dihydrobenzo[a]quinolizine-3-carboxylic acid To a solution of ethyl 10-methoxy-6-(2-methoxy-1,1-dimethyl-ethyl)-9-(3-morpholinopropoxy)-2-oxo-6,7-dihydrobenzo[a]quinolizine-3-carboxylate (190 mg, 0.36 mmol) in THF (10 mL) and ethanol (2 mL) was added 2.0 M LiOH aqueous solution (0.9 mL) at rt. The resulting mixture was stirred for 4 h, and then acidified to pH=5-6 with 2 M hydrochloric acid. The mixture was extracted with DCM (30 mL) 2 times. The combined organic layers were washed with water and brine, dried over anhydrous Na$_2$SO$_4$ and concentrated to give a yellow solid, which was purified by prep-HPLC to give 10-methoxy-6-(2-methoxy-1,1-dimethyl-ethyl)-9-(3-morpholinopropoxy)-2-oxo-6,7-dihydrobenzo[a]quinolizine-3-carboxylic acid (25 mg). ¹H NMR (400 MHz, CDCl₃): δ 8.60 (s, 1H), 7.15 (s, 1H), 7.06 (s, 1H), 6.72-6.81 (m, 1H), 4.48-4.58 (m, 1H), 4.12-4.26 (m, 2H), 3.93 (s, 3H), 3.79 (br. s., 4H), 3.40-3.48 (m, 1H), 3.37 (s, 3H), 3.07-3.16 (m, 1H), 2.93 (s, 2H), 2.66 (br. s., 2H), 2.60 (br. s., 4H), 2.13-2.21 (m, 2H), 1.00 (s, 3H), 0.44 (s, 3H). MS obsd. (ESI⁺) [(M+H)⁺]: 501.

Example 5

9-(6-Hydroxyhexoxy)-10-methoxy-6-(2-methoxy-1,1-dimethyl-ethyl)-2-oxo-6,7-dihydrobenzo[a]quinolizine-3-carboxylic acid

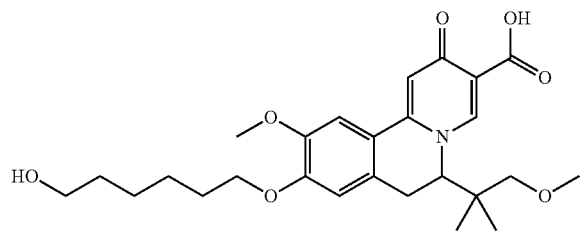 [SMILES: COCC(C)(C)C1Cc2cc(OCCCCCCO)c(OC)cc2-c2cc(=O)c(C(=O)O)cn21]

Step 1: Preparation of ethyl 9-(6-hydroxyhexoxy)-10-methoxy-6-(2-methoxy-1,1-dimethyl-ethyl)-2-oxo-6,7-dihydrobenzo[a]quinolizine-3-carboxylate

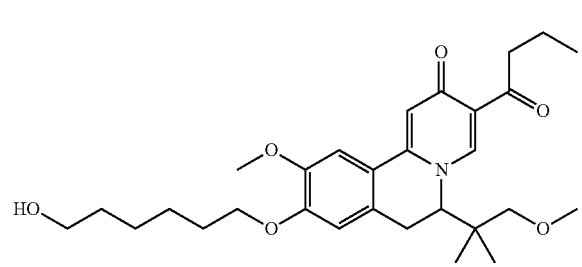 [SMILES: CCCC(=O)c1cn2c(cc1=O)-c1cc(OC)c(OCCCCCCO)cc1CC2C(C)(C)COC]

To a solution of ethyl 9-hydroxy-10-methoxy-6-(2-methoxy-1,1-dimethyl-ethyl)-2-oxo-6,7-dihydrobenzo[a]quinolizine-3-carboxylate (160 mg, 0.4 mmol) in DMF (5 mL) was added potassium carbonate (110 mg, 0.8 mmol) and 6-bromohexan-1-ol (145 mg, 0.8 mmol, Accela). The resulting mixture was heated at 90° C. for 6 h. After being cooled to room temperature, the dark-brown mixture was poured into water (50 mL) and the aqueous solution was extracted with DCM (50 mL) 2 times. The organic layers were combined and washed with brine, dried over anhydrous Na₂SO₄, and concentrated under reduced pressure to give crude ethyl 9-(6-hydroxyhexoxy)-10-methoxy-6-(2-methoxy-1,1-dimethyl-ethyl)-2-oxo-6,7-dihydrobenzo[a]quinolizine-3-carboxylate (180 mg), which was used in the next step without further purification.

Step 2: Preparation of 9-(6-hydroxyhexoxy)-10-methoxy-6-(2-methoxy-1,1-dimethyl-ethyl)-2-oxo-6,7-dihydrobenzo[a]quinolizine-3-carboxylic acid

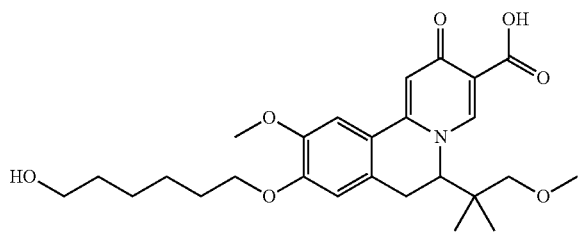 [SMILES: COCC(C)(C)C1Cc2cc(OCCCCCCO)c(OC)cc2-c2cc(=O)c(C(=O)O)cn21]

To a solution of ethyl 9-(6-hydroxyhexoxy)-10-methoxy-6-(2-methoxy-1,1-dimethyl-ethyl)-2-oxo-6,7-dihydrobenzo[a]quinolizine-3-carboxylate (180 mg, 0.36 mmol) in THF (10 mL) and ethanol (2 mL) was added 2.0 M LiOH aqueous solution (0.9 mL) at rt. The resulting mixture was stirred for 4 h, and then acidified to pH=1-2 with 2 M hydrochloric acid. The mixture was extracted with DCM (30 mL) 2 times. The combined organic layers were washed with water and brine, dried over anhydrous Na₂SO₄ and concentrated. The residue was purified by prep-HPLC to give 9-(6-hydroxyhexoxy)-10-methoxy-6-(2-methoxy-1,1-dimethyl-ethyl)-2-oxo-6,7-dihydrobenzo[a]quinolizine-3-carboxylic acid (18 mg). ¹H NMR (400 MHz, CDCl₃): δ 8.58-8.62 (m, 1H), 7.11-7.17 (m, 1H), 7.04-7.08 (m, 1H), 6.70-6.75 (m, 1H), 4.51-4.57 (m, 1H), 4.05-4.16 (m, 2H), 3.94 (s, 3H), 3.69 (s, 2H), 3.40-3.47 (m, 1H), 3.37 (s, 3H), 3.08-3.15 (m, 1H), 2.93 (s, 2H), 1.89-1.97 (m, 2H), 1.63 (br. s., 2H), 1.50-1.59 (m, 4H), 1.00 (s, 3H), 0.44 (s, 3H). MS obsd. (ESI⁺) [(M+H)⁺]: 474.

Example 6

9-(3-Hydroxypropoxy)-10-methoxy-6-(2-methoxy-1,1-dimethyl-ethyl)-2-oxo-6,7-dihydrobenzo[a]quinolizine-3-carboxylic acid

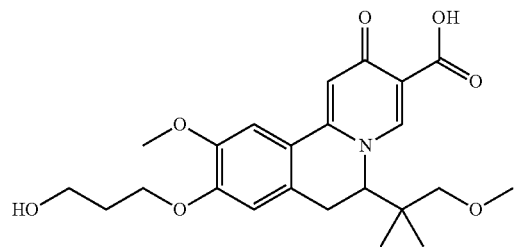 [SMILES: COCC(C)(C)C1Cc2cc(OCCCO)c(OC)cc2-c2cc(=O)c(C(=O)O)cn21]

Step 1: Preparation of ethyl 9-(3-hydroxypropoxy)-10-methoxy-6-(2-methoxy-1,1-dimethyl-ethyl)-2-oxo-6,7-dihydrobenzo[a]quinolizine-3-carboxylate

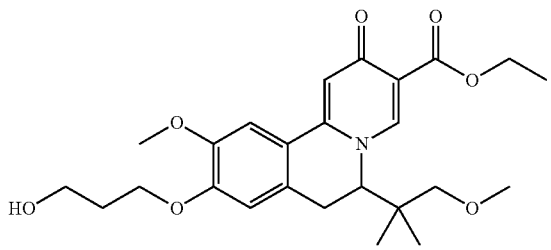 [SMILES: CCOC(=O)c1cn2c(cc1=O)-c1cc(OC)c(OCCCO)cc1CC2C(C)(C)COC]

To a solution of ethyl 9-hydroxy-10-methoxy-6-(2-methoxy-1,1-dimethyl-ethyl)-2-oxo-6,7-dihydrobenzo[a]

quinolizine-3-carboxylate (160 mg, 0.4 mmol) in DMF (5 mL) was added potassium carbonate (110 mg, 0.8 mmol) and 3-iodopropan-1-ol (150 mg, 0.8 mmol, Accela). The resulting mixture was heated at 90° C. for 6 h. After being cooled to room temperature, the dark-brown mixture was poured into water (50 mL). The resulting mixture was extracted with DCM (50 mL) 2 times. The organic layers were combined and washed with brine, dried over anhydrous $Na_2SO_4$, and concentrated under reduced pressure to give crude ethyl 9-(3-hydroxypropoxy)-10-methoxy-6-(2-methoxy-1,1-dimethyl-ethyl)-2-oxo-6,7-dihydrobenzo[a]quinolizine-3-carboxylate (165 mg), which was used in the next step without further purification.

Step 2: Preparation of 9-(3-hydroxypropoxy)-10-methoxy-6-(2-methoxy-1,1-dimethyl-ethyl)-2-oxo-6,7-dihydrobenzo[a]quinolizine-3-carboxylic acid

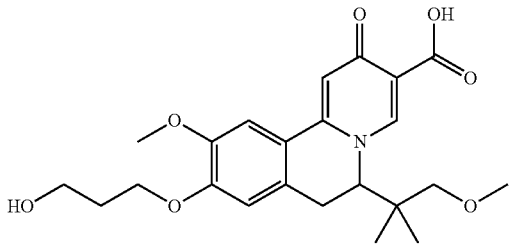

To a solution of ethyl 9-(3-hydroxypropoxy)-10-methoxy-6-(2-methoxy-1,1-dimethyl-ethyl)-2-oxo-6,7-dihydrobenzo[a]quinolizine-3-carboxylate (165 mg, 0.36 mmol) in THF (10 mL) and ethanol (2 mL) was added 2.0 M LiOH aqueous solution (0.9 mL) at rt. The resulting mixture was stirred for 4 h, and then acidified to pH=1-2 with 2 M hydrochloric acid. The mixture was extracted with DCM (30 mL) 2 times. The combined organic layers were washed with water and brine, dried over anhydrous $Na_2SO_4$ and concentrated to give a yellow solid, which was purified by prep-HPLC to give 9-(3-hydroxypropoxy)-10-methoxy-6-(2-methoxy-1,1-dimethyl-ethyl)-2-oxo-6,7-dihydrobenzo[a]quinolizine-3-carboxylic acid (5 mg). $^1H$ NMR (400 MHz, $CDCl_3$): δ 8.58-8.63 (m, 1H), 7.13-7.19 (m, 1H), 7.03-7.09 (m, 1H), 6.74-6.79 (m, 1H), 4.51-4.56 (m, 1H), 4.23-4.33 (m, 2H), 3.93 (s, 5H), 3.41-3.47 (m, 1H), 3.39-3.47 (m, 1H), 3.38 (s, 3H), 3.07-3.16 (m, 1H), 2.94 (s, 2H), 2.12-2.21 (m, 2H), 1.00 (s, 3H), 0.45 (s, 3H). MS obsd. ($ESI^+$) $[(M+H)^+]$: 432.

Example 7

9-(3-Hydroxy-2,2-dimethyl-propoxy)-10-methoxy-6-(2-methoxy-1,1-dimethyl-ethyl)-2-oxo-6,7-dihydrobenzo[a]quinolizine-3-carboxylic acid

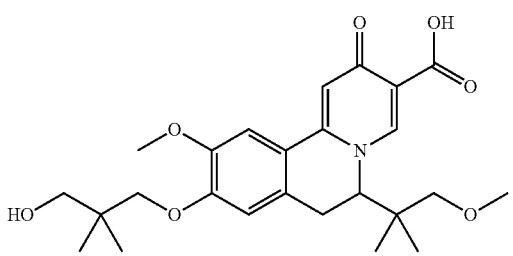 [SMILES: COCC(C)(C)C1Cc2cc(OCC(C)(C)CO)c(OC)cc2-c2cc(=O)c(C(=O)O)cn21]

Step 1: Preparation of ethyl 9-(3-hydroxy-2,2-dimethyl-propoxy)-10-methoxy-6-(2-methoxy-1,1-dimethyl-ethyl)-2-oxo-6,7-dihydrobenzo[a]quinolizine-3-carboxylate

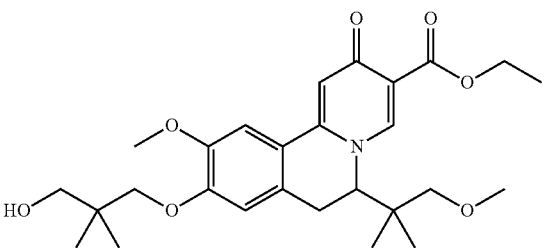 [SMILES: CCOC(=O)c1cn2c(cc1=O)-c1cc(OC)c(OCC(C)(C)CO)cc1CC2C(C)(C)COC]

To a solution of ethyl 9-hydroxy-10-methoxy-6-(2-methoxy-1,1-dimethyl-ethyl)-2-oxo-6,7-dihydrobenzo[a]quinolizine-3-carboxylate (160 mg, 0.4 mmol) in DMF (5 mL) was added potassium carbonate (110 mg, 0.8 mmol) and 3-bromo-2,2-dimethyl-propan-1-ol (133 mg, 0.8 mmol, TCI). The resulting mixture was heated at 90° C. for 6 h. After being cooled to room temperature, the dark-brown mixture was poured into water (50 mL). The resulting mixture was extracted with DCM (50 mL) 2 times. The organic layers were combined and washed with brine, dried over anhydrous $Na_2SO_4$, and concentrated under reduced pressure to give crude ethyl 9-(3-hydroxy-2,2-dimethyl-propoxy)-10-methoxy-6-(2-methoxy-1,1-dimethyl-ethyl)-2-oxo-6,7-dihydrobenzo[a]quinolizine-3-carboxylate (174 mg), which was used in the next step without further purification Step 2: Preparation of 9-(3-hydroxy-2,2-dimethyl-propoxy)-10-methoxy-6-(2-methoxy-1,1-dimethyl-ethyl)-2-oxo-6,7-dihydrobenzo[a]quinolizine-3-carboxylic acid

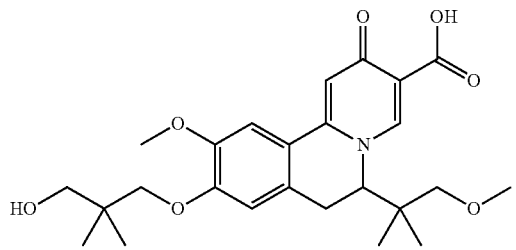 [SMILES: COCC(C)(C)C1Cc2cc(OCC(C)(C)CO)c(OC)cc2-c2cc(=O)c(C(=O)O)cn21]

To a solution of ethyl 9-(3-hydroxy-2,2-dimethyl-propoxy)-10-methoxy-6-(2-methoxy-1,1-dimethyl-ethyl)-2-oxo-6,7-dihydrobenzo[a]quinolizine-3-carboxylate (174 mg, 0.36 mmol) in THF (10 mL) and ethanol (2 mL) was added 2.0 M LiOH aqueous solution (0.9 mL) at rt. The resulting mixture was stirred for 4 h, and then acidified to pH=1-2 with 2 M hydrochloric acid. The mixture was extracted with DCM (30 mL) 2 times. The combined organic layers were washed with water and brine, dried over anhydrous $Na_2SO_4$ and concentrated to give a yellow solid, which was purified by prep-HPLC to give 9-(3-hydroxy-2,2-dimethyl-propoxy)-10-methoxy-6-(2-methoxy-1,1-dimethyl-ethyl)-2-oxo-6,7-dihydrobenzo[a]quinolizine-3-carboxylic acid (18 mg). $^1H$ NMR (400 MHz, $CDCl_3$): δ 8.59-8.64 (m, 1H), 7.13-7.17 (m, 1H), 7.06-7.11 (m, 1H), 6.72-6.77 (m, 1H), 4.51-4.57 (m, 1H), 3.92 (s, 5H), 3.61 (s, 2H), 3.40-3.48 (m, 1H), 3.33-3.38 (m, 3H), 3.08-3.15 (m, 1H), 2.90-2.96 (m, 2H), 1.10 (d, 6H), 1.01 (s, 3H), 0.45 (s, 3H). MS obsd. ($ESI^+$) $[(M+H)^+]$: 460.

Example 8

9-(2-Ethoxyethoxy)-10-methoxy-6-(2-methoxy-1,1-dimethyl-ethyl)-2-oxo-6,7-dihydrobenzo[a]quinolizine-3-carboxylic acid

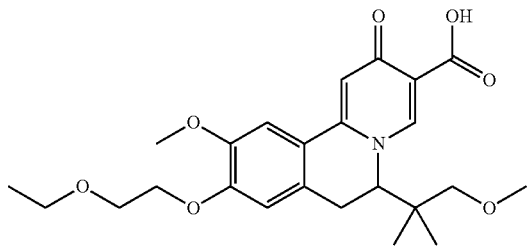 [SMILES: CCOCCOc1cc2c(cc1OC)-c1cc(=O)c(C(=O)O)cn1C(C(C)(C)COC)C2]

Step 1: Preparation of ethyl 9-(2-ethoxyethoxy)-10-methoxy-6-(2-methoxy-1,1-dimethyl-ethyl)-2-oxo-6,7-dihydrobenzo[a]quinolizine-3-carboxylate

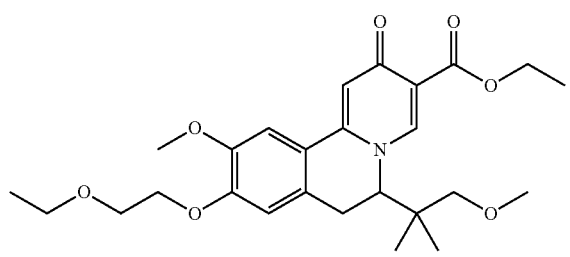

To a solution of ethyl 9-hydroxy-10-methoxy-6-(2-methoxy-1,1-dimethyl-ethyl)-2-oxo-6,7-dihydrobenzo[a]quinolizine-3-carboxylate (160 mg, 0.4 mmol) in DMF (5 mL) was added potassium carbonate (110 mg, 0.8 mmol) and 1-bromo-2-ethoxy-ethane (122 mg, 0.8 mmol, Aldrich). The resulting mixture was heated at 90° C. for 6 h. After being cooled to room temperature, the dark-brown mixture was poured into water (50 mL). The resulting mixture was extracted with DCM (50 mL) 2 times. The combined organic layers were washed with brine, dried over anhydrous $Na_2SO_4$, and concentrated under reduced pressure to give crude ethyl 9-(2-ethoxyethoxy)-10-methoxy-6-(2-methoxy-1,1-dimethyl-ethyl)-2-oxo-6,7-dihydrobenzo[a]quinolizine-3-carboxylate (170 mg), which was used in the next step without further purification.

Step 2: Preparation of 9-(2-ethoxyethoxy)-10-methoxy-6-(2-methoxy-1,1-dimethyl-ethyl)-2-oxo-6,7-dihydrobenzo[a]quinolizine-3-carboxylic acid

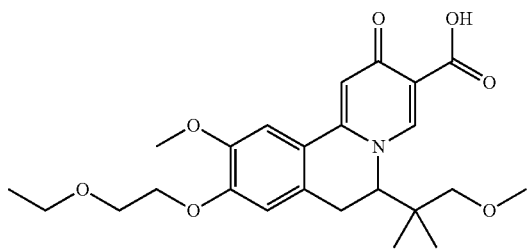 [SMILES: CCOCCOc1cc2c(cc1OC)-c1cc(=O)c(C(=O)O)cn1C(C(C)(C)COC)C2]

To a solution of ethyl 9-(2-ethoxyethoxy)-10-methoxy-6-(2-methoxy-1,1-dimethyl-ethyl)-2-oxo-6,7-dihydrobenzo[a]quinolizine-3-carboxylate (170 mg, 0.36 mmol) in THF (10 mL) and ethanol (2 mL) was added 2.0 M LiOH aqueous solution (0.9 mL) at rt. The resulting mixture was stirred for 4 h, and then acidified to pH=1-2 with 2 M hydrochloric acid. The mixture was extracted with DCM (30 mL) 2 times. The combined organic layers were washed with water and brine, dried over anhydrous $Na_2SO_4$ and concentrated to give a yellow solid, which was purified by prep-HPLC to give 9-(2-ethoxyethoxy)-10-methoxy-6-(2-methoxy-1,1-dimethyl-ethyl)-2-oxo-6,7-dihydrobenzo[a]quinolizine-3-carboxylic acid (30 mg). $^1$H NMR (400 MHz, $CDCl_3$): δ 8.60-8.65 (m, 1H), 7.14-7.18 (m, 1H), 7.07-7.12 (m, 1H), 6.79-6.85 (m, 1H), 4.52-4.58 (m, 1H), 4.22-4.33 (m, 2H), 3.94 (s, 3H), 3.85-3.91 (m, 2H), 3.60-3.68 (m, 2H), 3.40-3.48 (m, 1H), 3.37 (s, 3H), 3.07-3.15 (m, 1H), 2.91-2.96 (m, 2H), 1.26 (s, 3H), 1.00 (s, 3H), 0.44 (s, 3H). MS obsd. $(ESI^+)$ $[(M+H)^+]$: 446.

Example 9

9-(Cyclopropylmethoxy)-10-methoxy-6-(2-methoxy-1,1-dimethyl-ethyl)-2-oxo-6,7-dihydrobenzo[a]quinolizine-3-carboxylic acid

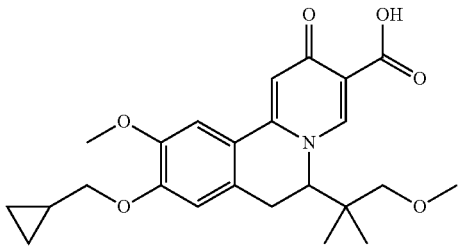 [SMILES: COCC(C)(C)C1Cc2cc(OCC3CC3)c(OC)cc2-c2cc(=O)c(C(=O)O)cn21]

Step 1: Preparation of ethyl 9-(cyclopropylmethoxy)-10-methoxy-6-(2-methoxy-1,1-dimethyl-ethyl)-2-oxo-6,7-dihydrobenzo[a]quinolizine-3-carboxylate

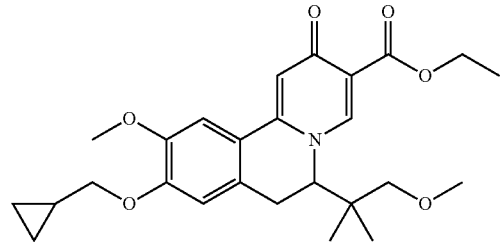 [SMILES: CCOC(=O)c1cn2c(cc1=O)-c1cc(OC)c(OCC3CC3)cc1CC2C(C)(C)COC]

To a solution of ethyl 9-hydroxy-10-methoxy-6-(2-methoxy-1,1-dimethyl-ethyl)-2-oxo-6,7-dihydrobenzo[a]quinolizine-3-carboxylate (160 mg, 0.4 mmol) in DMF (5 mL) was added potassium carbonate (110 mg, 0.8 mmol) and bromomethylcyclopropane (108 mg, 0.8 mmol, TCI). The resulting mixture was heated at 90° C. for 6 h. After being cooled to room temperature, the dark-brown mixture was poured into water (50 mL). The resulting mixture was extracted with DCM (50 mL) 2 times. The combined organic layers were washed with brine, dried over anhydrous $Na_2SO_4$, and concentrated under reduced pressure to give crude ethyl 9-(cyclopropylmethoxy)-10-methoxy-6-(2-methoxy-1,1-dimethyl-ethyl)-2-oxo-6,7-dihydrobenzo[a]quinolizine-3-carboxylate (165 mg), which was used directly in the next step without further purification.

Step 2: Preparation of 9-(cyclopropylmethoxy)-10-methoxy-6-(2-methoxy-1,1-dimethyl-ethyl)-2-oxo-6,7-dihydrobenzo[a]quinolizine-3-carboxylic acid

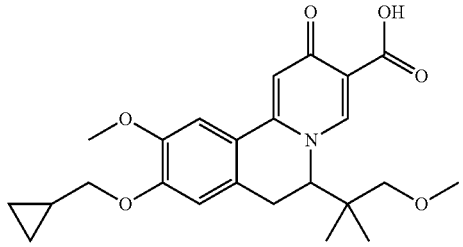 [SMILES: COCC(C)(C)C1Cc2cc(OCC3CC3)c(OC)cc2-c2cc(=O)c(C(=O)O)cn21]

To a solution of ethyl 9-(cyclopropylmethoxy)-10-methoxy-6-(2-methoxy-1,1-dimethyl-ethyl)-2-oxo-6,7-dihydrobenzo[a]quinolizine-3-carboxylate (165 mg, 0.36 mmol) in THF (10 mL) and ethanol (2 mL) was added 2.0 M LiOH aqueous solution (0.9 mL) at rt. The resulting mixture was stirred for 4 h, and then acidified to pH=1-2 with 2 M hydrochloric acid. The mixture was extracted with DCM (30 mL) 2 times. The combined organic layers were washed with water and brine, dried over anhydrous Na$_2$SO$_4$ and concentrated to give a yellow solid, which was purified by prep-HPLC to give 9-(cyclopropylmethoxy)-10-methoxy-6-(2-methoxy-1,1-dimethyl-ethyl)-2-oxo-6,7-dihydrobenzo[a]quinolizine-3-carboxylic acid (25 mg). $^1$H NMR (400 MHz, CDCl$_3$): δ 8.60-8.64 (m, 1H), 7.15-7.18 (m, 1H), 7.07-7.11 (m, 1H), 6.69-6.75 (m, 1H), 4.51-4.57 (m, 1H), 3.95 (s, 5H), 3.41-3.48 (m, 1H), 3.37 (s, 3H), 3.06-3.14 (m, 1H), 2.93 (s, 2H), 1.35-1.43 (m, 1H), 1.00 (s, 3H), 0.70-0.75 (m, 2H), 0.45 (s, 3H), 0.39-0.43 (m, 2H). MS obsd. (ESI$^+$) [(M+H)$^+$]: 428.

Example 10

10-Methoxy-6-(2-methoxy-1,1-dimethyl-ethyl)-9-(3-methylsulfanylpropoxy)-2-oxo-6,7-dihydrobenzo[a]quinolizine-3-carboxylic acid

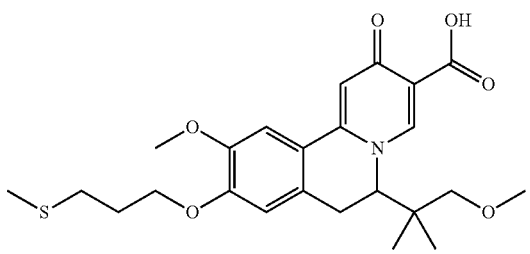

Step 1: Preparation of ethyl 10-methoxy-6-(2-methoxy-1,1-dimethyl-ethyl)-9-(3-methylsulfanylpropoxy)-2-oxo-6,7-dihydrobenzo[a]quinolizine-3-carboxylate

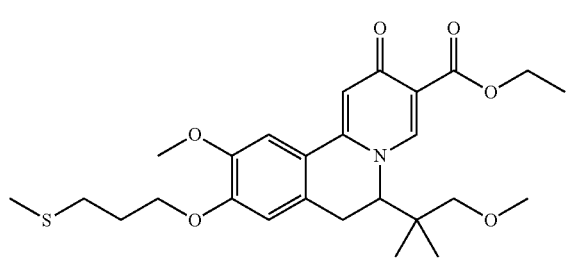

To a solution of ethyl 9-hydroxy-10-methoxy-6-(2-methoxy-1,1-dimethyl-ethyl)-2-oxo-6,7-dihydrobenzo[a]quinolizine-3-carboxylate (160 mg, 0.4 mmol) in DMF (5 mL) was added potassium carbonate (110 mg, 0.8 mmol) and 3-methylsulfanylpropyl 4-methylbenzenesulfonate (208 mg, 0.8 mmol, TCI). The resulting mixture was heated at 90° C. for 6 h. After being cooled to room temperature, the dark-brown mixture was poured into water (50 mL). The resulting mixture was extracted with DCM (50 mL) 2 times. The combined organic layers were washed with brine, dried over anhydrous Na$_2$SO$_4$, and concentrated under reduced pressure to give crude ethyl 10-methoxy-6-(2-methoxy-1,1-dimethyl-ethyl)-9-(3-methylsulfanylpropoxy)-2-oxo-6,7-dihydrobenzo[a]quinolizine-3-carboxylate (165 mg), which was used in the next step without further purification.

Step 2: Preparation of 10-methoxy-6-(2-methoxy-1,1-dimethyl-ethyl)-9-(3-methylsulfanylpropoxy)-2-oxo-6,7-dihydrobenzo[a]quinolizine-3-carboxylic acid

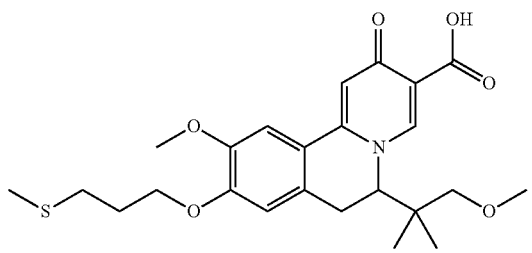

To a solution of ethyl 10-methoxy-6-(2-methoxy-1,1-dimethyl-ethyl)-9-(3-methylsulfanylpropoxy)-2-oxo-6,7-dihydrobenzo[a]quinolizine-3-carboxylate (165 mg, 0.36 mmol) in THF (10 mL) and ethanol (2 mL) was added 2.0 M LiOH aqueous solution (0.9 mL) at rt. The resulting mixture was stirred for 4 h, and then acidified to pH=1-2 with 2 M hydrochloric acid. The mixture was extracted with DCM (30 mL) 2 times. The combined organic layers were washed with water and brine, dried over anhydrous Na$_2$SO$_4$ and concentrated to give a yellow solid, which was purified by prep-HPLC to give 10-methoxy-6-(2-methoxy-1,1-dimethyl-ethyl)-9-(3-methylsulfanylpropoxy)-2-oxo-6,7-dihydrobenzo[a]quinolizine-3-carboxylic acid (4 mg). $^1$H NMR (400 MHz, CDCl$_3$): δ 8.65-8.69 (m, 1H), 7.13-7.19 (m, 2H), 6.76-6.80 (m, 1H), 4.56-4.61 (m, 1H), 4.17-4.28 (m, 2H), 3.94 (s, 3H), 3.44-3.52 (m, 1H), 3.37 (s, 3H), 3.10-3.16 (m, 1H), 2.90-2.98 (m, 2H), 2.72-2.78 (m, 2H), 2.18-2.24 (m, 2H), 2.16 (s, 3H), 1.01 (s, 3H), 0.46 (s, 3H). MS obsd. (ESI$^+$) [(M+H)$^+$]: 462.

Example 11

10-Methoxy-6-(2-methoxy-1,1-dimethyl-ethyl)-2-oxo-9-(3-pyrrolidin-1-ylpropoxy)-6,7-dihydrobenzo[a]quinolizine-3-carboxylic acid

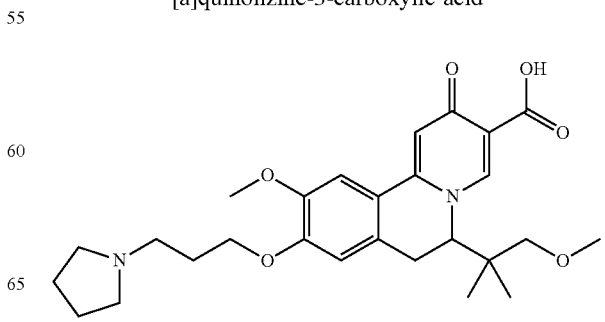

Step 1: Preparation of ethyl 10-methoxy-6-(2-methoxy-1,1-dimethyl-ethyl)-2-oxo-9-(3-(pyrrolidin-1-ylpropoxy)-6,7-dihydrobenzo[a]quinolizine-3-carboxylate

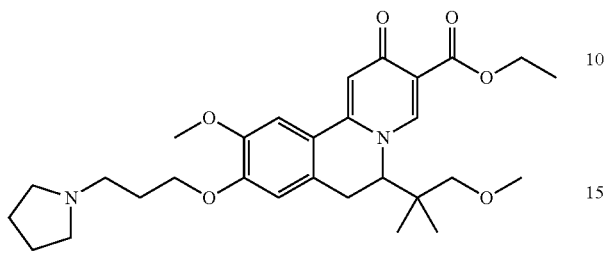

To a solution of ethyl 9-hydroxy-10-methoxy-6-(2-methoxy-1,1-dimethyl-ethyl)-2-oxo-6,7-dihydrobenzo[a]quinolizine-3-carboxylate (160 mg, 0.4 mmol) in DMF (5 mL) was added potassium carbonate (165 mg, 1.2 mmol) and 1-(3-chloropropyl)pyrrolidine hydrochloride (147 mg, 0.8 mmol, TCI). The resulting mixture was heated at 90° C. for 6 h. After being cooled to room temperature, the dark-brown mixture was poured into water (50 mL). The resulting mixture was extracted with DCM (50 mL) 2 times. The combined organic layers were washed with brine, dried over anhydrous Na$_2$SO$_4$, and concentrated under reduced pressure to give crude ethyl 10-methoxy-6-(2-methoxy-1,1-dimethyl-ethyl)-2-oxo-9-(3-pyrrolidin-1-ylpropoxy)-6,7-dihydrobenzo[a]quinolizine-3-carboxylate (185 mg), which was used in the next step without further purification.

Step 2: Preparation of 10-methoxy-6-(2-methoxy-1,1-dimethyl-ethyl)-2-oxo-9-(3-pyrrolidin-1-ylpropoxy)-6,7-dihydrobenzo[a]quinolizine-3-carboxylic acid

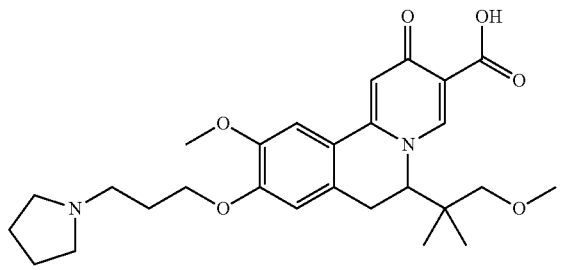 [SMILES: COCC(C)(C)C1Cc2cc(OCCCN3CCCC3)c(OC)cc2-c2cc(=O)c(C(=O)O)cn21]

To a solution of ethyl 10-methoxy-6-(2-methoxy-1,1-dimethyl-ethyl)-2-oxo-9-(3-pyrrolidin-1-ylpropoxy)-6,7-dihydrobenzo[a]quinolizine-3-carboxylate (185 mg, 0.36 mmol) in THF (10 mL) and ethanol (2 mL) was added 2.0 M LiOH aqueous solution (0.9 mL) at rt. The resulting mixture was stirred for 4 h, and then acidified to pH=5-6 with 2 M hydrochloric acid. The mixture was extracted with DCM (30 mL) 2 times. The combined organic layers were washed with water and brine, dried over anhydrous Na$_2$SO$_4$ and concentrated to give a yellow solid, which was purified by prep-HPLC to give 10-methoxy-6-(2-methoxy-1,1-dim- ethyl-ethyl)-2-oxo-9-(3-pyrrolidin-1-ylpropoxy)-6,7-dihydrobenzo[a]quinolizine-3-carboxylic acid (4 mg). $^1$H NMR (400 MHz, CDCl$_3$): δ 8.58-8.62 (m, 1H), 7.12-7.17 (m, 1H), 7.04-7.08 (m, 1H), 6.79-6.85 (m, 1H), 4.50-4.57 (m, 1H), 4.18-4.31 (m, 2H), 3.93 (s, 3H), 3.40-3.47 (m, 1H), 3.37 (s, 3H), 3.10-3.17 (m, 1H), 2.93 (m, 6H), 2.27-2.35 (m, 2H), 1.94-2.05 (m, 6H), 1.00 (s, 3H), 0.45 (s, 3H). MS obsd. (ESI$^+$) [(M+H)$^+$]: 485.

Example 12

10-Methoxy-6-(2-methoxy-1,1-dimethyl-ethyl)-2-oxo-9-[3-(2-oxopyrrolidin-1-yl)propoxy]-6,7-dihydrobenzo[a]quinolizine-3-carboxylic acid

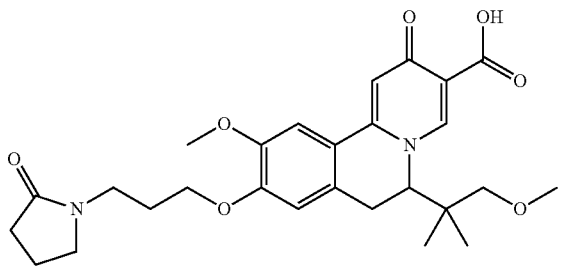 [SMILES: COCC(C)(C)C1Cc2cc(OCCCN3CCCC3=O)c(OC)cc2-c2cc(=O)c(C(=O)O)cn21]

Step 1: Preparation of ethyl 10-methoxy-6-(2-methoxy-1,1-dimethyl-ethyl)-2-oxo-9-[3-(2-oxopyrrolidin-1-yl)propoxy]-6,7-dihydrobenzo[a]quinolizine-3-carboxylate

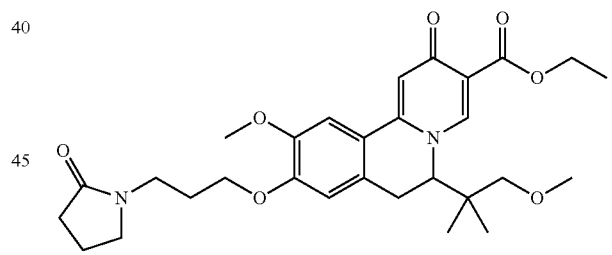

To a solution of ethyl 9-hydroxy-10-methoxy-6-(2-methoxy-1,1-dimethyl-ethyl)-2-oxo-6,7-dihydrobenzo[a]quinolizine-3-carboxylate (160 mg, 0.4 mmol) in DMF (5 mL) was added potassium carbonate (110 mg, 0.8 mmol) and 3-(2-oxopyrrolidin-1-yl)propyl 4-methylbenzenesulfonate (178 mg, 0.8 mmol, TCI). The resulting mixture was heated at 90° C. for 6 h. After being cooled to room temperature, the dark-brown mixture was poured into water (50 mL). The resulting mixture was extracted with DCM (50 mL) 2 times. The combined organic layers were washed with brine, dried over anhydrous Na$_2$SO$_4$, and concentrated under reduced pressure to give crude ethyl 10-methoxy-6-(2-methoxy-1,1-dimethyl-ethyl)-2-oxo-9-[3-(2-oxopyrrolidin-1-yl)propoxy]-6,7-dihydrobenzo[a]quinolizine-3-carboxylate (185 mg), which was used in the next step without further purification.

Step 2: Preparation of 10-methoxy-6-(2-methoxy-1, 1-dimethyl-ethyl)-2-oxo-9-[3-(2-oxopyrrolidin-1-yl) propoxy]-6,7-dihydrobenzo[a]quinolizine-3-carboxylic acid

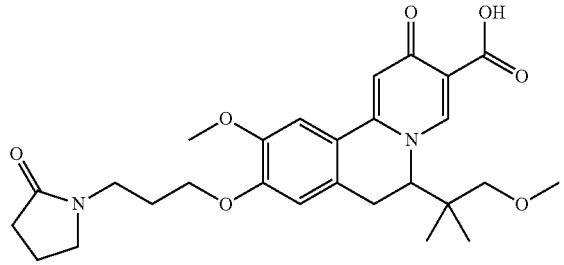 [SMILES: COCC(C)(C)C1Cc2cc(OCCCN3CCCC3=O)c(OC)cc2-c2cc(=O)c(C(=O)O)cn21]

To a solution of ethyl 10-methoxy-6-(2-methoxy-1,1-dimethyl-ethyl)-2-oxo-9-[3-(2-oxopyrrolidin-1-yl)propoxy]-6,7-dihydrobenzo[a]quinolizine-3-carboxylate (185 mg, 0.36 mmol) in THF (10 mL) and ethanol (2 mL) was added 2.0 M LiOH aqueous solution (0.9 mL) at rt. The resulting mixture was stirred for 4 h, and then acidified to pH=1-2 with 2 M hydrochloric acid. The mixture was extracted with DCM (30 mL) 2 times. The combined organic layers were washed with water and brine, dried over anhydrous $Na_2SO_4$ and concentrated to give a yellow solid, which was purified by prep-HPLC to give 10-methoxy-6-(2-methoxy-1,1-dimethyl-ethyl)-2-oxo-9-[3-(2-oxopyrrolidin-1-yl)propoxy]-6,7-dihydrobenzo[a]quinolizine-3-carboxylic acid (4 mg). $^1$H NMR (400 MHz, $CDCl_3$): δ 8.58-8.62 (m, 1H), 7.15 (s, 1H), 7.06 (s, 1H), 6.71-6.78 (m, 1H), 4.50-4.57 (m, 1H), 4.05-4.18 (m, 2H), 3.93 (s, 3H), 3.49 (d, J=7.03 Hz, 4H), 3.39-3.45 (m, 1H), 3.37 (s, 3H), 3.10-3.16 (m, 1H), 2.93 (s, 2H), 2.37-2.45 (m, 2H), 2.11-2.19 (m, 2H), 2.01-2.09 (m, 2H), 0.99 (s, 3H), 0.45 (s, 3H). MS obsd. (ESI$^+$) [(M+H)$^+$]: 499.

Example 13

9-[3-(Dimethylamino)propoxy]-10-methoxy-6-(2-methoxy-1,1-dimethyl-ethyl)-2-oxo-6,7-dihydrobenzo[a]quinolizine-3-carboxylic acid

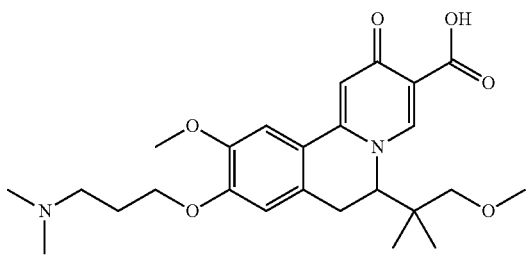

Step 1: Preparation of ethyl 9-[3-(dimethylamino) propoxy]-10-methoxy-6-(2-methoxy-1,1-dimethyl-ethyl)-2-oxo-6,7-dihydrobenzo[a]quinolizine-3-carboxylate

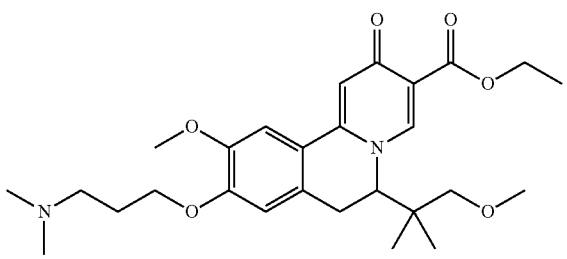 [SMILES: CCOC(=O)c1cn2c(cc1=O)-c1cc(OC)c(OCCCN(C)C)cc1CC2C(C)(C)COC]

To a solution of ethyl 9-hydroxy-10-methoxy-6-(2-methoxy-1,1-dimethyl-ethyl)-2-oxo-6,7-dihydrobenzo[a]quinolizine-3-carboxylate (160 mg, 0.4 mmol) in DMF (5 mL) was added potassium carbonate (165 mg, 1.2 mmol) and 3-chloro-N,N-dimethyl-propan-1-amine hydrochloride (126 mg, 0.8 mmol, Aldrich). The resulting mixture was heated at 90° C. for 6 h. After being cooled to room temperature, the dark-brown mixture was poured into water (50 mL). The resulting mixture was extracted with DCM (50 mL) 2 times. The combined organic layers were washed with brine, dried over anhydrous $Na_2SO_4$, and concentrated under reduced pressure to give crude ethyl 9-[3-(dimethylamino)propoxy]-10-methoxy-6-(2-methoxy-1,1-dimethyl-ethyl)-2-oxo-6,7-dihydrobenzo[a]quinolizine-3-carboxylate (175 mg), which was used in the next step without further purification.

Step 2: Preparation of 9-[3-(dimethylamino) propoxy]-10-methoxy-6-(2-methoxy-1,1-dimethyl-ethyl)-2-oxo-6,7-dihydrobenzo[a]quinolizine-3-carboxylic acid

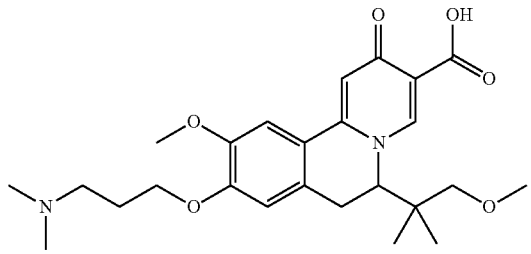

To a solution of ethyl 9-[3-(dimethylamino)propoxy]-10-methoxy-6-(2-methoxy-1,1-dimethyl-ethyl)-2-oxo-6,7-dihydrobenzo[a]quinolizine-3-carboxylate (175 mg, 0.36 mmol) in THF (10 mL) and ethanol (2 mL) was added 2.0 M LiOH aqueous solution (0.9 mL) at rt. The resulting mixture was stirred for 4 h, and then acidified to pH=5-6 with 2 M hydrochloric acid. The mixture was extracted with DCM (30 mL) 2 times. The combined organic layers were washed with water and brine, dried over anhydrous $Na_2SO_4$ and concentrated to give a yellow solid, which was purified by prep-HPLC to give 9-[3-(dimethylamino)propoxy]-10-methoxy-6-(2-methoxy-1,1-dimethyl-ethyl)-2-oxo-6,7-dihydrobenzo[a]quinolizine-3-carboxylic acid (6 mg). $^1$H NMR (400 MHz, $CDCl_3$): δ 8.58-8.63 (m, 1H), 7.12-7.18 (m, 1H), 7.03-7.09 (m, 1H), 6.76-6.82 (m, 1H), 4.50-4.57 (m, 1H), 4.14-4.26 (m, 2H), 3.93 (s, 3H), 3.39-3.46 (m, 1H), 3.37 (s, 3H), 3.08-3.16 (m, 1H), 2.93 (s, 2H), 2.69-2.78 (m, 2H), 2.46 (s, 6H), 2.15-2.25 (m, 2H), 1.00 (s, 3H), 0.44 (s, 3H). MS obsd. (ESI$^+$) [(M+H)$^+$]: 459.

Example 14

9-[6-(tert-Butoxycarbonylamino)hexoxy]-10-methoxy-6-(2-methoxy-1,1-dimethyl-ethyl)-2-oxo-6, 7-dihydrobenzo[a]quinolizine-3-carboxylic acid

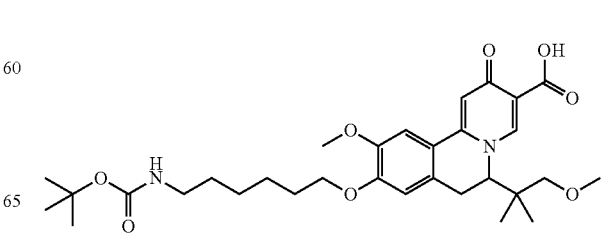

Step 1: Preparation of ethyl 9-[6-(tert-butoxycarbonylamino)hexoxy]-10-methoxy-6-(2-methoxy-1,1-dimethyl-ethyl)-2-oxo-6,7-dihydrobenzo[a]quinolizine-3-carboxylate

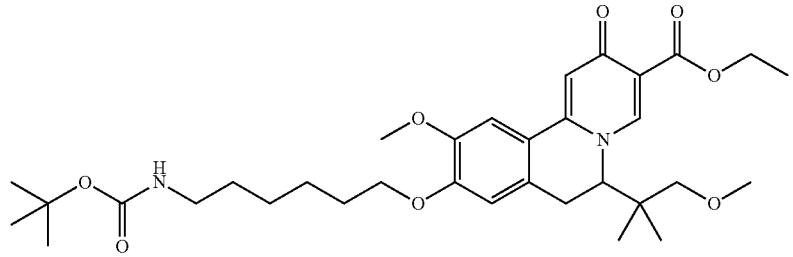 [SMILES: CCOC(=O)c1cn2c(cc1=O)-c1cc(OC)c(OCCCCCCNC(=O)OC(C)(C)C)cc1CC2C(C)(C)COC]

To a solution of ethyl 9-hydroxy-10-methoxy-6-(2-methoxy-1,1-dimethyl-ethyl)-2-oxo-6,7-dihydrobenzo[a]quinolizine-3-carboxylate (160 mg, 0.4 mmol) in DMF (5 mL) was added potassium carbonate (110 mg, 0.8 mmol) and 6-(tert-butoxycarbonylamino)hexyl 4-methylbenzenesulfonate (300 mg, 0.8 mmol, Aldrich). The resulting mixture was heated at 90° C. for 6 h. After being cooled to room temperature, the dark-brown mixture was poured into water (50 mL). The resulting mixture was extracted with DCM (50 mL) 2 times. The combined organic layers were washed with brine, dried over anhydrous $Na_2SO_4$, and concentrated under reduced pressure to give crude ethyl 9-[6-(tert-butoxycarbonylamino)hexoxy]-10-methoxy-6-(2-methoxy-1,1-dimethyl-ethyl)-2-oxo-6,7-dihydrobenzo[a]quinolizine-3-carboxylate (210 mg), which was used directly in the next step without further purification.

Step 2: Preparation of 9-[6-(tert-butoxycarbonylamino)hexoxy]-10-methoxy-6-(2-methoxy-1,1-dimethyl-ethyl)-2-oxo-6,7-dihydrobenzo[a]quinolizine-3-carboxylic acid

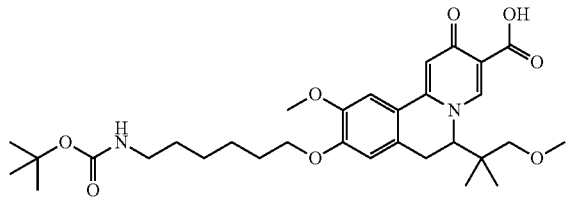 [SMILES: COCC(C)(C)C1Cc2cc(OCCCCCCNC(=O)OC(C)(C)C)c(OC)cc2-c2cc(=O)c(C(=O)O)cn21]

To a solution of ethyl 9-[6-(tert-butoxycarbonylamino)hexoxy]-10-methoxy-6-(2-methoxy-1,1-dimethyl-ethyl)-2-oxo-6,7-dihydrobenzo[a]quinolizine-3-carboxylate (210 mg, 0.36 mmol) in THF (10 mL) and ethanol (2 mL) was added 2.0 M LiOH aqueous solution (0.9 mL) at rt. The resulting mixture was stirred for 4 h, and then acidified to pH=6-7 with 2 M hydrochloric acid. The mixture was extracted with DCM (30 mL) 2 times. The combined organic layers were washed with water and brine, dried over anhydrous $Na_2SO_4$ and concentrated to give a yellow solid, which was purified by prep-HPLC to give 9-[6-(tert-butoxycarbonylamino)hexoxy]-10-methoxy-6-(2-methoxy-1,1-dimethyl-ethyl)-2-oxo-6,7-dihydrobenzo[a]quinolizine-3-carboxylic acid (30 mg). $^1$H NMR (400 MHz, $CDCl_3$): δ 8.59-8.63 (m, 1H), 7.13-7.17 (m, 1H), 7.06-7.10 (m, 1H), 6.70-6.75 (m, 1H), 4.51-4.57 (m, 1H), 4.05-4.13 (m, 2H), 3.94 (s, 3H), 3.41-3.47 (m, 1H), 3.38 (s, 3H), 3.12-3.20 (m, 3H), 2.94 (s, 2H), 1.87-1.96 (m, 2H), 1.50-1.60 (m, 6H), 1.46 (s, 9H), 1.01 (s, 3H), 0.45 (s, 3H). MS obsd. (ESI$^+$) [(M+H)$^+$]: 573.

Example 15

10-Methoxy-6-(2-methoxy-1,1-dimethyl-ethyl)-9-(3-methylsulfonylpropoxy)-2-oxo-6,7-dihydrobenzo[a]quinolizine-3-carboxylic acid

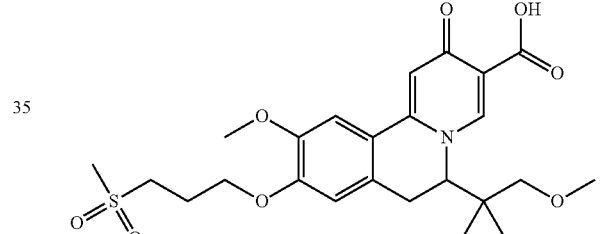

Step 1: Preparation of ethyl 10-methoxy-6-(2-methoxy-1,1-dimethyl-ethyl)-9-(3-methylsulfonylpropoxy)-2-oxo-6,7-dihydrobenzo[a]quinolizine-3-carboxylate

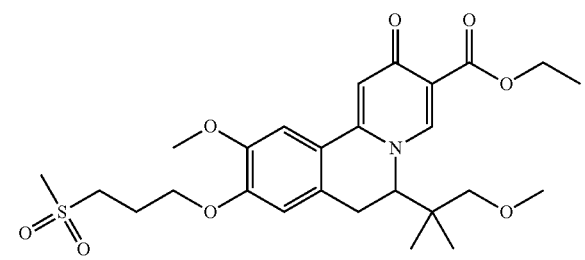 [SMILES: CCOC(=O)c1cn2c(cc1=O)-c1cc(OC)c(OCCCS(C)(=O)=O)cc1CC2C(C)(C)COC]

To a solution of ethyl 10-methoxy-6-(2-methoxy-1,1-dimethyl-ethyl)-9-(3-methylsulfanylpropoxy)-2-oxo-6,7-dihydrobenzo[a]quinolizine-3-carboxylate (146 mg, 0.3 mmol) in DCM (10 mL) was added 3-chloroperoxybenzoic acid (200 mg, 0.9 mmol, Accela) at 0° C. and then the resulting mixture was stirred at rt for 2 h. The mixture was poured into $NaHCO_3$ aqueous solution (20 mL) and stirred for 1 h. The mixture was extracted with DCM (50 mL) 2 times. The combined organic layers were washed with water (30 mL) 2 times and brine, dried over anhydrous Na$_2$SO$_4$ and concentrated to give ethyl 10-methoxy-6-(2-methoxy-1,1-dimethyl-ethyl)-9-(3-methylsulfonylpropoxy)-2-oxo-6,7-dihydrobenzo[a]quinolizine-3-carboxylate (130 mg) as a yellow oil which was used in the next step without further purification.

Step 2: Preparation of 10-methoxy-6-(2-methoxy-1,1-dimethyl-ethyl)-9-(3-methylsulfonylpropoxy)-2-oxo-6,7-dihydrobenzo[a]quinolizine-3-carboxylic acid

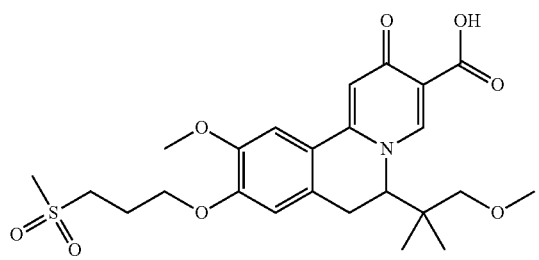 [SMILES: COCC(C)(C)C1Cc2cc(OCCCS(C)(=O)=O)c(OC)cc2-c2cc(=O)c(C(=O)O)cn21]

To a solution of ethyl 10-methoxy-6-(2-methoxy-1,1-dimethyl-ethyl)-9-(3-methylsulfonylpropoxy)-2-oxo-6,7-dihydrobenzo[a]quinolizine-3-carboxylate (130 mg, 0.25 mmol) in THF (10 mL) and ethanol (2 mL) was added 2.0 M LiOH aqueous solution (0.7 mL) at rt. The resulting mixture was stirred for 4 h, and then acidified to pH=1-2 with 2 M hydrochloric acid. The mixture was extracted with DCM (30 mL) 2 times. The combined organic layers were washed with water and brine, dried over anhydrous Na$_2$SO$_4$ and concentrated to give a yellow solid, which was purified by prep-HPLC to give 10-methoxy-6-(2-methoxy-1,1-ethyl-ethyl)-9-(3-methylsulfonylpropoxy)-2-oxo-6,7-dihydrobenzo[a]quinolizine-3-carboxylic acid (28 mg). $^1$H NMR (400 MHz, CDCl$_3$): δ 8.58-8.64 (m, 1H), 7.14-7.20 (m, 1H), 7.06-7.12 (m, 1H), 6.73-6.79 (m, 1H), 4.51-4.58 (m, 1H), 4.23-4.34 (m, 2H), 3.93 (s, 3H), 3.40-3.47 (m, 1H), 3.37 (s, 3H), 3.33 (br. s., 2H), 3.08-3.16 (m, 1H), 3.01 (s, 3H), 2.91-2.97 (m, 2H), 2.42-2.52 (m, 2H), 1.00 (s, 3H), 0.45 (s, 3H). MS obsd. (ESI$^+$) [(M+H)$^+$]: 494.

Example 16

9-(6-Aminohexoxy)-10-methoxy-6-(2-methoxy-1,1-dimethyl-ethyl)-2-oxo-6,7-dihydrobenzo[a]quinolizine-3-carboxylic acid

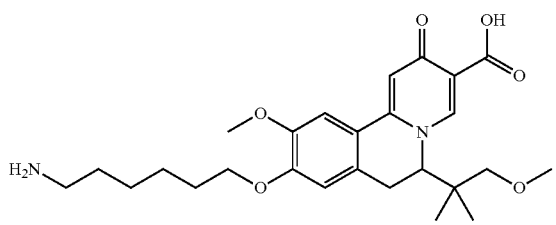 [SMILES: COCC(C)(C)C1Cc2cc(OCCCCCCN)c(OC)cc2-c2cc(=O)c(C(=O)O)cn21]

To a solution of 9-[6-(tert-butoxycarbonylamino)hexoxy]-10-methoxy-6-(2-methoxy-1,1-dimethyl-ethyl)-2-oxo-6,7-dihydrobenzo[a]quinolizine-3-carboxylic acid (120 mg, 0.2 mmol) in THF (10 mL) was added 6 M hydrochloric acid (1 mL) at room temperature. The resulting mixture was stirred for 4 h and then adjusted to pH=7-8 with 2 M Na$_2$CO$_3$ aqueous solution. The mixture was extracted with DCM (50 mL) 2 times. The combined organic layers were washed with water and brine, dried over anhydrous Na$_2$SO$_4$, and concentrated to give a yellow solid, which was purified by prep-HPLC to give 9-(6-aminohexoxy)-10-methoxy-6-(2-methoxy-1,1-dimethyl-ethyl)-2-oxo-6,7-dihydrobenzo[a]quinolizine-3-carboxylic acid (4 mg). $^1$H NMR (400 MHz, CDCl$_3$): δ 8.59-8.65 (m, 1H), 7.08-7.19 (m, 2H), 6.71-6.80 (m, 1H), 4.51-4.57 (m, 1H), 4.05-4.13 (m, 2H), 3.94 (s, 3H), 3.41-3.47 (m, 1H), 3.38 (s, 3H), 3.12-3.20 (m, 3H), 2.94 (s, 2H), 1.87-1.96 (m, 2H), 1.50-1.60 (m, 6H), 1.01 (s, 3H), 0.45 (s, 3H). MS obsd. (ESI$^+$) [(M+H)$^+$]: 473.

Example 17

10-Methoxy-6-(2-methoxy-1,1-dimethyl-ethyl)-9-[2-(1-methylpyrrolidin-2-yl)ethoxy]-2-oxo-6,7-dihydrobenzo[a]quinolizine-3-carboxylic acid

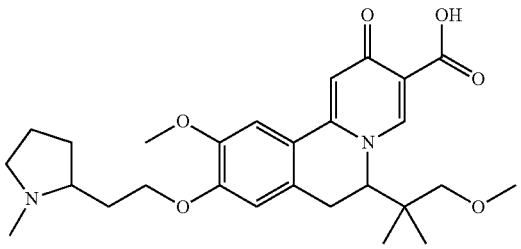 [SMILES: COCC(C)(C)C1Cc2cc(OCCC3CCCN3C)c(OC)cc2-c2cc(=O)c(C(=O)O)cn21]

Step 1: Preparation of ethyl 10-methoxy-6-(2-methoxy-1,1-dimethyl-ethyl)-9-[2-(1-methylpyrrolidin-2-yl)ethoxy]-2-oxo-6,7-dihydrobenzo[a]quinolizine-3-carboxylate

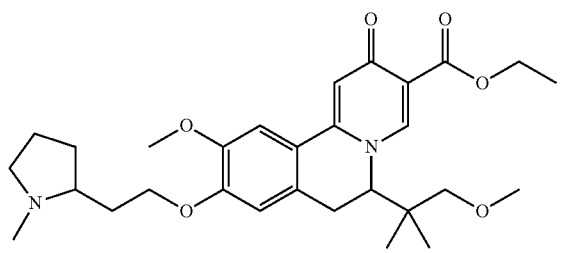 [SMILES: CCOC(=O)c1cn2c(cc1=O)-c1cc(OC)c(OCCC3CCCN3C)cc1CC2C(C)(C)COC]

To a solution of ethyl 9-hydroxy-10-methoxy-6-(2-methoxy-1,1-dimethyl-ethyl)-2-oxo-6,7-dihydrobenzo[a]quinolizine-3-carboxylate (160 mg, 0.4 mmol) in DMF (5 mL) was added potassium carbonate (165 mg, 1.2 mmol) and 2-(2-chloroethyl)-1-methyl-pyrrolidine hydrochloride (150 mg, 0.8 mmol, Aldrich). The resulting mixture was heated at 90° C. for 6 h. After being cooled to room temperature, the dark-brown mixture was poured into water (50 mL). The resulting mixture was extracted with DCM (50 mL) 2 times. The combined organic layers were washed with brine, dried over anhydrous Na$_2$SO$_4$, and concentrated under reduced pressure to give crude ethyl 10-methoxy-6-(2-methoxy-1,1-dimethyl-ethyl)-9-[2-(1-methylpyrrolidin-2- yl)ethoxy]-2-oxo-6,7-dihydrobenzo[a]quinolizine-3-carboxylate (185 mg), which was used in the next step without further purification.

Step 2: Preparation of 10-methoxy-6-(2-methoxy-1,1-dimethyl-ethyl)-9-[2-(1-methylpyrrolidin-2-yl)ethoxy]-2-oxo-6,7-dihydrobenzo[a]quinolizine-3-carboxylic acid

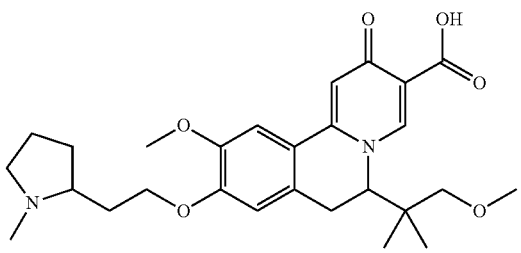 [SMILES: COCC(C)(C)C1Cc2cc(OCCC3CCCN3C)c(OC)cc2-c2cc(=O)c(C(=O)O)cn21]

To a solution of ethyl 10-methoxy-6-(2-methoxy-1,1-dimethyl-ethyl)-9-[2-(1-methylpyrrolidin-2-yl)ethoxy]-2-oxo-6,7-dihydrobenzo[a]quinolizine-3-carboxylate (185 mg, 0.36 mmol) in THF (10 mL) and ethanol (2 mL) was added 2.0 M LiOH aqueous solution (0.9 mL) at rt. The resulting mixture was stirred for 4 h, and then acidified to pH=1-2 with 2 M hydrochloric acid. The mixture was extracted with DCM (30 mL) 2 times. The combined organic layers were washed with water and brine, dried over anhydrous $Na_2SO_4$ and concentrated to give a yellow solid, which was purified by prep-HPLC to give 10-methoxy-6-(2-methoxy-1,1-dimethyl-ethyl)-9-[2-(1-methylpyrrolidin-2-yl)ethoxy]-2-oxo-6,7-dihydrobenzo[a]quinolizine-3-carboxylic acid (15 mg). $^1$H NMR (400 MHz, CDCl$_3$): δ 8.54-8.64 (m, 1H), 7.14-7.18 (m, 1H), 7.04-7.08 (m, 1H), 6.72-6.81 (m, 1H), 4.49-4.57 (m, 1H), 4.11-4.28 (m, 2H), 3.93 (s, 3H), 3.40-3.47 (m, 1H), 3.38 (s, 3H), 3.21-3.31 (m, 1H), 3.08-3.16 (m, 1H), 2.93 (s, 2H), 2.44-2.52 (m, 3H), 2.28-2.41 (m, 2H), 1.88-2.15 (m, 6H), 1.00 (s, 3H), 0.45 (s, 3H). MS obsd. (ESI$^+$) [(M+H)$^+$]: 485.

Example 18

10-Methoxy-6-(methoxymethyl)-9-(3-methoxy-propoxy)-2-oxo-6,7-dihydrobenzo[a]quinolizine-3-carboxylic acid

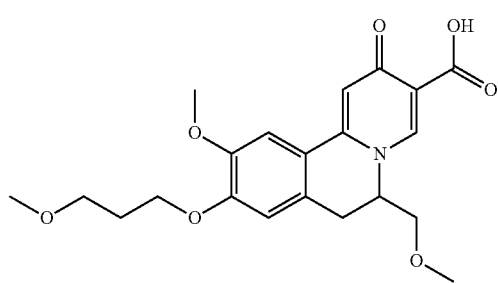 [SMILES: COCCCOc1cc2c(cc1OC)-c1cc(=O)c(C(=O)O)cn1C(COC)C2]

Step 1: Preparation of trimethylsilyl 2-methoxyacetate

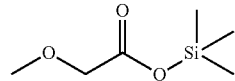

To a stirred solution of methoxyacetic acid (87 g, 0.97 mol) in THF (100 mL) and pyridine (50 mL) at 0° C. was added HMDS (156 g, 0.97 mol) followed by the addition of Me$_3$SiCl (153 g, 0.48 mol) dropwise. After being stirred for 17 h, the mixture was diluted with petroleum ether and filtered through Celite. The filtrate was concentrated, and the residue was distilled at aspirator pressure (64 mbar, 88° C.) to give trimethylsilyl 2-methoxyacetate (80 g).

Step 2: Preparation of (2-methoxy-1-trimethylsilyloxy-vinyloxy)-trimethyl-silane

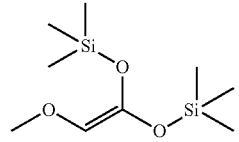

To a stirred solution of LiHMDS (500 mL, 1 M in THF) at −78° C., trimethylsilyl 2-methoxyacetate (78 g, 0.42 mol) was added dropwise over a 30 min period. After being stirred for an additional 30 min, Me$_3$SiCl (69 g, 0.63 mol) was added dropwise. The resulting mixture was allowed to warm to rt, poured into petroleum ether (1 L) and filtered through Celite. The filtrate was concentrated, and the residue was re-dissolved in petroleum ether. The mixture was filtered again, and the filtrate was concentrated. The residue was distilled (0.1 mmHg, 54-56° C.) to give (2-methoxy-1-trimethylsilyloxy-vinyloxy)-trimethyl-silane (80 g).

Step 3: Preparation of methyl 2-(3-hydroxy-4-methoxy-phenyl)acetate

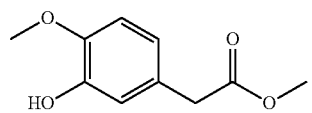

2-(3-Hydroxy-4-methoxy-phenyl)acetic acid (25 g, 0.14 mol) was dissolved in methanol (200 mL), then to the solution, concentrated H$_2$SO$_4$ (8 mL) was added. The mixture was refluxed for 3 h and concentrated. The residue was partitioned between ethyl acetate (50 mL) and water. The organic layer was separated, dried over anhydrous Na$_2$SO$_4$ and concentrated to give methyl 2-(3-hydroxy-4-methoxy-phenyl)acetate (28 g) which was used directly in the next step.

Step 4: Preparation of methyl 2-[4-methoxy-3-(3-methoxypropoxy)phenyl]acetate

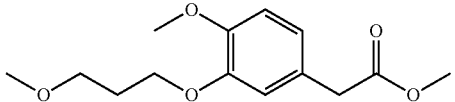

A mixture of methyl 2-(3-hydroxy-4-methoxy-phenyl)acetate (28 g, 0.14 mol), 1-bromo-3-methoxy-propane (21 g, 0.14 mol) and $K_2CO_3$ (38 g, 0.27 mol) in DMF (20 mL) was heated at 60° C. for 3 h. Then the mixture was partitioned between water (100 mL) and ethyl acetate (100 mL). The organic layer was separated, dried over anhydrous $Na_2SO_4$ and concentrated to give methyl 2-[4-methoxy-3-(3-methoxypropoxy)phenyl]acetate (32 g) which was used directly in the next step.

Step 5: Preparation of 2-[4-methoxy-3-(3-methoxypropoxy)phenyl]acetic acid

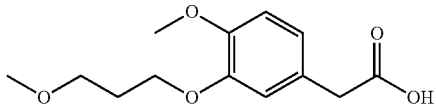 [SMILES: COCCCOc1cc(CC(=O)O)ccc1OC]

To a solution of methyl 2-[4-methoxy-3-(3-methoxypropoxy)phenyl]acetate (10 g, 42 mmol) in ethanol (20 mL) was added 2 M NaOH aqueous solution. The mixture was stirred at rt for 3 h. After removal of most of ethanol by concentration, the mixture was adjusted to pH=1 with 1 M hydrochloric acid and then extracted with ethyl acetate (100 mL). The organic layer was dried over anhydrous $Na_2SO_4$ and concentrated to give 2-[4-methoxy-3-(3-methoxypropoxy)phenyl]acetic acid (12 g) which was used directly in the next step.

Step 6: Preparation of 2-[4-methoxy-3-(3-methoxypropoxy)phenyl]acetyl chloride

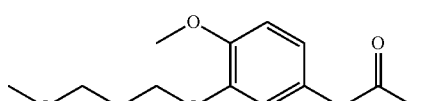

To a solution of 2-[4-methoxy-3-(3-methoxypropoxy)phenyl]acetic acid (12 g, 42 mmol) in DCM (30 mL) was added $SOCl_2$ (6 g, 42 mmol). The mixture was stirred at 40° C. for 2 h and then concentrated to give 2-[4-methoxy-3-(3-methoxypropoxy)phenyl]acetyl chloride.

Step 7: Preparation of 1-[4-methoxy-3-(3-methoxypropoxy)phenyl]-3,3-dimethyl-butan-2-one

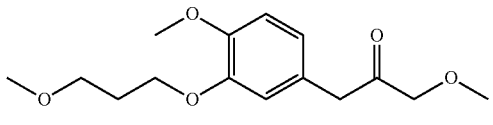

To a stirred mixture of 2-[4-methoxy-3-(3-methoxypropoxy)phenyl]acetyl chloride (12 g, 42 mmol) and (2-methoxy-1-trimethylsilyloxy-vinyloxy)-trimethyl-silane (21 g, 90 mmol) was added three drops of $SnCl_4$. After 1 h, the mixture was slowly poured into a mixture of dioxane (25 mL) and 0.6 M hydrochloric acid (10 mL). The mixture was maintained at 90° C. for 10 min, saturated with NaCl, and extracted with diethyl ether. The diethyl ether phase was washed with saturated $NaHCO_3$ aqueous solution, dried over anhydrous $Na_2SO_4$, and concentrated to give 1-[4-methoxy-3-(3-methoxypropoxy)phenyl]-3,3-dimethyl-butan-2-one (8 g).

Step 8: Preparation of 1-methoxy-3-[4-methoxy-3-(3-methoxypropoxy)phenyl]propan-2-amine

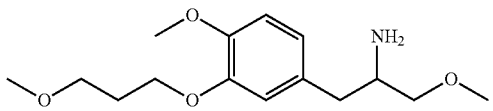

To a solution of 1-[4-methoxy-3-(3-methoxypropoxy)phenyl]-3,3-dimethyl-butan-2-one (3.6 g, 13 mmol) in methanol (100 mL) was added ammonium acetate (15 g, 189 mmol) and $NaBH_3CN$ (1.6 g, 25 mmol). The resulting mixture was stirred for 12 h at room temperature. The reaction was quenched with water, and to the mixture 2.0 M NaOH aqueous solution (50 mL) was added. The resulting mixture was stirred for 1 h and extracted with ethyl acetate (150 mL). The organic layer was washed with water (50 mL) 2 times and brine, dried over anhydrous $Na_2SO_4$ and concentrated to give 1-methoxy-3-[4-methoxy-3-(3-methoxypropoxy)phenyl]propan-2-amine (3.6 g) which was used in the next step without further purification.

Step 9: Preparation of N-[2-methoxy-1-[[4-methoxy-3-(3-methoxypropoxy)phenyl]methyl]ethyl]formamide

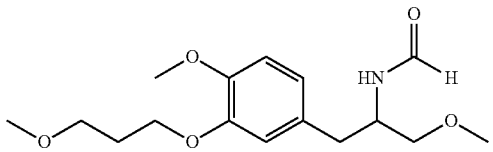

A mixture of 1-methoxy-3-[4-methoxy-3-(3-methoxypropoxy)phenyl]propan-2-amine (3.6 g, 12 mmol) and formic acid (2 g, 24 mmol) in 1,4-dioxane (100 mL) was refluxed for 12 h. The mixture was concentrated, and the residue was dissolved in ethyl acetate (100 mL). The resulting solution was washed with water (50 mL) 2 times and brine, dried over anhydrous Na₂SO₄ and concentrated to give N-[2-methoxy-1-[[4-methoxy-3-(3-methoxypropoxy)phenyl]methyl]ethyl]formamide (3.6 g).

Step 10: Preparation of 7-methoxy-3-(methoxymethyl)-6-(3-methoxypropoxy)-3,4-dihydroisoquinoline

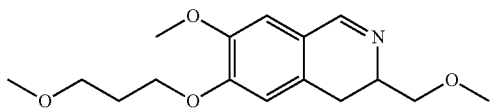

To a solution of N-[2-methoxy-1-[[4-methoxy-3-(3-methoxypropoxy)phenyl]methyl]ethyl]formamide (3.6 g, 12 mmol) in acetonitrile (50 mL) was added POCl₃ (1.8 g, 12 mol) dropwise at 0-5° C. The resulting mixture was refluxed for 3 h. After being cooled to rt, the mixture was concentrated. Then ethyl acetate (50 mL) was added, followed by addition of ammonia water to adjust the pH of the aqueous solution to around 11. The mixture was extracted with ethyl acetate (50 mL) 2 times. The organic layers were combined and concentrated. The residue was purified by column chromatography to give 7-methoxy-3-(methoxymethyl)-6-(3-methoxypropoxy)-3,4-dihydroisoquinoline (2.4 g).

Step 11: Preparation of ethyl 10-methoxy-6-(methoxymethyl)-9-(3-methoxypropoxy)-2-oxo-1,6,7,11b-tetrahydrobenzo[a]quinolizine-3-carboxylate

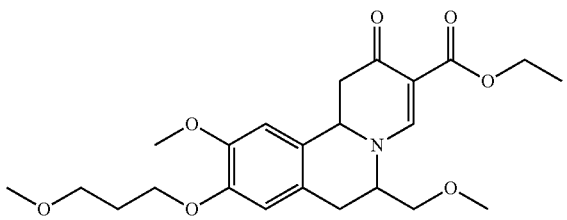

A mixture of 7-methoxy-3-(methoxymethyl)-6-(3-methoxypropoxy)-3,4-dihydroisoquinoline (2.4 g, 8.2 mmol) and ethyl 2-(ethoxymethylene)-3-oxo-butanoate (4.6 g, 24 mmol) in ethanol (80 mL) was refluxed overnight. The mixture was concentrated to give crude ethyl 10-methoxy-6-(methoxymethyl)-9-(3-methoxypropoxy)-2-oxo-1,6,7,11b-tetrahydrobenzo[a]quinolizine-3-carboxylate (5 g) as a dark brown oil which was used in the next step without purification.

Step 12: Preparation of ethyl 10-methoxy-6-(methoxymethyl)-9-(3-methoxypropoxy)-2-oxo-6,7-dihydrobenzo[a]quinolizine-3-carboxylate

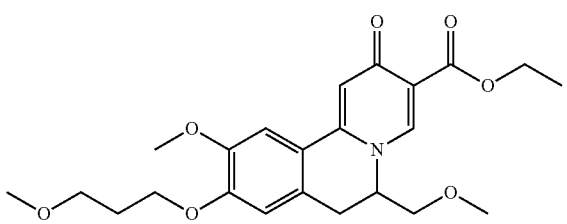 [SMILES: CCOC(=O)C1=CN2C(COC)Cc3cc(OCCCOC)c(OC)cc3C2CC1=O]

A mixture of crude ethyl 10-methoxy-6-(methoxymethyl)-9-(3-methoxypropoxy)-2-oxo-1,6,7,11b-tetrahydrobenzo[a]quinolizine-3-carboxylate (5 g) from and p-chloranil (2 g, 8 mmol) in DME (50 mL) was refluxed for 2 h. After being cooled to rt, the mixture was concentrated. The residue was dissolved in ethyl acetate (100 mL). The resulting mixture was washed with water (50 mL) 2 times and brine, dried over anhydrous Na₂SO₄ and concentrated to give crude ethyl 10-methoxy-6-(methoxymethyl)-9-(3-methoxypropoxy)-2-oxo-6,7-dihydrobenzo[a]quinolizine-3-carboxylate which used directly in the next step.

Step 13: Preparation of 10-methoxy-6-(methoxymethyl)-9-(3-methoxypropoxy)-2-oxo-6,7-dihydrobenzo[a]quinolizine-3-carboxylic acid

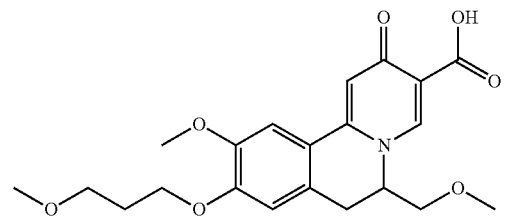 [SMILES: COCCCOc1cc2c(cc1OC)-c1cc(=O)c(C(=O)O)cn1C(COC)C2]

To a solution of ethyl 10-methoxy-6-(methoxymethyl)-9-(3-methoxypropoxy)-2-oxo-6,7-dihydrobenzo[a]quinolizine-3-carboxylate (5 g crude) in THF (10 mL) and ethanol (20 mL) was added 2.0 M LiOH aqueous solution (10 mL) at rt. The resulting mixture was stirred for 4 h, and then acidified to pH=1-2 with 2 M hydrochloric acid. The mixture was extracted with DCM (50 mL) 2 times. The combined organic layers were washed with water and brine, dried over anhydrous Na₂SO₄ and concentrated to give a brown oil, which was purified by column chromatography to give 10-methoxy-6-(methoxymethyl)-9-(3-methoxypropoxy)-2-oxo-6,7-dihydrobenzo[a]quinolizine-3-carboxylic acid (500 mg). ¹H NMR (400 MHz, DMSO-d6) δ 8.63 (s, 1H), 7.53 (s, 1H), 7.48 (s, 1H), 7.01 (s, 1H), 4.91-5.01 (m, 1H), 4.10 (m, 2H), 3.89 (s, 3H), 3.48 (m, 6H), 3.25-3.29 (m, 3H), 3.18 (s, 3H), 1.99 (m, 2H). MS obsd. (ESI⁺) [(M+H)⁺]: 404.

Example 19

10-Chloro-9-(3-methoxypropoxy)-2-oxo-6-tetrahydropyran-4-yl-6,7-dihydrobenzo[a]quinolizine-3-carboxylic acid

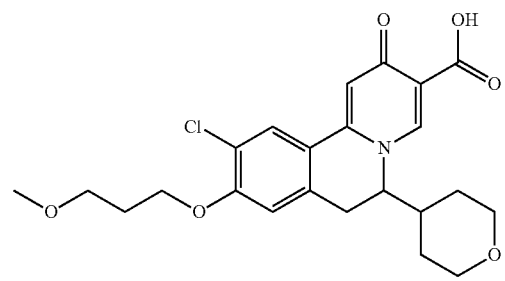 [SMILES: COCCCOc1cc2c(cc1Cl)-c1cc(=O)c(C(=O)O)cn1C(C1CCOCC1)C2]

Step 1: Preparation of
4-bromo-1-chloro-2-(3-methoxypropoxy)benzene

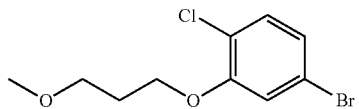

A mixture of 5-bromo-2-chloro-phenol (21 g, 0.1 mol), 1-bromo-3-methoxy-propane (16 g, 0.12 mol) and K$_2$CO$_3$ (28 g, 0.2 mol) in DMF (30 mL) was heated at 60° C. for 3 h. After being cooled to rt, the mixture was partitioned between water and ethyl acetate. The organic layer was dried over anhydrous Na$_2$SO$_4$ and concentrated to give 4-bromo-1-chloro-2-(3-methoxypropoxy)benzene(30 g) which was used directly in the next step.

Step 2: Preparation of 2-[4-chloro-3-(3-methoxy-propoxy)phenyl]-1-tetrahydropyran-4-yl-ethanone

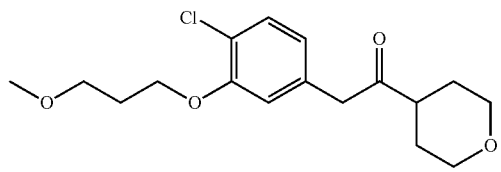 [SMILES: COCCCOc1cc(CC(=O)C2CCOCC2)ccc1Cl]

To a solution of 4-bromo-1-chloro-2-(3-methoxypropoxy) benzene (27.9 g, 0.1 mol) in THF (300 mL) was added 1-tetrahydropyran-4-ylethanone (25 g, 0.2 mol), Pd$_2$(dba)$_3$ (1.37 g, 1.5 mmol), Xantphos (1.74 g, 3.0 mmol) and sodium tert-butoxide (28 g, 0.3 mol). The resulting mixture was stirred for 8 h at 60° C. under argon atmosphere. After being cooled to rt, the resulting suspension was filtered with suction. The filter cake was poured into water and acidified to pH=3 with 2 M hydrochloride acid. The mixture was extracted with ethyl acetate (400 mL) 2 times and the combined organic layers were washed with water (200 mL) and brine, dried over anhydrous Na$_2$SO$_4$ and concentrated to give 2-[4-chloro-3-(3-methoxypropoxy)phenyl]-1-tetrahydropyran-4-yl-ethanone (30 g) as a yellow oil.

Step 3: Preparation of 2-[4-chloro-3-(3-methoxy-propoxy)phenyl]-1-tetrahydropyran-4-yl-ethanamine

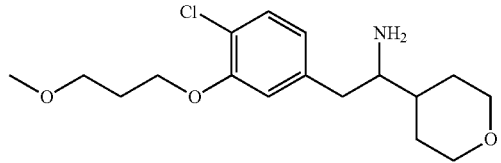 [SMILES: COCCCOc1cc(CC(N)C2CCOCC2)ccc1Cl]

To a solution of 2-[4-chloro-3-(3-methoxypropoxy)phenyl]-1-tetrahydropyran-4-yl-ethanone (30 g, 0.1 mol) in methanol (230 mL) was added ammonium acetate (77 g, 1 mol) and NaBH$_3$CN (12.6 g, 0.2 mmol). The resulting mixture was stirred for 12 h at room temperature. The reaction was quenched with water, and then 2.0 M NaOH aqueous solution (150 mL) was added. The resulting mixture was stirred for 1 h and extracted with ethyl acetate (450 mL). The organic layer was washed with water (200 mL) 2 times and brine, dried over anhydrous Na$_2$SO$_4$ and concentrated to give 2-[4-chloro-3-(3-methoxypropoxy)phenyl]-1-tetrahydropyran-4-yl-ethanamine (30 g) which was used in the next step without further purification.

Step 4: Preparation of N-[2-[4-chloro-3-(3-methoxypropoxy)phenyl]-1-tetrahydropyran-4-yl-ethyl]formamide

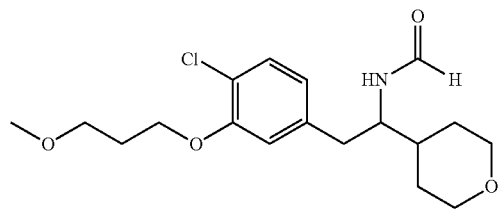 [SMILES: COCCCOc1cc(CC(NC=O)C2CCOCC2)ccc1Cl]

A mixture of 2-[4-chloro-3-(3-methoxypropoxy)phenyl]-1-tetrahydropyran-4-yl-ethanamine (30 g, 0.1 mmol) and formic acid (9.3 g, 0.2 mmol) in 1,4-dioxane (200 mL) was refluxed for 12 h and then concentrated under reduced pressure. The residue was dissolved in ethyl acetate (300 mL). Then the solution was washed with water (100 mL) 2 times and brine, dried over anhydrous Na$_2$SO$_4$ and concentrated to give N-[2-[4-chloro-3-(3-methoxypropoxy)phenyl]-1-tetrahydropyran-4-yl-ethyl]formamide (24.6 g).

Step 5: Preparation of 7-chloro-6-(3-methoxy-propoxy)-3-tetrahydropyran-4-yl-3,4-dihydroisoqui-noline

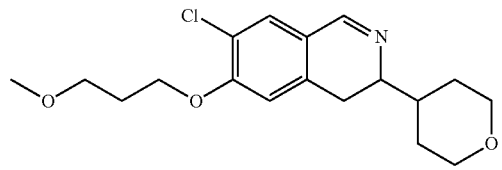 [SMILES: COCCCOc1cc2c(cc1Cl)C=NC(C1CCOCC1)C2]

To a solution of N-[2-[4-chloro-3-(3-methoxypropoxy) phenyl]-1-tetrahydropyran-4-yl-ethyl]formamide (24.9 g, 97.5 mmol) in acetonitrile (100 mL) was added POCl$_3$ (18 mL, 195 mmol) dropwise at 0-5° C. The mixture was refluxed for 3 h, then cooled to rt and concentrated. The residue was dissolved in ethyl acetate (100 mL), and to the solution aqueous ammonia was added to adjust the aqueous layer to pH around 11. The mixture was extracted with ethyl acetate (200 mL) 2 times, and then the organic layers were combined and concentrated. The residue was purified by column chromatography to give 7-chloro-6-(3-methoxy-propoxy)-3-tetrahydropyran-4-yl-3,4-dihydroisoquinoline (23 g).

Step 6: Preparation of ethyl 10-chloro-9-(3-methoxypropoxy)-2-oxo-6-tetrahydropyran-4-yl-1,6,7,11b-tetrahydrobenzo[a]quinolizine-3-carboxylate

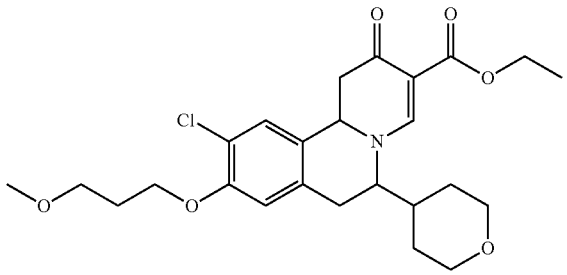

A mixture of 7-chloro-6-(3-methoxypropoxy)-3-tetrahydropyran-4-yl-3,4-dihydroisoquinoline (23 g, 97.5 mmol) and ethyl 2-(ethoxymethylene)-3-oxo-butanoate (36 g, 195 mmol) in ethanol (200 mL) was refluxed overnight. The mixture was then concentrated to give crude ethyl 10-chloro-9-(3-methoxypropoxy)-2-oxo-6-tetrahydropyran-4-yl-1,6,7,11b-tetrahydrobenzo[a]quinolizine-3-carboxylate as a dark brown oil which was used in the next step without purification.

Step 7: Preparation of ethyl 10-chloro-9-(3-methoxypropoxy)-2-oxo-6-tetrahydropyran-4-yl-6,7-dihydrobenzo[a]quinolizine-3-carboxylate

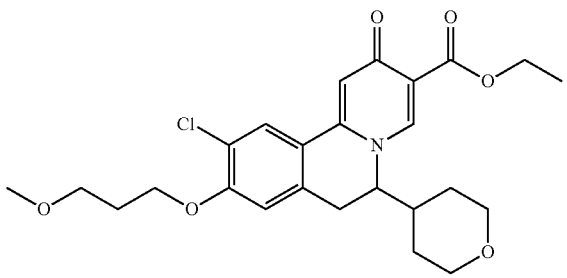 [SMILES: CCOC(=O)C1=CN2C(CC1=O)c1cc(Cl)c(OCCCOC)cc1CC2C1CCOCC1]

A mixture of crude ethyl 10-chloro-9-(3-methoxypropoxy)-2-oxo-6-tetrahydropyran-4-yl-1,6,7,11b-tetrahydrobenzo[a]quinolizine-3-carboxylate (25 g) and p-chloranil (14 g, 59 mmol) in DME (100 mL) was refluxed for 2 h. After being cooled to rt, the mixture was concentrated. The residue was dissolved in ethyl acetate (100 mL). The resulting mixture was washed with water (50 mL) 2 times and brine, dried over anhydrous Na$_2$SO$_4$ and concentrated to give crude ethyl 10-chloro-9-(3-methoxypropoxy)-2-oxo-6-tetrahydropyran-4-yl-6,7-dihydrobenzo[a]quinolizine-3-carboxylate which was used directly in the next step.

Step 8: Preparation of 10-chloro-9-(3-methoxypropoxy)-2-oxo-6-tetrahydropyran-4-yl-6,7-dihydrobenzo[a]quinolizine-3-carboxylic acid

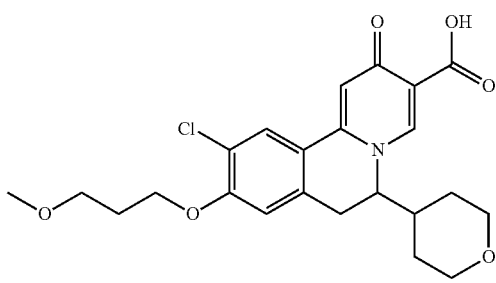 [SMILES: COCCCOc1cc2c(cc1Cl)-c1cc(=O)c(C(=O)O)cn1C(C1CCOCC1)C2]

To a solution of ethyl 10-chloro-9-(3-methoxypropoxy)-2-oxo-6-tetrahydropyran-4-yl-6,7-dihydrobenzo[a]quinolizine-3-carboxylate (5 g) in THF (30 mL) and methanol (150 mL) was added 2.0 M LiOH aqueous solution (70 mL) at rt. The resulting mixture was stirred for 4 hours at rt, and then acidified to pH=1-2 with 2 M hydrochloric acid. The mixture was extracted with DCM (200 mL) 2 times. The combined organic layers were washed with water and brine, dried over anhydrous Na$_2$SO$_4$ and concentrated to give a yellow solid, which was purified by column chromatography to give 10-chloro-9-(3-methoxypropoxy)-2-oxo-6-tetrahydropyran-4-yl-6,7-dihydrobenzo[a]quinolizine-3-carboxylic acid (500 mg). $^1$H NMR (400 MHz, DMSO-d6) δ 8.79 (s, 1H), 8.20 (s, 1H), 7.43 (s, 1H), 7.30 (s, 1H), 4.58 (m, 8.91 Hz, 1H), 4.14-4.28 (m, 2H), 3.72-3.85 (m, 2H), 3.52 (m, 2H), 3.21-3.32 (m, 5H), 2.94-3.13 (m, 2H), 1.96-2.09 (m, 2H), 1.56 (d, 2H), 1.36-1.46 (m, 1H), 1.16-1.32 (m, 1H), 0.94 (d, 1H). MS obsd. (ESI$^+$) [(M+H)$^+$]: 448.

Example 20

6-(1-Hydroxy-1-methyl-ethyl)-10-methoxy-9-(3-methoxypropoxy)-2-oxo-6,7-dihydrobenzo[a]quinolizine-3-carboxylic acid

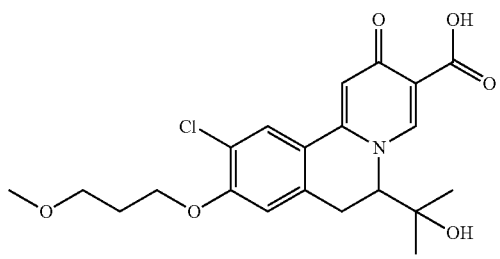 [SMILES: COCCCOc1cc2c(cc1Cl)-c1cc(=O)c(C(=O)O)cn1C(C(C)(C)O)C2]

Step 1: Preparation of 4-bromo-1-methoxy-2-(3-methoxypropoxy)benzene

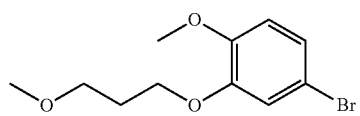

A 250 mL round-bottomed flask was charged with 5-bromo-2-methoxy-phenol (15.5 g, 76.4 mmol), 1-bromo-3-methoxy-propane (12.9 g, 84 mmol), K$_2$CO$_3$ (22 g, 2153 mmol) and DMF (50 mL). The resultant mixture was stirred at 50° C. for 3 hours, and then to the resulting mixture was added ethyl acetate and water. The organic phase was separated, and then dried over anhydrous Na$_2$SO$_4$ and concentrated to give 4-bromo-1-methoxy-2-(3-methoxypropoxy)benzene (23 g).

Step 2: Preparation of 3-hydroxy-1-[4-methoxy-3-(3-methoxypropoxy)phenyl]-3-methyl-butan-2-one

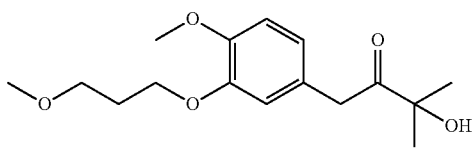 [SMILES: COCCCOc1cc(CC(=O)C(C)(C)O)ccc1OC]

To a solution of 4-bromo-1-methoxy-2-(3-methoxypropoxy)benzene (27.9 g, 0.1 mol) in THF (300 mL) was added 3-hydroxy-3-methyl-butan-2-one (20 g, 0.2 mol), Pd$_2$(dba)$_3$ (1.37 g, 1.5 mmol), Xantphos (1.74 g, 3.0 mmol) and sodium tert-butoxide (28 g, 0.3 mol). The resulting mixture was stirred for 8 h at 60° C. under argon atmosphere. After being cooled to rt, the resulting suspension was filtered with suction. The filter cake was poured into water. The resulting mixture was acidified to pH=3 with 2 M hydrochloride acid, and then extracted with ethyl acetate (400 mL) 2 times. The combined organic layers were washed with water (200 mL) and brine, dried over anhydrous Na$_2$SO$_4$ and concentrated to give 3-hydroxy-1-[4-methoxy-3-(3-methoxypropoxy)phenyl]-3-methyl-butan-2-one (28 g) as a yellow oil.

Step 3: Preparation of 3-amino-4-[4-methoxy-3-(3-methoxypropoxy)phenyl]-2-methyl-butan-2-ol

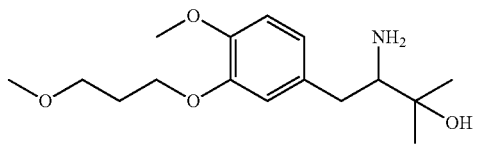 [SMILES: COCCCOc1cc(CC(N)C(C)(C)O)ccc1OC]

To a solution of 3-hydroxy-1-[4-methoxy-3-(3-methoxypropoxy)phenyl]-3-methyl-butan-2-one (30 g, 0.1 mol) in methanol (230 mL) was added ammonium acetate (77 g, 1 mol) and NaBH$_3$CN (12.6 g, 0.2 mmol). The resulting mixture was stirred for 12 h at room temperature. The reaction was quenched with water, and then to the resulting mixture was added 2.0 M NaOH aqueous solution (150 mL). The resulting mixture was stirred for 1 h and extracted with ethyl acetate (450 mL). The organic layer was washed with water (200 mL) 2 times and brine, dried over anhydrous Na$_2$SO$_4$ and concentrated to give 3-amino-4-[4-methoxy-3-(3-methoxypropoxy)phenyl]-2-methyl-butan-2-ol (28 g) which was used in the next step without further purification.

Step 4: Preparation of N-[2-hydroxy-1-[[4-methoxy-3-(3-methoxypropoxy)phenyl]methyl]-2-methyl-propyl]formamide

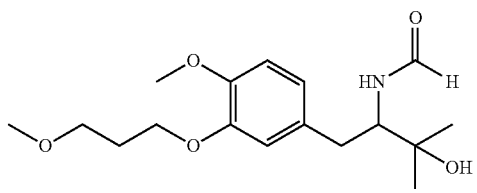 [SMILES: COCCCOc1cc(CC(NC=O)C(C)(C)O)ccc1OC]

A mixture of 3-amino-4-[4-methoxy-3-(3-methoxypropoxy)phenyl]-2-methyl-butan-2-ol (28 g, 0.1 mol) and formic acid (9.3 g, 0.2 mol) in 1,4-dioxane (200 mL) was refluxed for 12 h. The mixture was concentrated under reduced pressure, and the residue was dissolved in ethyl acetate (300 mL). The organic solution was washed with water (100 mL) 2 times and brine, dried over anhydrous Na$_2$SO$_4$ and concentrated to give N-[2-hydroxy-1-[[4-methoxy-3-(3-methoxypropoxy)phenyl]methyl]-2-methyl-propyl]formamide (18 g).

Step 5: Preparation of 2-[7-methoxy-6-(3-methoxypropoxy)-3,4-dihydroisoquinolin-3-yl]propan-2-ol

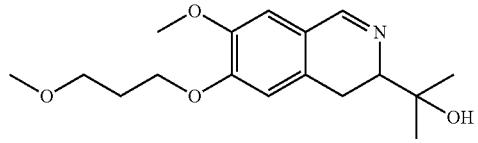 [SMILES: COCCCOc1cc2c(cc1OC)C=NC(C(C)(C)O)C2]

To a solution of N-[2-hydroxy-1-[[4-methoxy-3-(3-methoxypropoxy)phenyl]methyl]-2-methyl-propyl]formamide (18 g, 55 mmol) in acetonitrile (100 mL) was added POCl$_3$ (10 mL, 110 mmol) dropwise at 0-5° C. The resulting mixture was refluxed for 3 hours then cooled to room temperature. The solvent was removed by concentration and the residue was dissolved in ethyl acetate (100 mL). To the solution was added aqueous ammonia to adjust the aqueous layer to pH around 11. The mixture was extracted with ethyl acetate (200 mL) 2 times, and the organic layers were combined and concentrated. The residue was purified by column chromatography to give 2-[7-methoxy-6-(3-methoxypropoxy)-3,4-dihydroisoquinolin-3-yl]propan-2-ol (13 g).

Step 6: Preparation of ethyl 6-(1-hydroxy-1-methyl-ethyl)-10-methoxy-9-(3-methoxypropoxy)-2-oxo-1,6,7,11b-tetrahydrobenzo[a]quinolizine-3-carboxylate

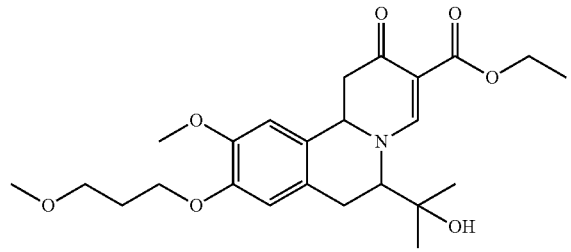 [SMILES: CCOC(=O)C1=CN2C(CC1=O)c1cc(OC)c(OCCCOC)cc1CC2C(C)(C)O]

A mixture of 2-[7-methoxy-6-(3-methoxypropoxy)-3,4-dihydroisoquinolin-3-yl]propan-2-ol (13 g, 42 mmol) and ethyl 2-(ethoxymethylene)-3-oxo-butanoate (24 g, 126 mmol) in ethanol (100 ml) was refluxed overnight. The mixture was concentrated to give crude ethyl 6-(1-hydroxy-1-methyl-ethyl)-10-methoxy-9-(3-methoxypropoxy)-2-oxo-1,6,7,11b-tetrahydrobenzo[a]quinolizine-3-carboxylate as a dark brown oil which was used in the next step without purification.

Step 7: Preparation of ethyl 6-(1-hydroxy-1-methyl-ethyl)-10-methoxy-9-(3-methoxypropoxy)-2-oxo-6,7-dihydrobenzo[a]quinolizine-3-carboxylate

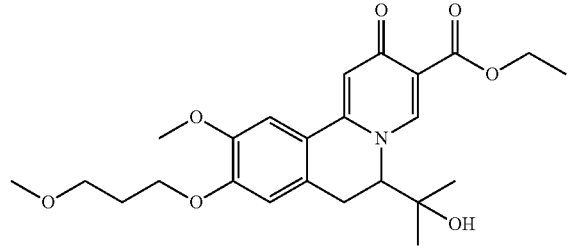 [SMILES: CCOC(=O)c1cn2c(cc1=O)-c1cc(OC)c(OCCCOC)cc1CC2C(C)(C)O]

A mixture of crude ethyl 6-(1-hydroxy-1-methyl-ethyl)-10-methoxy-9-(3-methoxypropoxy)-2-oxo-1,6,7,11b-tetrahydrobenzo[a]quinolizine-3-carboxylate (24 g) and p-chloranil (10 g, 42 mmol) in DME (100 mL) was refluxed for 2 h. After being cooled to rt, the mixture was concentrated. The residue was partitioned between ethyl acetate (100 mL) and water (50 mL). The separated organic layer was washed with water and brine, dried over anhydrous $Na_2SO_4$ and concentrated to give crude ethyl 6-(1-hydroxy-1-methyl-ethyl)-10-methoxy-9-(3-methoxypropoxy)-2-oxo-6,7-dihydrobenzo[a]quinolizine-3-carboxylate which was used directly in the next step.

Step 8: Preparation of 6-(1-hydroxy-1-methyl-ethyl)-10-methoxy-9-(3-methoxypropoxy)-2-oxo-6,7-dihydrobenzo[a]quinolizine-3-carboxylic acid (Example 20)

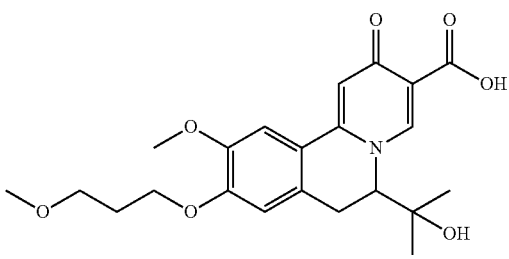 [SMILES: COCCCOc1cc2c(cc1OC)-c1cc(=O)c(C(=O)O)cn1C(C(C)(C)O)C2]

To a solution of ethyl 6-(1-hydroxy-1-methyl-ethyl)-10-methoxy-9-(3-methoxypropoxy)-2-oxo-6,7-dihydrobenzo[a]quinolizine-3-carboxylate (20 g) in THF (30 mL) and methanol (150 mL) was added 2.0 M LiOH aqueous solution (70 mL) at rt. The resulting mixture was stirred for 4 h, and then acidified to pH=1-2 with 2 M hydrochloric acid. The mixture was extracted with DCM (200 mL) 2 times. The combined organic layers were washed with water and brine, dried over anhydrous $Na_2SO_4$ and concentrated. The residue was purified by column chromatography to give 6-(1-hydroxy-1-methyl-ethyl)-10-methoxy-9-(3-methoxypropoxy)-2-oxo-6,7-dihydrobenzo[a]quinolizine-3-carboxylic acid (2 g) as a white solid. $^1$H NMR (400 MHz, DMSO-d6) δ 8.62 (s, 1H), 7.48 (s, 1H), 7.45 (s, 1H), 7.04 (s, 1H), 5.00 (s, 1H), 4.47 (d, 1H), 4.09 (d, 2H), 3.87 (s, 3H), 3.48 (s, 2H), 3.26 (s, 3H), 3.17 (m, 2H), 1.99 (m, 2H), 1.21 (s, 3H), 0.50 (s, 3H). MS obsd. (ESI$^+$) [(M+H)$^+$]: 418.

Example 21 and 22

(+)-6-(1-Hydroxy-1-methyl-ethyl)-10-methoxy-9-(3-methoxypropoxy)-2-oxo-6,7-dihydrobenzo[a]quinolizine-3-carboxylic acid and (−)-6-(1-hydroxy-1-methyl-ethyl)-10-methoxy-9-(3-methoxypropoxy)-2-oxo-6,7-dihydrobenzo[a]quinolizine-3-carboxylic acid

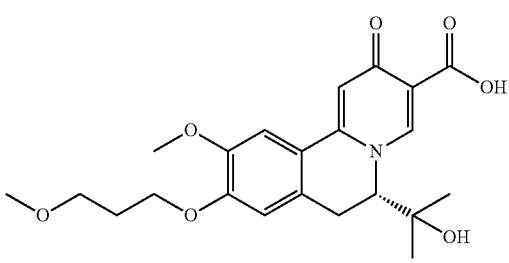

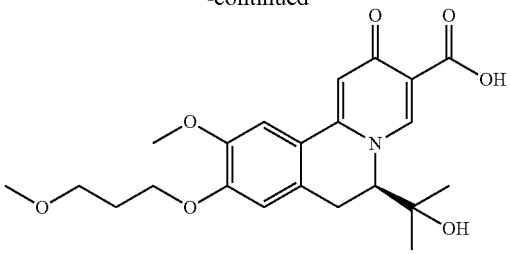

Separation of the racemic 6-(1-hydroxy-1-methyl-ethyl)-10-methoxy-9-(3-methoxypropoxy)-2-oxo-6,7-dihydrobenzo[a]quinolizine-3-carboxylic acid (40 mg, Example 20) by chiral HPLC afforded (+)-6-(1-hydroxy-1-methyl-ethyl)-10-methoxy-9-(3-methoxypropoxy)-2-oxo-6,7-dihydrobenzo[a]quinolizine-3-carboxylic acid (16 mg, Example 21) and (−)-6-(1-hydroxy-1-methyl-ethyl)-10-methoxy-9-(3-methoxypropoxy)-2-oxo-6,7-dihydrobenzo[a]quinolizine-3-carboxylic acid (12 mg, Example 22).

Example 21: $^1$H NMR (400 MHz, DMSO-d6): δ 8.62 (s, 1H), 7.48 (s, 1H), 7.45 (s, 1H), 7.04 (s, 1H), 5.00 (s, 1H), 4.47 (d, 1H), 4.09 (d, 2H), 3.87 (s, 3H), 3.48 (s, 2H), 3.26 (s, 3H), 3.17 (m, 2H), 1.99 (m, 2H), 1.21 (s, 3H), 0.50 (s, 3H); MS obsd. (ESI$^+$) [(M+H)$^+$]: 418; $[α]_D^{20}$=+97.143° (0.105%, $CH_3CN$).

Example 22: $^1$H NMR (400 MHz, DMSO-d6): δ 8.62 (s, 1H), 7.48 (s, 1H), 7.45 (s, 1H), 7.04 (s, 1H), 5.00 (s, 1H), 4.47 (d, 1H), 4.09 (d, 2H), 3.87 (s, 3H), 3.48 (s, 2H), 3.26 (s, 3H), 3.17 (m, 2H), 1.99 (m, 2H), 1.21 (s, 3H), 0.50 (s, 3H). MS obsd. (ESI$^+$) [(M+H)$^+$]: 418.

Example 23

6-(2-Benzyloxy-1,1-dimethyl-ethyl)-10-methoxy-9-(3-methoxypropoxy)-2-oxo-6,7-dihydrobenzo[a]quinolizine-3-carboxylic acid

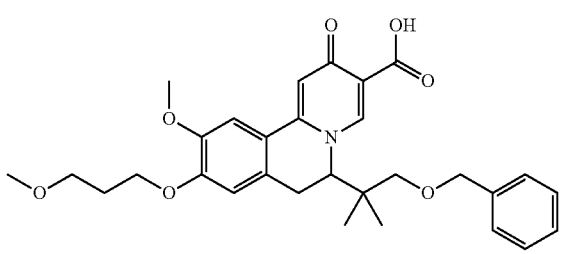 [SMILES: COCCCOc1cc2c(cc1OC)-c1cc(=O)c(C(=O)O)cn1C(C(C)(C)COCc1ccccc1)C2]

Step 1: Preparation of 4-benzyloxy-3,3-dimethyl-butan-2-one

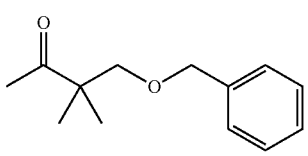

A mixture of 4-hydroxy-3,3-dimethyl-butan-2-one (16.6 g, 0.14 mol, from Step 1 of Example 1) and bromomethylbenzene (37 g, 0.28 mol) in DIPEA (28 g, 0.28 mol) was heated at 150° C. for 1 h. After being cooled to rt, the mixture was partitioned between ethyl acetate and water. The aqueous layer was adjusted to pH=1-2 with 2 M hydrochloride acid. Then the organic layer was separated, dried over anhydrous Na₂SO₄ and concentrated. The residue was purified by column chromatography to give 4-benzyloxy-3,3-dimethyl-butan-2-one (10 g).

Step 2: Preparation of 4-benzyloxy-1-[4-methoxy-3-(3-methoxypropoxy)phenyl]-3,3-dimethyl-butan-2-one

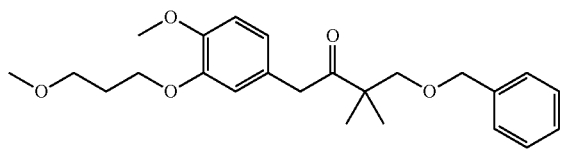 [SMILES: COCCCOc1cc(CC(=O)C(C)(C)COCc2ccccc2)ccc1OC]

To a solution of 4-bromo-1-methoxy-2-(3-methoxypropoxy)benzene (3.65 g, 13.3 mmol) in dioxane (30 mL) was added 4-benzyloxy-3,3-dimethyl-butan-2-one (5.5 g, 26.6 mmol), Pd(OAc)₂ (45 mg, 0.2 mmol), XPhos (191 mg, 0.4 mmol) and LiHMDS (30 mL, 1.3 M). The resulting mixture was stirred at 70° C. for 3 h under argon atmosphere. After being cooled to rt, the resulting suspension was poured into water and acidified to pH=3 with 2 M hydrochloride acid. The mixture was extracted with ethyl acetate (100 mL) 2 times. The combined organic layers were washed with water (100 mL) and brine, dried over anhydrous Na₂SO₄ and concentrated to give crude 4-benzyloxy-1-[4-methoxy-3-(3-methoxypropoxy)phenyl]-3,3-dimethyl-butan-2-one (9 g) as a yellow oil.

Step 3: Preparation of 4-benzyloxy-1-[4-methoxy-3-(3-methoxypropoxy)phenyl]-3,3-dimethyl-butan-2-amine

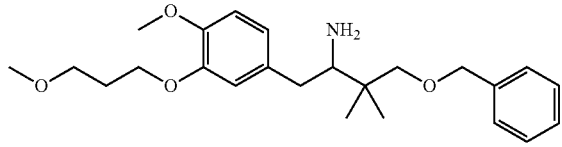 [SMILES: COCCCOc1cc(CC(N)C(C)(C)COCc2ccccc2)ccc1OC]

To a solution of crude 4-benzyloxy-1-[4-methoxy-3-(3-methoxypropoxy)phenyl]-3,3-dimethyl-butan-2-one (9 g, 13.3 mmol) in methanol (150 mL) was added ammonium acetate (15 g, 200 mmol) and NaBH₃CN (1.7 g, 26.6 mmol). The resulting mixture was stirred for 12 h at 60° C. The reaction was quenched with water, and then to the mixture was added 2.0 M NaOH aqueous solution (50 mL). The resulting mixture was stirred for 1 h, and then extracted with ethyl acetate (150 mL). The organic layer was washed with water (100 mL) 2 times and brine, dried over anhydrous Na₂SO₄ and concentrated to give 4-benzyloxy-1-[4-methoxy-3-(3-methoxypropoxy)phenyl]-3,3-dimethyl-butan-2-amine (5 g) which was used in the next step without further purification.

Step 4: Preparation of N-[3-benzyloxy-1-[[4-methoxy-3-(3-methoxypropoxy)phenyl]methyl]-2,2-dimethyl-propyl]formamide

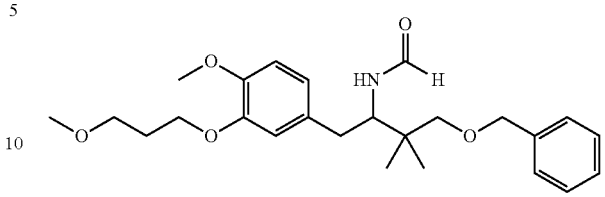

A mixture of 4-benzyloxy-1-[4-methoxy-3-(3-methoxypropoxy)phenyl]-3,3-dimethyl-butan-2-amine (5 g, 12.4 mmol) and formic acid (1.2 g, 25 mmol) in 1,4-dioxane (30 mL) was refluxed for 12 h. Then the mixture was concentrated under reduced pressure to give a red oil, which was then dissolved in ethyl acetate (30 mL). The solution was washed with water (30 mL) 2 times and brine, dried over anhydrous Na₂SO₄ and concentrated to give N-[3-benzyloxy-1-[[4-methoxy-3-(3-methoxypropoxy)phenyl]methyl]-2,2-dimethyl-propyl]formamide (6 g), which was used in the next step without further purification.

Step 5: Preparation of 3-(2-benzyloxy-1,1-dimethyl-ethyl)-7-methoxy-6-(3-methoxypropoxy)-3,4-dihydroisoquinoline

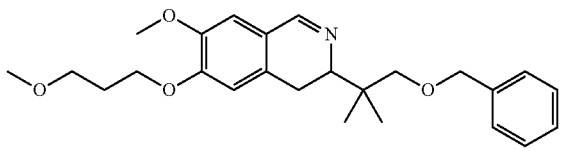 [SMILES: COCCCOc1cc2c(cc1OC)C=NC(C(C)(C)COCc1ccccc1)C2]

To a solution of N-[3-benzyloxy-1-[[4-methoxy-3-(3-methoxypropoxy)phenyl]methyl]-2,2-dimethyl-propyl]formamide (5.3 g, 12.3 mmol) in acetonitrile (50 mL) was added POCl₃ (2.3 mL, 24.6 mmol) dropwise at 0-5° C. The resulting mixture was heated to 60° C. and maintained at 60° C. for 1 h. After being cooled to rt, the mixture was concentrated. To the residue was added ethyl acetate (50 mL). Then to the resulting mixture was added ammonia water to adjust the pH of the aqueous phase to around 11. The mixture was extracted with ethyl acetate (50 mL) 2 times, and the organic layers were combined and concentrated. The residue was purified by column chromatography to give 3-(2-benzyloxy-1,1-dimethyl-ethyl)-7-methoxy-6-(3-methoxypropoxy)-3,4-dihydroisoquinoline (2.7 g).

Step 6: Preparation of ethyl 6-(2-benzyloxy-1,1-dimethyl-ethyl)-10-methoxy-9-(3-methoxypropoxy)-2-oxo-1,6,7,11b-tetrahydrobenzo[a]quinolizine-3-carboxylate

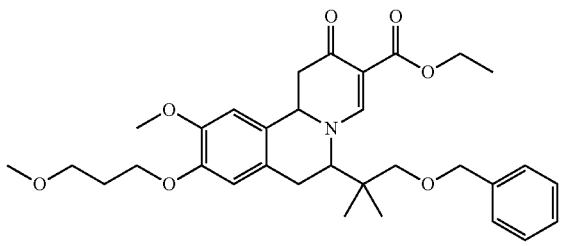 [SMILES: CCOC(=O)C1=CN2C(CC1=O)c1cc(OC)c(OCCCOC)cc1CC2C(C)(C)COCc1ccccc1]

A mixture of 3-(2-benzyloxy-1,1-dimethyl-ethyl)-7-methoxy-6-(3-methoxypropoxy)-3,4-dihydroisoquinoline (2.65 g, 6.4 mmol) and ethyl 2-(ethoxymethylene)-3-oxobutanoate (3.4 g, 19.3 mmol) in ethanol (50 mL) was refluxed overnight. Then the mixture was concentrated to give crude ethyl 6-(2-benzyloxy-1,1-dimethyl-ethyl)-10-methoxy-9-(3-methoxypropoxy)-2-oxo-1,6,7,11b-tetrahydrobenzo[a]quinolizine-3-carboxylate as a dark brown oil which was used in the next step without purification.

Step 7: Preparation of ethyl 6-(2-benzyloxy-1,1-dimethyl-ethyl)-10-methoxy-9-(3-methoxypropoxy)-2-oxo-6,7-dihydrobenzo[a]quinolizine-3-carboxylate

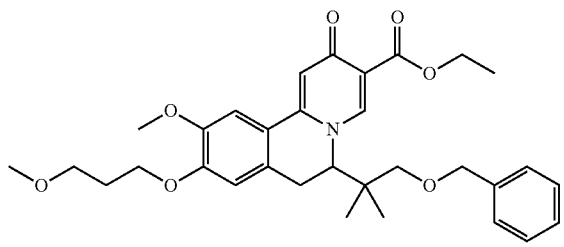 [SMILES: CCOC(=O)c1cn2c(cc1=O)-c1cc(OC)c(OCCCOC)cc1CC2C(C)(C)COCc1ccccc1]

A mixture of crude ethyl 6-(2-benzyloxy-1,1-dimethyl-ethyl)-10-methoxy-9-(3-methoxypropoxy)-2-oxo-1,6,7,11b-tetrahydrobenzo[a]quinolizine-3-carboxylate from step 6 and p-chloranil (1.6 g, 6.4 mmol) in DME (50 mL) was refluxed for 2 h. After being cooled to room temperature, the mixture was concentrated. The residue was dissolved in ethyl acetate (50 mL). The solution was washed with water (50 mL) 2 times and then washed with brine, dried over anhydrous Na$_2$SO$_4$ and concentrated to give crude ethyl 6-(2-benzyloxy-1,1-dimethyl-ethyl)-10-methoxy-9-(3-methoxypropoxy)-2-oxo-6,7-dihydrobenzo[a]quinolizine-3-carboxylate which was used directly in the next step.

Step 8: Preparation of 6-(2-benzyloxy-1,1-dimethyl-ethyl)-10-methoxy-9-(3-methoxypropoxy)-2-oxo-6,7-dihydrobenzo[a]quinolizine-3-carboxylic acid

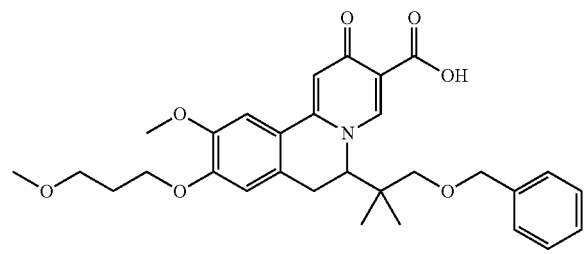 [SMILES: COCCCOc1cc2c(cc1OC)-c1cc(=O)c(C(=O)O)cn1C(C(C)(C)COCc1ccccc1)C2]

To a solution of crude ethyl 6-(2-benzyloxy-1,1-dimethyl-ethyl)-10-methoxy-9-(3-methoxypropoxy)-2-oxo-6,7-dihydrobenzo[a]quinolizine-3-carboxylate from step 7 in THF (10 mL) and methanol (15 mL) was added 2.0 M LiOH aqueous solution (10 mL) at rt. The resulting mixture was stirred for 4 h, and then acidified to pH=1-2 with 2 M hydrochloric acid. The mixture was extracted with DCM (30 mL) 2 times. The combined organic layers were washed with water and brine, dried over anhydrous Na$_2$SO$_4$ and concentrated. The residue was purified by column chromatography to give 6-(2-benzyloxy-1,1-dimethyl-ethyl)-10-methoxy-9-(3-methoxypropoxy)-2-oxo-6,7-dihydrobenzo[a]quinolizine-3-carboxylic acid (1.5 g) as a white solid. $^1$H NMR (400 MHz, DMSO-d6): δ 8.64 (s, 1H), 7.42 (m, 2H), 7.34 (s, 4H), 7.00-7.06 (m, 1H), 4.70 (m, 1H), 4.37-4.44 (m, 1H), 4.26-4.33 (m, 1H), 4.03-4.13 (m, 2H), 3.85 (s, 3H), 3.48 (m, 2H), 3.26 (s, 3H), 2.96-3.12 (m, 2H), 2.00 (m, 3H), 1.24 (s, 2H), 0.87 (s, 3H), 0.52 (s, 3H). MS obsd. (ESI$^+$) [(M+H)$^+$]: 522.

Example 24

6-(2-Hydroxy-1,1-dimethyl-ethyl)-10-methoxy-9-(3-methoxypropoxy)-2-oxo-6,7-dihydrobenzo[a]quinolizine-3-carboxylic acid

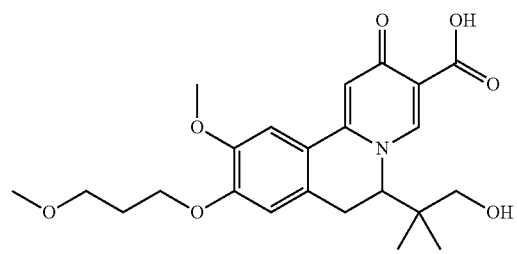 [SMILES: COCCCOc1cc2c(cc1OC)-c1cc(=O)c(C(=O)O)cn1C(C(C)(C)CO)C2]

To a mixture of 6-(2-benzyloxy-1,1-dimethyl-ethyl)-10-methoxy-9-(3-methoxypropoxy)-2-oxo-6,7-dihydrobenzo[a]quinolizine-3-carboxylic acid (100 mg) and Pd/C (10 mg) in ethanol (10 mL) was added Et$_3$SiH (1 mL). The mixture was heated at 80° C. for 3 h, and then additional Et$_3$SiH (1 mL) was added. After that, the mixture was heated at 80° C. overnight and then filtered. The filtrate was concentrated and the residue was purified by prep-HPLC to give 6-(2-hydroxy-1,1-dimethyl-ethyl)-10-methoxy-9-(3-methoxypropoxy)-2-oxo-6,7-dihydrobenzo[a]quinolizine-3-carboxylic acid (50 mg) as a white solid. $^1$H NMR (400 MHz, DMSO-d6): δ 8.68 (s, 1H), 7.46 (s, 1H), 7.43 (s, 1H), 7.08 (s, 1H), 5.08 (m, 1H), 4.67 (m, 1H), 4.10 (m, 2H), 3.87 (s, 3H), 3.48 (m, 2H), 3.33 (s, 3H), 3.19-3.25 (m, 2H), 2.96-3.11 (m, 2H), 1.99 (m, 2H), 0.76 (s, 3H), 0.40 (s, 3H). MS obsd. (ESI$^+$) [(M+H)$^+$]: 432.

Example 25 and 26

(+)-6-(2-Hydroxy-1,1-dimethyl-ethyl)-10-methoxy-9-(3-methoxypropoxy)-2-oxo-6,7-dihydrobenzo[a]quinolizine-3-carboxylic acid and (−)-6-(2-hydroxy-1,1-dimethyl-ethyl)-10-methoxy-9-(3-methoxypropoxy)-2-oxo-6,7-dihydrobenzo[a]quinolizine-3-carboxylic acid

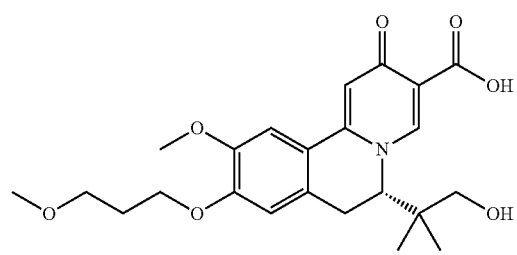

-continued

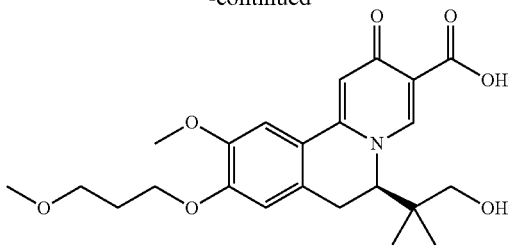

Separation of the racemic 6-(2-hydroxy-1,1-dimethyl-ethyl)-10-methoxy-9-(3-methoxypropoxy)-2-oxo-6,7-dihydrobenzo[a]quinolizine-3-carboxylic acid (100 mg, Example 24) by chiral HPLC afforded (+)-6-(2-hydroxy-1,1-dimethyl-ethyl)-10-methoxy-9-(3-methoxypropoxy)-2-oxo-6,7-dihydrobenzo[a]quinolizine-3-carboxylic acid (30 mg, Example 25) and (−)-6-(2-hydroxy-1,1-dimethyl-ethyl)-10-methoxy-9-(3-methoxypropoxy)-2-oxo-6,7-dihydrobenzo[a]quinolizine-3-carboxylic acid (28 mg, Example 26).

Example 25: $^1$H NMR (400 MHz, DMSO-d6): δ 8.68 (s, 1H), 7.46 (s, 1H), 7.43 (s, 1H), 7.08 (s, 1H), 5.08 (m, 1H), 4.67 (m, 1H), 4.10 (m, 2H), 3.87 (s, 3H), 3.48 (m, 2H), 3.33 (s, 3H), 3.19-3.25 (m, 2H), 2.96-3.11 (m, 2H), 1.99 (m, 2H), 0.76 (s, 3H), 0.40 (s, 3H). MS obsd. (ESI$^+$) [(M+H)$^+$]: 432. $[α]_D^{20}$=+90.00° (0.100%, CH$_3$CN).

Example 26: $^1$H NMR (400 MHz, DMSO-d6): δ 8.68 (s, 1H), 7.46 (s, 1H), 7.43 (s, 1H), 7.08 (s, 1H), 5.08 (m, 1H), 4.67 (m, 1H), 4.10 (m, 2H), 3.87 (s, 3H), 3.48 (m, 2H), 3.33 (s, 3H), 3.19-3.25 (m, 2H), 2.96-3.11 (m, 2H), 1.99 (m, 2H), 0.76 (s, 3H), 0.40 (s, 3H). MS obsd. (ESI$^+$) [(M+H)$^+$]: 432.

Example 27

10-Methoxy-6-(2-methoxy-1,1-dimethyl-ethyl)-9-(3-methoxypropoxy)-2-oxo-6,7-dihydrobenzo[a]quinolizine-3-carboxylic acid

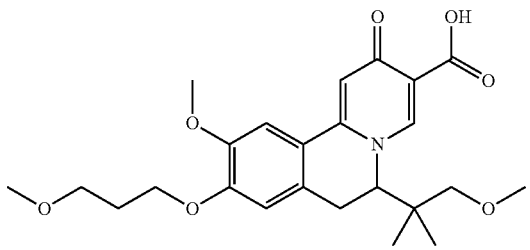

Step 1: Preparation of 4-methoxy-1-[4-methoxy-3-(3-methoxypropoxy)phenyl]-3,3-dimethyl-butan-2-one

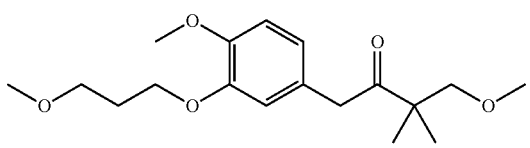

To a solution of 4-bromo-1-methoxy-2-(3-methoxypropoxy)benzene (100 g, 0.37 mol) in dioxane (100 mL) was added 4-methoxy-3,3-dimethyl-butan-2-one (100 g, 0.73 mol), Pd(OAc)$_2$ (1.23 g, 5.5 mmol), XPhos (5.2 g, 11 mmol) and LiHMDS (850 mL, 1.3 M). The resulting mixture was stirred at 70° C. for 3 h under argon atmosphere. After being cooled to room temperature, the resulting suspension was poured into water and acidified to pH=3 with 2 M hydrochloride acid. The mixture was extracted with ethyl acetate (500 mL) 2 times. The combined organic layers were washed with water (200 mL) and brine, dried over anhydrous Na$_2$SO$_4$ and concentrated to give crude 4-methoxy-1-[4-methoxy-3-(3-methoxypropoxy)phenyl]-3,3-dimethyl-butan-2-one (120 g) as a yellow oil.

Step 2: Preparation of 4-methoxy-1-[4-methoxy-3-(3-methoxypropoxy)phenyl]-3,3-dimethyl-butan-2-amine

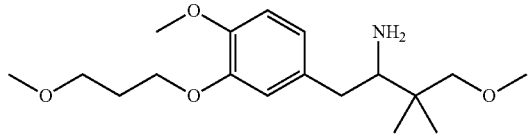

To a solution of crude 4-methoxy-1-[4-methoxy-3-(3-methoxypropoxy)phenyl]-3,3-dimethyl-butan-2-one (120 g, 0.37 mol) in methanol (500 mL) was added ammonium acetate (280 g, 3.65 mol) and NaBH$_3$CN (46 g, 0.73 mol). The resulting mixture was stirred for 12 h at 60° C. The reaction was quenched with water, and then to the mixture was added 2.0 M NaOH aqueous solution (50 mL). The mixture was stirred for 1 h, adjusted to pH=1 with concentrated hydrochloric acid and then extracted with ethyl acetate (200 mL). The aqueous phase was adjusted to pH=12 with potassium hydroxide aqueous solution and extracted with ethyl acetate (500 mL) 2 times. The combined organic layers were washed with water (200 mL) 2 times and brine, dried over anhydrous Na$_2$SO$_4$ and concentrated to give 4-methoxy-1-[4-methoxy-3-(3-methoxypropoxy)phenyl]-3,3-dimethyl-butan-2-amine (120 g).

Step 3: Preparation of N-[3-methoxy-1-[[4-methoxy-3-(3-methoxypropoxy)phenyl]methyl]-2,2-dimethyl-propyl]formamide

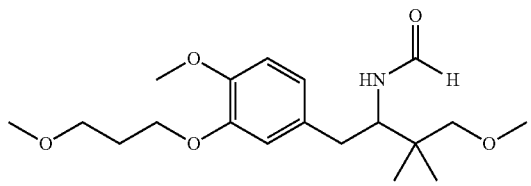

A mixture of 4-methoxy-1-[4-methoxy-3-(3-methoxypropoxy)phenyl]-3,3-dimethyl-butan-2-amine (120 g, 0.37 mol), formic acid (150 mL) and triethyl orthoformate (60 mL) in 1,4-dioxane (500 mL) was refluxed for 48 h and then concentrated. The residue was partitioned between ethyl acetate (500 mL) and water (200 mL). The organic layer was washed with water and brine, dried over anhydrous Na$_2$SO$_4$ and concentrated to give N-[3-methoxy-1-[[4-methoxy-3-(3-methoxypropoxy)phenyl]methyl]-2,2-dimethyl-propyl]formamide (120 g).

Step 4: Preparation of 7-methoxy-3-(2-methoxy-1,1-dimethyl-ethyl)-6-(3-methoxypropoxy)-3,4-dihydroisoquinoline

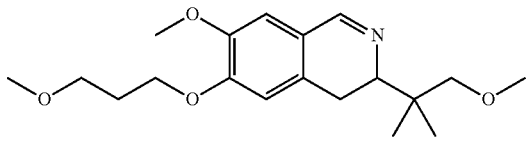

To a solution of N-[3-methoxy-1-[[4-methoxy-3-(3-methoxypropoxy)phenyl]methyl]-2,2-dimethyl-propyl]formamide (120 g, 0.34 mol) in acetonitrile (500 mL) was added POCl$_3$ (64 mL, 0.68 mol) dropwise at 0-5° C. The resulting mixture was heated at 60° C. for 1 h. After being cooled to rt, the mixture was concentrated. To the residue was added ethyl acetate (500 mL), then to the resulting mixture was added ammonia water to adjust the pH of the aqueous solution to around 11. The mixture was extracted with ethyl acetate (300 mL) 2 times. The organic layers were combined and concentrated. The residue was purified by column chromatography to 7-methoxy-3-(2-methoxy-1,1-dimethyl-ethyl)-6-(3-methoxypropoxy)-3,4-dihydroisoquinoline (89 g).

Step 5: Preparation of ethyl 10-methoxy-6-(2-methoxy-1,1-dimethyl-ethyl)-9-(3-methoxypropoxy)-2-oxo-1,6,7,11b-tetrahydrobenzo[a]quinolizine-3-carboxylate

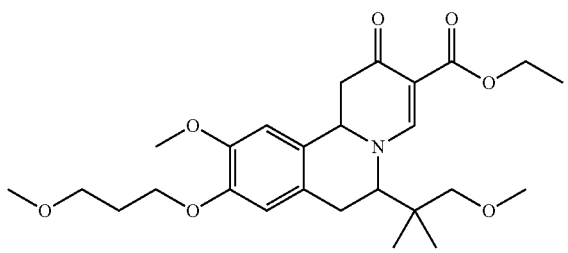 [SMILES: CCOC(=O)C1=CN2C(CC1=O)c1cc(OC)c(OCCCOC)cc1CC2C(C)(C)COC]

A mixture of 7-methoxy-3-(2-methoxy-1,1-dimethyl-ethyl)-6-(3-methoxypropoxy)-3,4-dihydroisoquinoline (87 g, 0.26 mol) and ethyl 2-(ethoxymethylene)-3-oxo-butanoate (144 g, 0.78 mol) in ethanol (500 mL) was refluxed 48 h. The mixture was concentrated to give crude ethyl 10-methoxy-6-(2-methoxy-1,1-dimethyl-ethyl)-9-(3-methoxypropoxy)-2-oxo-1,6,7,11b-tetrahydrobenzo[a]quinolizine-3-carboxylate which was used in the next step without purification.

Step 6: Preparation of ethyl 10-methoxy-6-(2-methoxy-1,1-dimethyl-ethyl)-9-(3-methoxypropoxy)-2-oxo-6,7-dihydrobenzo[a]quinolizine-3-carboxylate

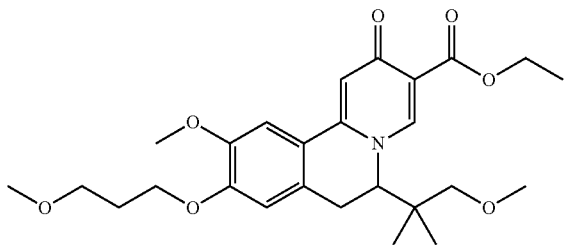 [SMILES: CCOC(=O)c1cn2c(cc1=O)-c1cc(OC)c(OCCCOC)cc1CC2C(C)(C)COC]

A mixture of crude ethyl 10-methoxy-6-(2-methoxy-1,1-dimethyl-ethyl)-9-(3-methoxypropoxy)-2-oxo-1,6,7,11b-tetrahydrobenzo[a]quinolizine-3-carboxylate from step 5 and p-chloranil (50 g, 0.21 mol) in DME (500 mL) was refluxed for 2 h. After being cooled to room temperature, the mixture was concentrated. The residue was dissolved in ethyl acetate (500 mL). And then the solution was washed with water (200 mL) 2 times and brine, dried over anhydrous Na$_2$SO$_4$ and concentrated to give crude ethyl 10-methoxy-6-(2-methoxy-1,1-dimethyl-ethyl)-9-(3-methoxypropoxy)-2-oxo-6,7-dihydrobenzo[a]quinolizine-3-carboxylate which was used directly in the next step.

Step 7: Preparation of 10-methoxy-6-(2-methoxy-1,1-dimethyl-ethyl)-9-(3-methoxypropoxy)-2-oxo-6,7-dihydrobenzo[a]quinolizine-3-carboxylic acid

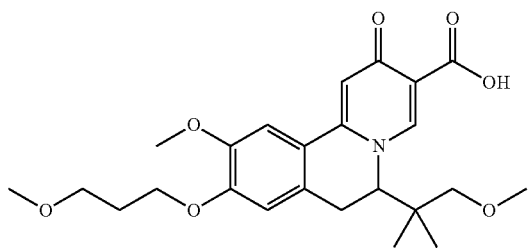

To a solution of crude ethyl 6-(2-benzyloxy-1,1-dimethyl-ethyl)-10-methoxy-9-(3-methoxypropoxy)-2-oxo-6,7-dihydrobenzo[a]quinolizine-3-carboxylate from step 6 in THF (200 mL) and ethanol (200 mL) was added 2.0 M LiOH aqueous solution (200 mL) at rt. The resulting mixture was stirred for 4 h, and then acidified to pH=1-2 with 2 M hydrochloric acid. The mixture was extracted with DCM (500 mL) 2 times. The combined organic layers were washed with water and brine, dried over anhydrous Na$_2$SO$_4$ and concentrated. The residue was purified by column chromatography to give 10-methoxy-6-(2-methoxy-1,1-dimethyl-ethyl)-9-(3-methoxypropoxy)-2-oxo-6,7-dihydrobenzo[a]quinolizine-3-carboxylic acid (50 g) as white solid. $^1$H NMR (400 MHz, DMSO-d6): δ 8.56 (s, 1H), 7.47 (s, 1H), 7.43 (s, 1H), 7.08 (s, 1H), 4.64 (m, 1H), 4.01-4.19 (m, 2H), 3.87 (s, 3H), 3.48 (m, 2H), 3.26 (s, 3H), 3.18-3.24 (m, 2H), 2.80-3.01 (m, 2H), 1.99 (m, 2H), 0.87 (s, 3H), 0.46 (s, 3H). MS obsd. (ESI$^+$) [(M+H)$^+$]: 446.

Example 28 and 29

(+)-10-Methoxy-6-(2-methoxy-1,1-dimethyl-ethyl)-9-(3-methoxypropoxy)-2-oxo-6,7-dihydrobenzo[a]quinolizine-3-carboxylic acid and (+10-methoxy-6-(2-methoxy-1,1-dimethyl-ethyl)-9-(3-methoxypropoxy)-2-oxo-6,7-dihydrobenzo[a]quinolizine-3-carboxylic acid

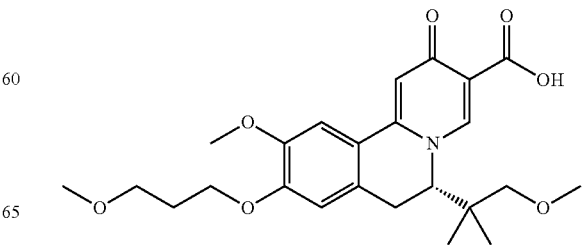

-continued

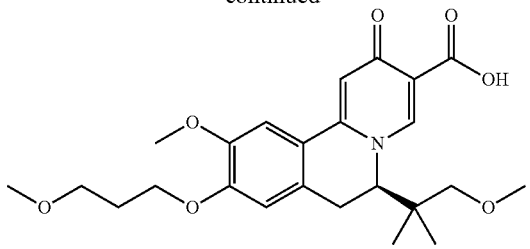

Separation of the racemic 10-methoxy-6-(2-methoxy-1,1-dimethyl-ethyl)-9-(3-methoxypropoxy)-2-oxo-6,7-dihydrobenzo[a]quinolizine-3-carboxylic acid (50 g) by chiral HPLC afforded (+)-10-methoxy-6-(2-methoxy-1,1-dimethyl-ethyl)-9-(3-methoxypropoxy)-2-oxo-6,7-dihydrobenzo[a]quinolizine-3-carboxylic acid (22 g, Example 28) and (−)-10-methoxy-6-(2-methoxy-1,1-dimethyl-ethyl)-9-(3-methoxypropoxy)-2-oxo-6,7-dihydrobenzo[a]quinolizine-3-carboxylic acid (22 g, Example 29).

Example 28: $^1$H NMR (400 MHz, DMSO-d6): δ 8.56 (s, 1H), 7.47 (s, 1H), 7.43 (s, 1H), 7.08 (s, 1H), 4.64 (m, 1H), 4.01-4.19 (m, 2H), 3.87 (s, 3H), 3.48 (m, 2H), 3.26 (s, 3H), 3.18-3.24 (m, 2H), 2.80-3.01 (m, 2H), 1.99 (m, 2H), 0.87 (s, 3H), 0.46 (s, 3H). MS obsd. (ESI$^+$) [(M+H)$^+$]: 446. [α]$_D^{20}$=+89.314° (0.063%, CH$_3$CN).

Example 29: $^1$H NMR (400 MHz, DMSO-d6): δ 8.56 (s, 1H), 7.47 (s, 1H), 7.43 (s, 1H), 7.08 (s, 1H), 4.64 (m, 1H), 4.01-4.19 (m, 2H), 3.87 (s, 3H), 3.48 (m, 2H), 3.26 (s, 3H), 3.18-3.24 (m, 2H), 2.80-3.01 (m, 2H), 1.99 (m, 2H), 0.87 (s, 3H), 0.46 (s, 3H). MS obsd. (ESI$^+$) [(M+H)$^+$]: 446.

Example 30

10-Chloro-6-(2-methoxy-1,1-dimethyl-ethyl)-9-(3-methoxypropoxy)-2-oxo-6,7-dihydrobenzo[a]quinolizine-3-carboxylic acid

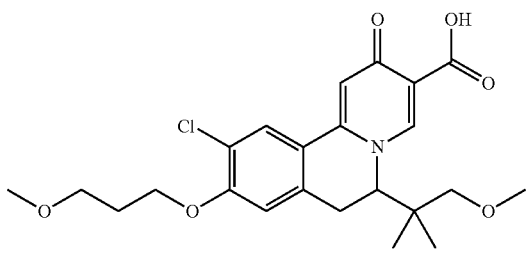

Step 1: Preparation of 4-chloro-1-[4-methoxy-3-(3-methoxypropoxy)phenyl]-3,3-dimethyl-butan-2-one

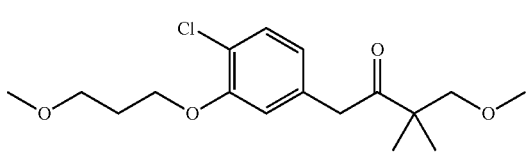

To a solution of 4-bromo-1-chloro-2-(3-methoxypropoxy)benzene (20 g, 72 mmol) in dioxane (50 mL) was added 4-methoxy-3,3-dimethyl-butan-2-one (19 g, 144 mmol), Pd(OAc)$_2$ (0.24 g, 1 mmol), XPhos (1 g, 2.16 mmol) and LiHMDS (166 mL, 1.3 M). The resulting mixture was stirred at 70° C. for 3 h under argon atmosphere. After being cooled to room temperature, the suspension was poured into water. The mixture was acidified to pH=3 with 2 M hydrochloride acid, and then extracted with ethyl acetate (200 mL) 2 times. The combined organic layers were washed with water (80 mL) and brine, dried over anhydrous Na$_2$SO$_4$ and concentrated to give crude 4-chloro-1-[4-methoxy-3-(3-methoxypropoxy)phenyl]-3,3-dimethyl-butan-2-one (24 g) as a yellow oil.

Step 2: Preparation of 4-chloro-1-[4-methoxy-3-(3-methoxypropoxy)phenyl]-3,3-dimethyl-butan-2-amine

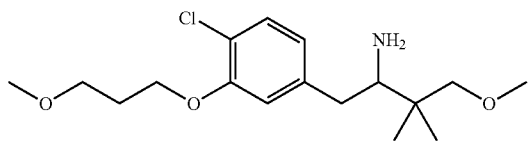

To a solution of crude 4-chloro-1-[4-methoxy-3-(3-methoxypropoxy)phenyl]-3,3-dimethyl-butan-2-one (24 g, 72 mmol) in methanol (200 mL) was added ammonium acetate (55 g, 720 mmol) and NaBH$_3$CN (9 g, 144 mmol). The resulting mixture was stirred for 12 h at 60° C. The reaction was quenched with water, and then to the mixture was added 2.0 M NaOH aqueous solution (20 mL). The mixture was stirred for 1 h, and then adjusted to pH=1 with concentrated hydrochloric acid. After being washed with ethyl acetate (100 mL) to remove impurities, the separated aqueous phase was adjusted to pH=12 with potassium hydroxide and then extracted with ethyl acetate (200 mL) 2 times. The combined organic layers were washed with water (80 mL) 2 times and brine, dried over anhydrous Na$_2$SO$_4$ and concentrated to give 4-chloro-1-[4-methoxy-3-(3-methoxypropoxy)phenyl]-3,3-dimethyl-butan-2-amine (25 g).

Step 3: Preparation of N-[1-[[4-chloro-3-(3-methoxypropoxy)phenyl]methyl]-3-methoxy-2,2-dimethyl-propyl]formamide

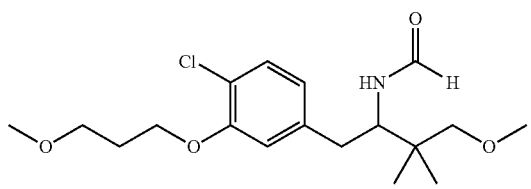

A mixture of 4-chloro-1-[4-methoxy-3-(3-methoxypropoxy)phenyl]-3,3-dimethyl-butan-2-amine (25 g, 72 mmol), formic acid (30 mL) and triethyl orthoformate (10 mL) in 1,4-dioxane (200 mL) was refluxed for 48 h and then concentrated under reduced pressure. The residue was partitioned between ethyl acetate (200 mL) and water (50 mL). The separated organic layer was washed with water and brine, dried over anhydrous Na$_2$SO$_4$ and concentrated to give N-[1-[[4-chloro-3-(3-methoxypropoxy)phenyl]methyl]-3-methoxy-2,2-dimethyl-propyl]formamide (25 g) which was used in the next step without further purification.

Step 4: Preparation of 7-chloro-3-(2-methoxy-1,1-dimethyl-ethyl)-6-(3-methoxypropoxy)-3,4-dihydroisoquinoline

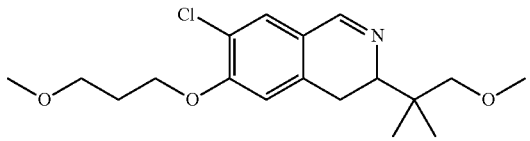

To a solution of N-[1-[[4-chloro-3-(3-methoxypropoxy)phenyl]methyl]-3-methoxy-2,2-dimethyl-propyl]formamide (24 g, 72 mmol) in acetonitrile (200 mL) was added POCl$_3$ (14 mL, 144 mmol) dropwise at 0-5° C. The resulting mixture was warmed at 60° C. for 1 h. After being cooled to rt, the mixture was concentrated. To the residue ethyl acetate (200 mL) was added, then to the mixture was added ammonia water to adjust the pH of the aqueous solution to around 11. The mixture was extracted with ethyl acetate (200 mL) 2 times. The organic layers were combined and concentrated. The residue was purified by column chromatography to 7-chloro-3-(2-methoxy-1,1-dimethyl-ethyl)-6-(3-methoxypropoxy)-3,4-dihydroisoquinoline (21 g).

Step 5: Preparation of ethyl 10-chloro-6-(2-methoxy-1,1-dimethyl-ethyl)-9-(3-methoxypropoxy)-2-oxo-1,6,7,11b-tetrahydrobenzo[a]quinolizine-3-carboxylate

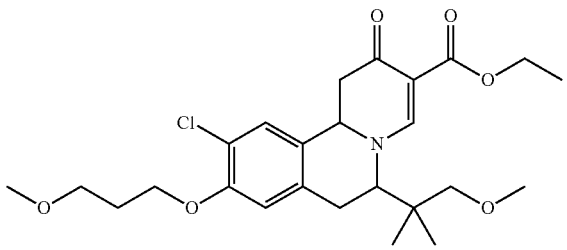 [SMILES: CCOC(=O)C1=CN2C(CC1=O)c1cc(Cl)c(OCCCOC)cc1CC2C(C)(C)COC]

A mixture of 7-chloro-3-(2-methoxy-1,1-dimethyl-ethyl)-6-(3-methoxypropoxy)-3,4-dihydroisoquinoline (21 g, 62 mmol) and ethyl 2-(ethoxymethylene)-3-oxo-butanoate (34 g, 185 mmol) in ethanol (100 mL) was refluxed for 24 h. The mixture was concentrated to give crude ethyl 10-chloro-6-(2-methoxy-1,1-dimethyl-ethyl)-9-(3-methoxypropoxy)-2-oxo-1,6,7,11b-tetrahydrobenzo[a]quinolizine-3-carboxylate as a dark brown oil which was used in the next step without purification.

Step 6: Preparation of ethyl 10-chloro-6-(2-methoxy-1,1-dimethyl-ethyl)-9-(3-methoxypropoxy)-2-oxo-6,7-dihydrobenzo[a]quinolizine-3-carboxylate

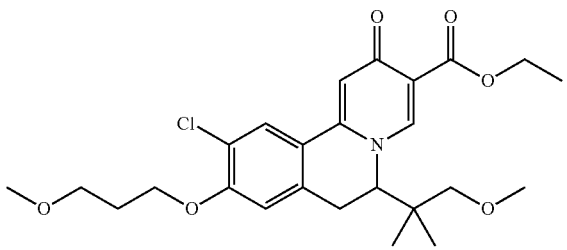 [SMILES: CCOC(=O)c1cn2c(cc1=O)-c1cc(Cl)c(OCCCOC)cc1CC2C(C)(C)COC]

A mixture of crude ethyl 10-chloro-6-(2-methoxy-1,1-dimethyl-ethyl)-9-(3-methoxypropoxy)-2-oxo-1,6,7,11b-tetrahydrobenzo[a]quinolizine-3-carboxylate from step 5 and p-chloranil (15 g, 62 mmol) in DME (100 mL) was refluxed for 2 h. After being cooled to rt, the mixture was concentrated. The residue was dissolved in ethyl acetate (500 mL). The solution was washed with water (200 mL) 2 times and brine, dried over anhydrous Na$_2$SO$_4$ and concentrated to give crude ethyl 10-chloro-6-(2-methoxy-1,1-dimethyl-ethyl)-9-(3-methoxypropoxy)-2-oxo-6,7-dihydrobenzo[a]quinolizine-3-carboxylate which was used directly in the next step.

Step 7: Preparation of 10-chloro-6-(2-methoxy-1,1-dimethyl-ethyl)-9-(3-methoxypropoxy)-2-oxo-6,7-dihydrobenzo[a]quinolizine-3-carboxylic acid

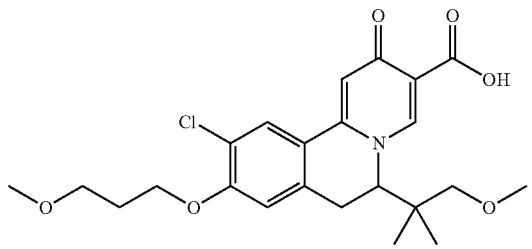

To a solution of crude ethyl 10-chloro-6-(2-methoxy-1,1-dimethyl-ethyl)-9-(3-methoxypropoxy)-2-oxo-6,7-dihydrobenzo[a]quinolizine-3-carboxylate in THF (50 mL) and ethanol (50 mL) was added 2.0 M LiOH aqueous solution (50 mL) at rt. The resulting mixture was stirred for 4 h, and then acidified to pH=1-2 with 2 M hydrochloric acid. The mixture was extracted with DCM (100 mL) 2 times. The combined organic layers were washed with water and brine, dried over anhydrous Na$_2$SO$_4$ and concentrated. The residue was purified by column chromatography to give 10-chloro-6-(2-methoxy-1,1-dimethyl-ethyl)-9-(3-methoxypropoxy)-2-oxo-6,7-dihydrobenzo[a]quinolizine-3-carboxylic acid (4.1 g) as a white solid. $^1$H NMR (400 MHz, DMSO-d6): δ 8.56 (s, 1H), 8.15 (s, 1H), 7.37 (s, 1H), 7.31 (s, 1H), 4.68 (m, 1H), 4.13-4.32 (m, 2H), 3.52 (m, 2H), 3.27 (s, 3H), 3.12 (s, 3H), 2.94 (s, 1H), 2.90 (s, 1H), 2.82 (m, 1H), 2.00-2.12 (m, 2H), 1.97-2.09 (m, 3H), 1.69-1.83 (m, 1H), 0.88 (s, 3H), 0.47 (s, 3H). MS obsd. (ESI$^+$) [(M+H)$^+$]: 450.

Example 31 and 32

(+)-10-Chloro-6-(2-methoxy-1,1-dimethyl-ethyl)-9-(3-methoxypropoxy)-2-oxo-6,7-dihydrobenzo[a]quinolizine-3-carboxylic acid and (−)-10-chloro-6-(2-methoxy-1,1-dimethyl-ethyl)-9-(3-methoxypropoxy)-2-oxo-6,7-dihydrobenzo[a]quinolizine-3-carboxylic acid

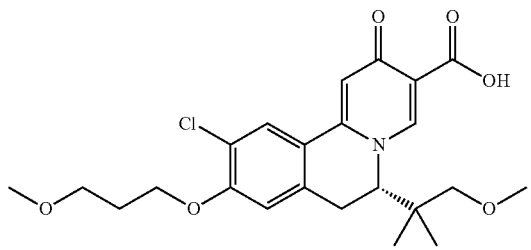

-continued

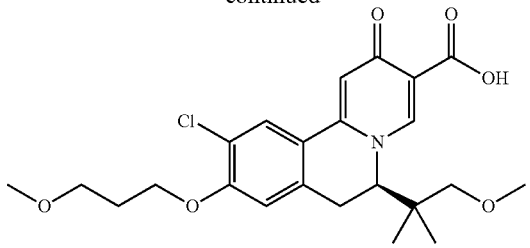

Separation of the racemic 10-chloro-6-(2-methoxy-1,1-dimethyl-ethyl)-9-(3-methoxypropoxy)-2-oxo-6,7-dihydrobenzo[a]quinolizine-3-carboxylic acid (2 g, Example 30) by chiral HPLC afforded (+)-10-chloro-6-(2-methoxy-1,1-dimethyl-ethyl)-9-(3-methoxypropoxy)-2-oxo-6,7-dihydrobenzo[a]quinolizine-3-carboxylic acid (750 mg, Example 31) and (−)-10-chloro-6-(2-methoxy-1,1-dimethyl-ethyl)-9-(3-methoxypropoxy)-2-oxo-6,7-dihydrobenzo[a]quinolizine-3-carboxylic acid (680 mg, Example 32).

Example 31: $^1$H NMR (400 MHz, DMSO-d6): δ 8.56 (s, 1H), 8.15 (s, 1H), 7.37 (s, 1H), 7.31 (s, 1H), 4.68 (m, 1H), 4.13-4.32 (m, 2H), 3.52 (m, 2H), 3.27 (s, 3H), 3.12 (s, 3H), 2.94 (s, 1H), 2.90 (s, 1H), 2.82 (m, 1H), 2.00-2.12 (m, 2H), 1.97-2.09 (m, 3H), 1.69-1.83 (m, 1H), 0.88 (s, 3H), 0.47 (s, 3H). MS obsd. (ESI$^+$) [(M+H)$^+$]: 450. [α]$_D^{20}$=+96.000° (0.100%, CH$_3$CN).

Example 32: $^1$H NMR (400 MHz, DMSO-d6): δ 8.56 (s, 1H), 8.15 (s, 1H), 7.37 (s, 1H), 7.31 (s, 1H), 4.68 (m, 1H), 4.13-4.32 (m, 2H), 3.52 (m, 2H), 3.27 (s, 3H), 3.12 (s, 3H), 2.94 (s, 1H), 2.90 (s, 1H), 2.82 (m, 1H), 2.00-2.12 (m, 2H), 1.97-2.09 (m, 3H), 1.69-1.83 (m, 1H), 0.88 (s, 3H), 0.47 (s, 3H). MS obsd. (ESI$^+$) [(M+H)$^+$]: 450.

Example 33

10-Chloro-9-(2-methoxyethoxy)-6-(methylsulfanylmethyl)-2-oxo-6,7-dihydrobenzo[a]quinolizine-3-carboxylic acid

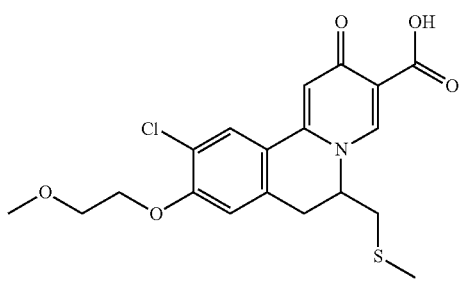 [SMILES: COCCOc1cc2c(cc1Cl)-c1cc(=O)c(C(=O)O)cn1C(CSC)C2]

Step 1: Preparation of 4-allyl-1-chloro-2-(2-methoxyethoxy)benzene

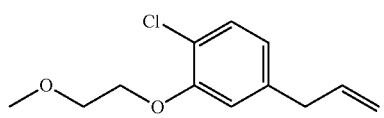

To a solution of 4-bromo-1-chloro-2-(2-methoxyethoxy)benzene (2.64 g, 10.0 mmol) in anhydrous THF (300 mL) was added 2-allyl-4,4,5,5-tetramethyl-1,3,2-dioxaborolane (3.36 g, 20.0 mmol), CsF (6.08 g, 40.0 mmol) and tetrakis(triphenylphosphine)palladium(0) (2.30 g, 2.0 mmol). The mixture was stirred for 16 hours at 70° C. under argon atmosphere. After LC/MS indicated the starting material of 4-bromo-1-chloro-2-(2-methoxyethoxy)benzene was consumed completely, the reaction mixture was cooled to rt and then partitioned between DCM and water. The organic layer was dried over anhydrous Na$_2$SO$_4$ and concentrated. The residue was purified by column chromatography to give 4-allyl-1-chloro-2-(2-methoxyethoxy)benzene (1.4 g).

Step 2: Preparation of 2-[[4-chloro-3-(2-methoxyethoxy)phenyl]methyl]-1-(p-tolylsulfonyl)aziridine

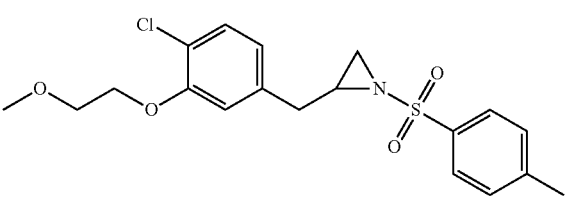

To a solution of 4-allyl-1-chloro-2-(2-methoxyethoxy)benzene (500 mg, 2.2 mmol) in MeCN was added [chloro(p-tolylsulfonyl)amino]sodium (550.8 mg, 2.42 mmol) and phenyltrimethylammonium tribromide (82.7 mg, 0.22 mmol). The mixture was stirred for 12 hours at rt under argon atmosphere. After LC/MS indicated the starting material of 4-allyl-1-chloro-2-(2-methoxyethoxy)benzene was consumed completely, the reaction mixture was filtered and the filtrate was concentrated in vacuo. The residue was purified by column chromatography to give 2-[[4-chloro-3-(2-methoxyethoxy)phenyl]methyl]-1-(p-tolylsulfonyl)aziridine (0.38 g).

Step 3: Preparation of N-[1-[[4-chloro-3-(2-methoxyethoxy)phenyl]methyl]-2-methylsulfanyl-ethyl]-4-methyl-benzenesulfonamide

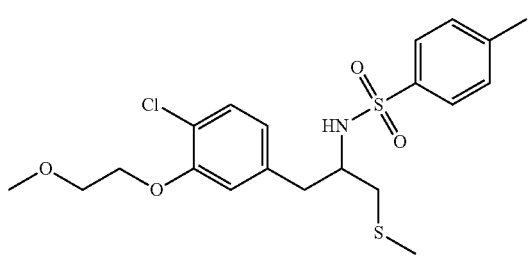

To a solution of 2-[[4-chloro-3-(2-methoxyethoxy)phenyl]methyl]-1-(p-tolylsulfonyl)aziridine (200 mg, 0.51 mmol) in the mixture of THF and water (2:1, 9 mL) was added S-methylisothiourea sulfate (114.1 mg, 0.61 mmol). Then a solution of sodium hydroxide (51.2 mg, 1.28 mmol) in water (2 mL) was slowly added to the above mixture. The mixture was stirred for 30 minutes at rt. After LC/MS indicated the starting material of 2-[[4-chloro-3-(2-methoxyethoxy)phenyl]methyl]-1-(p-tolylsulfonyl)aziridine was consumed completely, the reaction was quenched with 6 M hydrochloric acid. And then the mixture was extracted with EtOAc. The organic layer was dried over anhydrous Na$_2$SO$_4$ and concentrated in vacuo to give N-[1-[[4-chloro-3-(2-methoxyethoxy)phenyl]methyl]-2-methylsulfanyl-ethyl]-4-methyl-benzenesulfonamide (180 mg).

Step 4: Preparation of 1-[4-chloro-3-(2-methoxy-ethoxy)phenyl]-3-methylsulfanyl-propan-2-amine

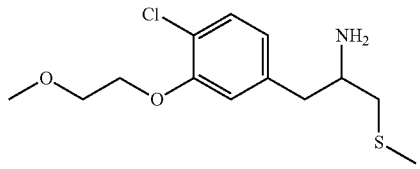

To a solution of N-[1-[[4-chloro-3-(2-methoxyethoxy)phenyl]methyl]-2-methylsulfanyl-ethyl]-4-methyl-benzenesulfonamide (180 mg, 0.41 mmol) in methanol (20 mL) was added magnesium ribbon (196.8 mg, 8.2 mmol). The mixture was stirred at 80° C. for 48 hours. After LC/MS indicated the starting material of N-[1-[[4-chloro-3-(2-methoxyethoxy)phenyl]methyl]-2-methylsulfanyl-ethyl]-4-methyl-benzenesulfonamide was consumed completely, the reaction was quenched with saturated aqueous ammonium chloride (50 mL), and the mixture was extracted with EtOAc. The organic layer was dried over anhydrous $Na_2SO_4$ and concentrated to give crude 1-[4-chloro-3-(2-methoxyethoxy)phenyl]-3-methylsulfanyl-propan-2-amine.

Step 5: Preparation of N-[1-[[4-chloro-3-(2-methoxyethoxy)phenyl]methyl]-2-methylsulfanyl-ethyl]formamide

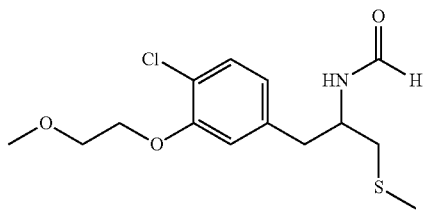 [SMILES: COCCOc1cc(CC(CSC)NC=O)ccc1Cl]

To a solution of crude 1-[4-chloro-3-(2-methoxyethoxy)phenyl]-3-methylsulfanyl-propan-2-amine (300 mg) in dioxane (10 mL) was added formic acid (0.2 mL). The mixture was stirred for 6 hours at 80° C. After LC/MS indicated the starting material of 1-[4-chloro-3-(2-methoxyethoxy)phenyl]-3-methylsulfanyl-propan-2-amine was consumed completely, the reaction mixture was concentrated in vacuo. The residue was purified by column chromatography to give N-[1-[[4-chloro-3-(2-methoxyethoxy)phenyl]methyl]-2-methylsulfanyl-ethyl]formamide (300 mg).

Step 6: Preparation of 7-chloro-6-(2-methoxyethoxy)-3-(methylsulfanylmethyl)-3,4-dihydroisoquinoline

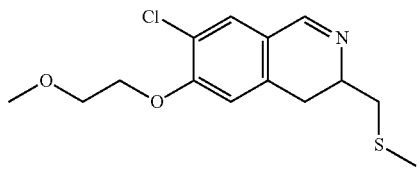

To a solution of N-[1-[[4-chloro-3-(2-methoxyethoxy)phenyl]methyl]-2-methylsulfanyl-ethyl]formamide (300 mg, 0.94 mmol) in acetonitrile (10 mL) was added phosphorus oxychloride (0.2 mL, 1.13 mmol). The mixture was stirred for 2 hours at 50° C. and concentrated in vacuo. The residue was partitioned between DCM and saturated aqueous sodium hydrogen carbonate solution. The organic layer was dried over anhydrous $Na_2SO_4$ and concentrated under reduced pressure to give 7-chloro-6-(2-methoxyethoxy)-3-(methylsulfanylmethyl)-3,4-dihydroisoquinoline (250 mg).

Step 7: Preparation of ethyl 10-chloro-9-(2-methoxyethoxy)-6-(methylsulfanylmethyl)-2-oxo-1,6,7,11b-tetrahydrobenzo[a]quinolizine-3-carboxylate

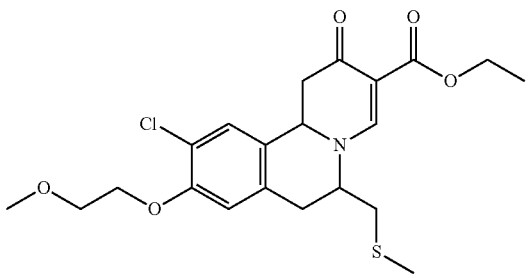 [SMILES: CCOC(=O)C1=CN2C(CSC)Cc3cc(OCCOC)c(Cl)cc3C2CC1=O]

To a solution of 7-chloro-6-(2-methoxyethoxy)-3-(methylsulfanylmethyl)-3,4-dihydroisoquinoline (250 mg, 0.83 mmol) in ethanol (10 mL) was added ethyl 2-(ethoxymethylene)-3-oxo-butanoate (463.6 mL, 2.49 mmol). The mixture was stirred for 16 hours at 100° C. After LC/MS indicated the starting material of 7-chloro-6-(2-methoxyethoxy)-3-(methylsulfanylmethyl)-3,4-dihydroisoquinoline was consumed completely, the reaction mixture was concentrated in vacuo to give crude ethyl 10-chloro-9-(2-methoxyethoxy)-6-(methylsulfanylmethyl)-2-oxo-1, 6, 7, 11b-tetrahydrobenzo[a]quinolizine-3-carboxylate which was used for the next step without purification.

Step 8: Preparation of ethyl 10-chloro-9-(2-methoxyethoxy)-6-(methylsulfanylmethyl)-2-oxo-6,7-dihydrobenzo[a]quinolizine-3-carboxylate

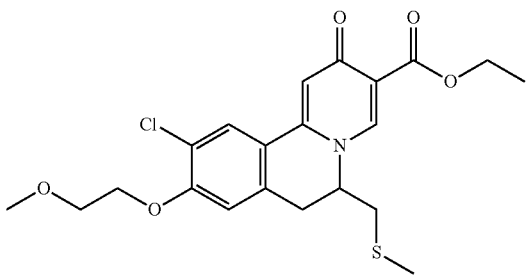 [SMILES: CCOC(=O)c1cn2c(cc1=O)-c1cc(Cl)c(OCCOC)cc1CC2CSC]

To a solution of crude ethyl 10-chloro-9-(2-methoxyethoxy)-6-(methylsulfanylmethyl)-2-oxo-1, 6, 7, 11b-tetrahydrobenzo[a]quinolizine-3-carboxylate in dimethoxyethane (10 mL) was added p-chloranil (142.9 mg, 0.58 mmol). The reaction mixture was stirred for 2 hours at 70° C. After LC/MS indicated the starting material of 10-chloro-9-(2-methoxyethoxy)-6-(methylsulfanylmethyl)-2-oxo-1,6,7,11b-tetrahydrobenzo[a]quinolizine-3-carboxylate was consumed completely, the reaction mixture was concentrated in vacuo to give crude ethyl 10-chloro-9-(2-methoxyethoxy)-6-(methylsulfanylmethyl)-2-oxo-6,7-dihydrobenzo[a]quinolizine-3-carboxylate which was used for the next step without purification.

Step 9: Preparation of 10-chloro-9-(2-methoxyethoxy)-6-(methylsulfanylmethyl)-2-oxo-6,7-dihydrobenzo[a]quinolizine-3-carboxylic acid

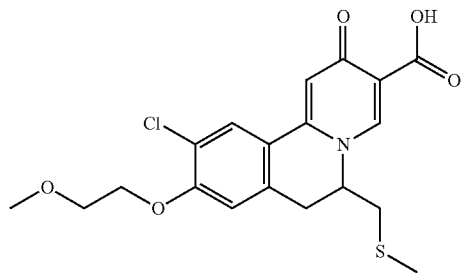 [SMILES: COCCOc1cc2c(cc1Cl)-c1cc(=O)c(C(=O)O)cn1C(CSC)C2]

To a solution of crude ethyl 10-chloro-9-(2-methoxyethoxy)-6-(methylsulfanylmethyl)-2-oxo-6,7-dihydrobenzo[a]quinolizine-3-carboxylate in a mixture of methanol and water (3:1, 12 mL) was added LiOH.H$_2$O (104.6 mg). The mixture was stirred for 2 hours at rt. After LC/MS indicated the starting material of 10-chloro-9-(2-methoxyethoxy)-6-(methylsulfanylmethyl)-2-oxo-6,7-dihydrobenzo[a]quinolizine-3-carboxylate was consumed completely, the reaction mixture was acidified with 6 M hydrochloric acid and concentrated in vacuo. The residue was purified by column chromatography to give 10-chloro-9-(2-methoxyethoxy)-6-(methylsulfanylmethyl)-2-oxo-6,7-dihydrobenzo[a]quinolizine-3-carboxylic acid (35 mg). $^1$H NMR (400 MHz, CDCl$_3$): δ 8.59 (s, 1H), 7.79 (s, 1H), 7.07 (s, 1H), 6.90 (s, 1H), 4.52-4.40 (m, 1H), 4.33-4.26 (m, 2H), 3.90-3.75 (m, 2H), 3.65-3.40 (m, 4H), 3.32-3.21 (m, 1H), 2.70-2.55 (m, 2H), 2.09 (s, 3H). MS obsd. (ESI$^+$) [(M+H)$^+$]: 410.

Example 34

10-Chloro-9-(2-methoxyethoxy)-6-(methylsulfonylmethyl)-2-oxo-6,7-dihydrobenzo[a]quinolizine-3-carboxylic acid

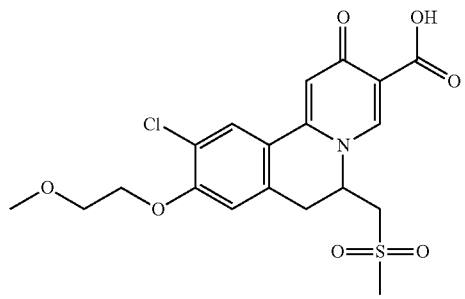 [SMILES: COCCOc1cc2c(cc1Cl)-c1cc(=O)c(C(=O)O)cn1C(CS(C)(=O)=O)C2]

To a solution of 10-chloro-9-(2-methoxyethoxy)-6-(methylsulfanylmethyl)-2-oxo-6,7-dihydrobenzo[a]quinolizine-3-carboxylic acid (30 mg, 0.07 mmol) in DCM was added 3-chloroperbenzoic acid (33 mg, 0.14 mmol) at 0° C. The mixture was stirred for 2 hours, and then concentrated in vacuo. The residue was purified by column chromatography to give 10-chloro-9-(2-methoxyethoxy)-6-(methylsulfonylmethyl)-2-oxo-6,7-dihydrobenzo[a]quinolizine-3-carboxylic acid (10 mg). $^1$H NMR (400 MHz, DMSO-d6): δ 8.75 (s, 1H), 8.25 (s, 1H), 7.43 (s, 1H), 7.25 (s, 1H), 5.51-5.41 (m, 1H), 4.38-4.29 (m, 2H), 3.77-3.70 (m, 2H), 3.59-3.47 (m, 2H), 3.45-3.38 (m, 1H), 3.35 (s, 3H), 3.23-3.14 (m, 1H), 3.04 (s, 3H). MS obsd. (ESI$^+$) [(M+H)$^+$]: 442.

Example 35

9,10-Diethoxy-6-(hydroxymethyl)-2-oxo-6,7-dihydrobenzo[a]quinolizine-3-carboxylic acid

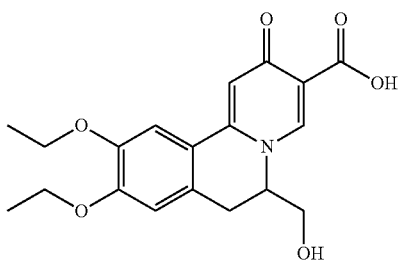 [SMILES: CCOc1cc2c(cc1OCC)-c1cc(=O)c(C(=O)O)cn1C(CO)C2]

Step 1: Preparation of 2-(tert-butoxycarbonylamino)-3-(3,4-dihydroxyphenyl)propanoic acid

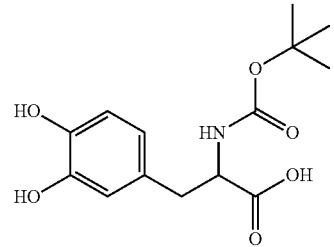 [SMILES: CC(C)(C)OC(=O)NC(Cc1ccc(O)c(O)c1)C(=O)O]

To a mixture of 2-amino-3-(3,4-dihydroxyphenyl)propanoic acid (50 g, 254 mmol), triethylamine (38.5 g, 380 mmol) in methanol (5 L) was added (Boc)$_2$O (58.1 g, 266 mmol). The mixture was stirred at rt for 16 hours and then concentrated to afford the crude 2-(tert-butoxycarbonylamino)-3-(3,4-dihydroxyphenyl)propanoic acid (100 g) as a black oil which was used in the next step without further purification.

Step 2: Preparation of ethyl 2-(tert-butoxycarbonylamino)-3-(3,4-diethoxyphenyl)propanoate

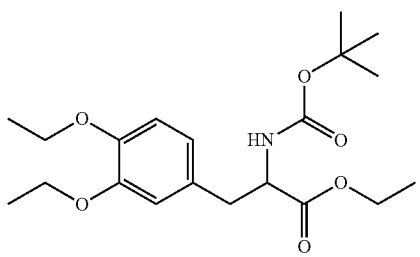 [SMILES: CCOC(=O)C(Cc1ccc(OCC)c(OCC)c1)NC(=O)OC(C)(C)C]

A mixture of 2-(tert-butoxycarbonylamino)-3-(3,4-dihydroxyphenyl)propanoic acid (100 g, 336 mmol), iodoethane (210 g, 1.35 mol) and Cs$_2$CO$_3$ (438 g, 1.35 mol) in DMF (400 mL) was stirred at rt for 16 hours. The mixture was partitioned between EtOAc (3 L) and water (3 L). The separated aqueous layer was extracted with EtOAc (1.5 L) 2 times. The combined organic layers were washed with brine, dried over anhydrous Na$_2$SO$_4$ and concentrated. The residue was purified by column chromatography to give ethyl 2-(tert-butoxycarbonylamino)-3-(3,4-diethoxyphenyl)propanoate (37 g) as a white solid.

Step 3: Preparation of tert-butyl N-[1-[(3,4-diethoxyphenyl)methyl]-2-hydroxy-ethyl]carbamate

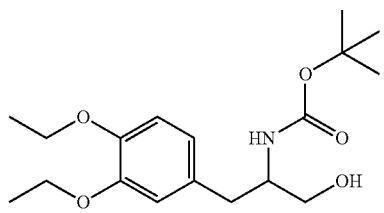 [SMILES: CCOc1ccc(CC(CO)NC(=O)OC(C)(C)C)cc1OCC]

To a mixture of ethyl 2-(tert-butoxycarbonylamino)-3-(3,4-diethoxyphenyl)propanoate (35 g, 92 mmol) in THF (400 mL) was added LiBH$_4$ (4.6 g, 211 mmol) in portions at 0-5° C. The resulting mixture was stirred at rt for 16 hours and then quenched with NH$_4$Cl aqueous solution. The resulting mixture was then partitioned between EtOAc (500 mL) and water (500 mL). The separated organic layer was concentrated to give tert-butyl N-[1-[(3,4-diethoxyphenyl)methyl]-2-hydroxy-ethyl]carbamate (30 g) as a colorless oil which was used in the next step without further purification.

Step 4: Preparation of [2-(tert-butoxycarbonylamino)-3-(3,4-diethoxyphenyl)propyl]acetate

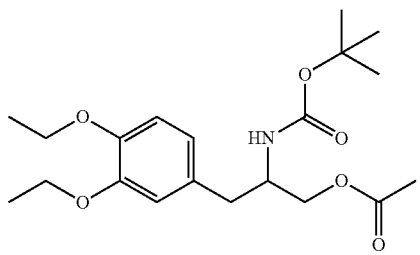 [SMILES: CCOc1ccc(CC(COC(C)=O)NC(=O)OC(C)(C)C)cc1OCC]

To a mixture of tert-butyl N-[1-[(3,4-diethoxyphenyl)methyl]-2-hydroxy-ethyl]carbamate (30 g, 88 mmol), N,N-diisopropylethylamine (13.7 g, 106 mmol) and DMAP (1.1 g, 8.8 mmol) in DCM (300 mL) was added acetic anhydride (9 g, 88 mmol) at 0-5° C. The mixture was stirred at rt for 16 hours, and then partitioned between DCM (1 L) and H$_2$O (1 L). The separated organic layer was washed with 0.5 M hydrochloride acid and NaHCO$_3$ aqueous solution sequentially, and then dried over anhydrous Na$_2$SO$_4$ and concentrated to give [2-(tert-butoxycarbonylamino)-3-(3,4-diethoxyphenyl)propyl]acetate (29 g) as a light yellow oil which was used in the next step without further purification.

Step 5: Preparation of [2-amino-3-(3,4-diethoxyphenyl)propyl]acetate

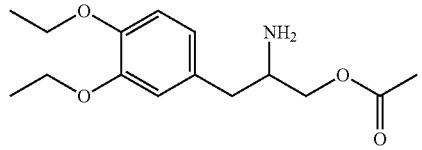 [SMILES: CCOc1ccc(CC(N)COC(C)=O)cc1OCC]

A mixture of [2-(tert-butoxycarbonylamino)-3-(3,4-diethoxyphenyl)propyl]acetate (29 g, 76 mmol) and formic acid (70 g, 1.52 mol) was stirred at rt for 16 hours, and then concentrated under reduced pressure to give [2-amino-3-(3,4-diethoxyphenyl)propyl]acetate (about 23 g) as a brown oil which was used in the next step without further purification.

Step 6: Preparation of [3-(3,4-diethoxyphenyl)-2-formamido-propyl]acetate

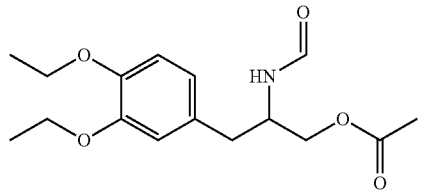 [SMILES: CCOc1ccc(CC(COC(C)=O)NC=O)cc1OCC]

A mixture of [2-amino-3-(3,4-diethoxyphenyl)propyl]acetate (23 g, 81.8 mmol) and formic acid (38 g, 818 mmol) in dioxane (200 mL) was stirred at 90° C. for 16 hours, and then concentrated. The residue was purified by column chromatography to give [3-(3,4-diethoxyphenyl)-2-formamido-propyl]acetate (17 g) as a yellow solid.

Step 7: Preparation of (6,7-diethoxy-3,4-dihydroisoquinolin-3-yl)methyl acetate

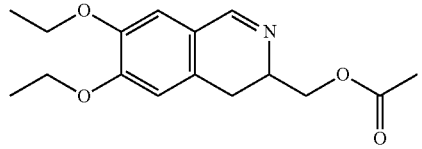 [SMILES: CCOc1cc2c(cc1OCC)CC(COC(C)=O)N=C2]

To a mixture of [3-(3,4-diethoxyphenyl)-2-formamido-propyl]acetate (15 g, 48.5 mmol) in DCM (300 mL) was added POCl$_3$ (10.03 g, 67.9 mmol) dropwise. The mixture was stirred at 40° C. for 4 hours, and then poured into water. After being adjusted to pH around 7 with NaHCO$_3$ aqueous solution, the mixture was extracted with DCM (500 mL) 2 times. The combined organic layers were concentrated, and the residue was purified by column chromatography and prep-HPLC sequentially to give (6,7-diethoxy-3,4-dihydroisoquinolin-3-yl)methyl acetate (4.05 g) as a yellow oil.

Step 8: Preparation of ethyl 6-(acetoxymethyl)-9,10-diethoxy-2-oxo-1,6,7,11b-tetrahydrobenzo[a]quinolizine-3-carboxylate

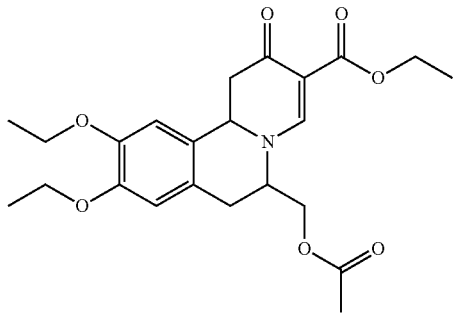

To a solution of (6,7-diethoxy-3,4-dihydroisoquinolin-3-yl)methyl acetate (291 mg, 1 mmol) and ethyl 2-(dimethylaminomethylene)-3-oxo-butanoate (278 mg, 1.5 mmol) in DMSO (1 mL) was added 4 M HCl in dioxane (50 µl, 0.2 mmol). The resultant mixture was heated to 130° C. for 5 hours under microwave. The mixture was cooled to rt, and then partitioned between EtOAc (10 mL) and H$_2$O (20 mL). The separated aqueous layer was extracted with EtOAc (20 mL) 3 times. The combined organic layers were washed with brine, dried over anhydrous Na$_2$SO$_4$ and concentrated to give crude ethyl 6-(acetoxymethyl)-9,10-diethoxy-2-oxo-1,6,7,11b-tetrahydrobenzo[a]quinolizine-3-carboxylate (421 mg) as a brown oil which was directly used for the next step without purification.

Step 9: Preparation of ethyl 6-(acetoxymethyl)-9,10-diethoxy-2-oxo-6,7-dihydrobenzo[a]quinolizine-3-carboxylate

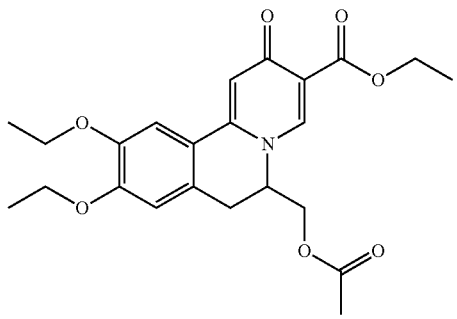 [SMILES: CCOC(=O)C1=CN2C(COC(C)=O)Cc3cc(OCC)c(OCC)cc3C2CC1=O]

A mixture of crude ethyl 6-(acetoxymethyl)-9,10-diethoxy-2-oxo-1,6,7,11b-tetrahydrobenzo[a]quinolizine-3-carboxylate (421 mg, 1 mmol) and p-chloranil (197 mg, 0.8 mmol) in DME (2 mL) was heated to 110° C. for 15 min under microwave. After being cooled to room temperature, the mixture was partitioned between EtOAc (10 mL) and H$_2$O (15 mL). The separated aqueous layer was extracted with EtOAc (20 mL) 3 times. The combined organic layers were washed with brine, dried over anhydrous Na$_2$SO$_4$ and concentrated to give crude ethyl 6-(acetoxymethyl)-9,10-diethoxy-2-oxo-6,7-dihydrobenzo[a]quinolizine-3-carboxylate (507 mg) as a dark brown oil which was used for the next step without purification.

Step 10: Preparation of 9,10-diethoxy-6-(hydroxymethyl)-2-oxo-6,7-dihydrobenzo[a]quinolizine-3-carboxylic acid

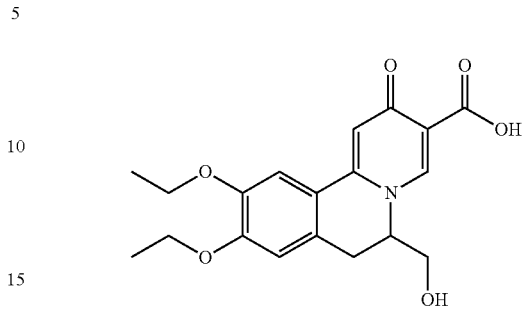

To a solution of crude ethyl 6-(acetoxymethyl)-9,10-diethoxy-2-oxo-6,7-dihydrobenzo[a]quinolizine-3-carboxylate (507 mg, 1 mmol) in methanol (4 mL) and H$_2$O (1 mL) was added LiOH.H$_2$O (168 mg, 4 mmol). The resulting reaction mixture was stirred at rt for 1 h, and then diluted with water. The mixture was acidified with 2 M hydrochloric acid to pH=2-3, and extracted with DCM 3 times. The combined organic layers were washed with brine, dried over anhydrous Na$_2$SO$_4$ and concentrated. The residue was purified by flash column to afford 9,10-diethoxy-6-(hydroxymethyl)-2-oxo-6,7-dihydrobenzo[a]quinolizine-3-carboxylic acid (107 mg) as a yellow solid. $^1$H NMR (400 MHz, DMSO-d6): δ 8.59 (s, 1H), 7.52 (s, 1H), 7.45 (s, 1H), 6.96 (s, 1H), 5.17 (br. s, 1H), 4.69 (td, 1H), 4.26-4.16 (m, 1H), 4.15-4.06 (m, 3H), 3.49 (dd, 1H), 3.39-3.24 (m, 2H), 2.98 (d, 1H), 1.36 (m, 6H). MS obsd. (ESI$^+$) [(M+H)$^+$]: 360.

Example 36

6-(Acetoxymethyl)-9,10-diethoxy-2-oxo-6,7-dihydrobenzo[a]quinolizine-3-carboxylic acid

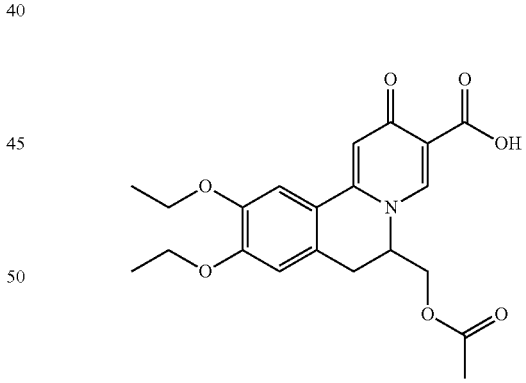

To a solution of 9,10-diethoxy-6-(hydroxymethyl)-2-oxo-6,7-dihydrobenzo[a]quinolizine-3-carboxylic acid (50 mg, 0.14 mmol), pyridine (66 mg, 0.84 mmol) and 4-dimethylaminopyridine (3.6 mg, 0.028 mmol) in DCM (2 mL) was added acetyl chloride (33 mg, 0.42 mmol). The resulting mixture was stirred at rt overnight and then purified by flash column to give 6-(acetoxymethyl)-9,10-diethoxy-2-oxo-6,7-dihydrobenzo[a]quinolizine-3-carboxylic acid (11 mg) as a yellow solid. $^1$H NMR (400 MHz, DMSO-d6): δ 8.71 (s, 1H), 7.53 (s, 1H), 7.45 (s, 1H), 6.98 (s, 1H), 5.12-4.95 (m, 1H), 4.27-4.02 (m, 6H), 3.43 (dd, 2H), 3.06 (d, 1H), 1.86 (s, 3H), 1.39-1.32 (m, 6H). MS obsd. (ESI$^+$) [(M+H)$^+$]: 402.

Example 37

6-(Aminomethyl)-9,10-diethoxy-2-oxo-6,7-dihydrobenzo[a]quinolizine-3-carboxylic acid

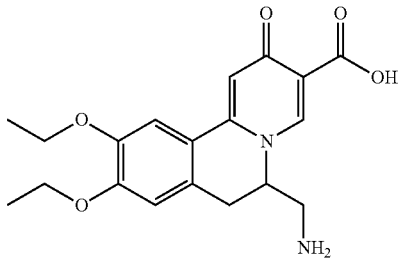 [SMILES: CCOc1cc2c(cc1OCC)-c1cc(=O)c(C(=O)O)cn1C(CN)C2]

Step 1: Preparation of tert-butyl N-[1-[(3,4-diethoxyphenyl)methyl]-2-(1,3-dioxoisoindolin-2-yl)ethyl]carbamate

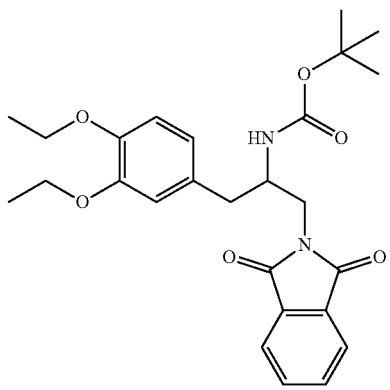 [SMILES: CCOc1ccc(CC(CN2C(=O)c3ccccc3C2=O)NC(=O)OC(C)(C)C)cc1OCC]

To a solution of tert-butyl N-[1-[(3,4-diethoxyphenyl)methyl]-2-hydroxy-ethyl]carbamate (16.76 g, 49.4 mmol, from Step 3 of Example 35), phthalimide (7.98 g, 54.3 mmol) and triphenylphosphine (15.54 g, 59.3 mmol) in THF (150 mL) was added diethyl azodicarboxylate (12.89 g, 74.1 mmol) dropwise at 0° C. The resulting mixture was allowed to warm to rt with the ice-bath and stirred at rt overnight. The mixture was diluted with water (200 mL), extracted with EtOAc (100 mL) 3 times. The combined organic layers were washed with brine, dried over anhydrous $Na_2SO_4$ and concentrated. The residue was treated with ethanol/$H_2O$ to give crude tert-butyl N-[1-[(3,4-diethoxyphenyl)methyl]-2-(1,3-dioxoisoindolin-2-yl)ethyl]carbamate (31.54 g) as a yellow solid which was directly used for the next step without further purification.

Step 2: Preparation of 2-[2-amino-3-(3,4-diethoxyphenyl)propyl]isoindoline-1,3-dione hydrochloride

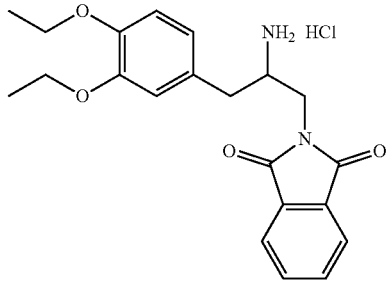 [SMILES: CCOc1ccc(CC(N)CN2C(=O)c3ccccc3C2=O)cc1OCC ; Cl]

To a solution of crude tert-butyl N-[1-[(3,4-diethoxyphenyl)methyl]-2-(1,3-dioxoisoindolin-2-yl)ethyl]carbamate (31.54 g, 49.4 mmol) in 1,4-dioxane (150 mL) was added 4 M HCl in dioxane (150 mL). The mixture was stirred at rt overnight. After removing solvent under reduced pressure, the residue was slurried in EtOAc (300 mL) for 1 h, and the resulting suspension was filtered. The filter cake was dried to give 2-[2-amino-3-(3,4-diethoxyphenyl)propyl]isoindoline-1,3-dione hydrochloride (13.1 g) as a yellow solid which was used for the next step without further purification.

Step 3: Preparation of N-[1-[(3,4-diethoxyphenyl)methyl]-2-(1,3-dioxoisoindolin-2-yl)ethyl]formamide

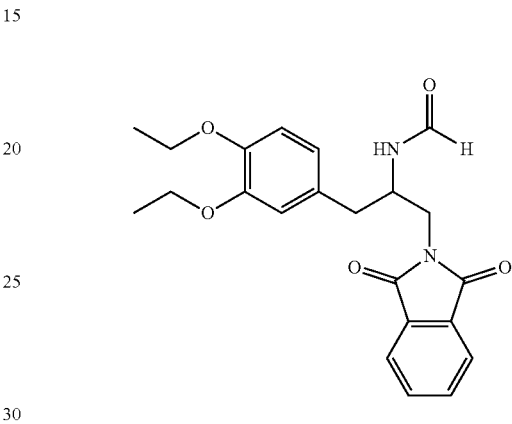

A mixture of 2-[2-amino-3-(3,4-diethoxyphenyl)propyl]isoindoline-1,3-dione hydrochloride (13.1 g, 32.4 mmol), ethyl formate (200 mL), triethylamine (9.82 g, 97.2 mmol) and formic acid (10 mL) in 1,4-dioxane (100 mL) was heated at 100° C. for 48 h. After being cooled to rt, the mixture was diluted with water (200 mL) and extracted with EtOAc (100 mL) 3 times. The combined organic layers were washed with brine, dried over anhydrous $Na_2SO_4$, and concentrated to give N-[1-[(3,4-diethoxyphenyl)methyl]-2-(1,3-dioxoisoindolin-2-yl)ethyl]formamide (14.5 g) as a brown oil.

Step 4: Preparation of 2-[(6,7-diethoxy-3,4-dihydroisoquinolin-3-yl)methyl]isoindoline-1,3-dione

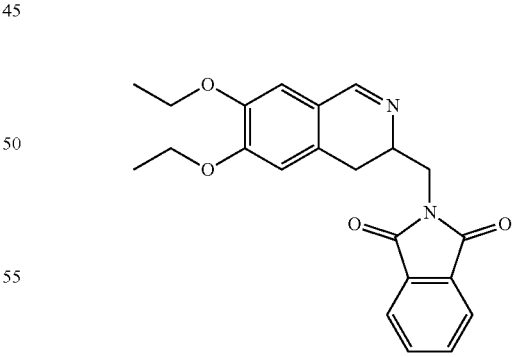

To a solution of crude N-[1-[(3,4-diethoxyphenyl)methyl]-2-(1,3-dioxoisoindolin-2-yl)ethyl]formamide (14.5 g, 32.4 mmol) in acetonitrile (150 mL) was added $POCl_3$ (5.95 g, 38.9 mmol). The resulting mixture was heated at 60° C. for 3 h. After removing the solvent and excess $POCl_3$ by concentration, the residue was dissolved in acetonitrile (50 mL), and the solvent was cooled to 0° C. and basified with ammonium hydroxide. The resulting mixture was diluted with water and extracted with DCM (150 mL) 3 times. The combined organic layers were washed with brine, dried over anhydrous Na$_2$SO$_4$ and concentrated to give 2-[(6,7-diethoxy-3,4-dihydroisoquinolin-3-yl)methyl]isoindoline-1,3-dione (10.1 g) as a yellow solid which was used for the next step without purification.

Step 5: Preparation of ethyl 6-[(1,3-dioxoisoindolin-2-yl)methyl]-9,10-diethoxy-2-oxo-1,6,7,11b-tetrahydrobenzo[a]quinolizine-3-carboxylate

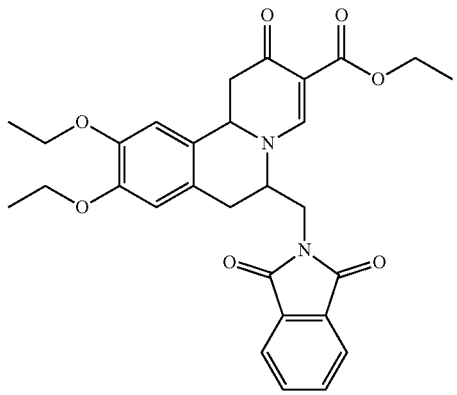 [SMILES: CCOC(=O)C1=CN2C(CN3C(=O)c4ccccc4C3=O)Cc3cc(OCC)c(OCC)cc3C2CC1=O]

A mixture of 2-[(6,7-diethoxy-3,4-dihydroisoquinolin-3-yl)methyl]isoindoline-1,3-dione (10.1 g, 26.7 mmol) and ethyl 2-(ethoxymethylene)-3-oxo-butanoate (14.9 g, 80.1 mmol) in ethanol (150 mL) was heated at 100° C. for 48 h. The mixture was concentrated under reduced pressure to give crude ethyl 6-[(1,3-dioxoisoindolin-2-yl)methyl]-9,10-diethoxy-2-oxo-1,6,7,11b-tetrahydrobenzo[a]quinolizine-3-carboxylate (22.6 g) as a dark brown oil which was used in the next step without purification.

Step 6: Preparation of ethyl 6-[(1,3-dioxoisoindolin-2-yl)methyl]-9,10-diethoxy-2-oxo-6,7-dihydrobenzo[a]quinolizine-3-carboxylate

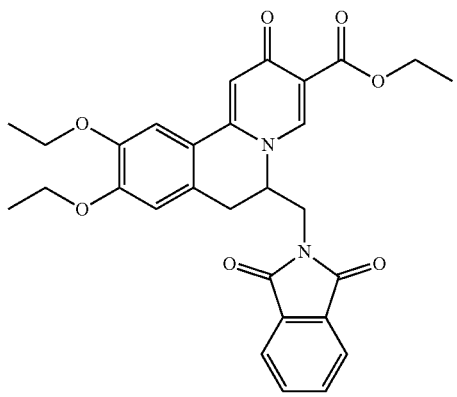 [SMILES: CCOC(=O)c1cn2c(cc1=O)-c1cc(OCC)c(OCC)cc1CC2CN1C(=O)c2ccccc2C1=O]

A mixture of crude ethyl 6-[(1,3-dioxoisoindolin-2-yl)methyl]-9,10-diethoxy-2-oxo-6,7-dihydrobenzo[a]quinolizine-3-carboxylate (22.6 g, 26.7 mmol) and p-chloranil (6.57 g, 26.7 mmol) in DME (100 mL) was heated at 70° C. for 2 h under argon. After being cooled to room temperature, the mixture was partitioned between DCM and water. The separated aqueous layer was extracted with DCM for three times. The combined organic layers were washed with saturated NaHCO$_3$ aqueous solution and brine sequentially. Then the organic layer was dried over anhydrous Na$_2$SO$_4$ and concentrated to give crude ethyl 6-[(1,3-dioxoisoindolin-2-yl)methyl]-9,10-diethoxy-2-oxo-6,7-dihydrobenzo[a]quinolizine-3-carboxylate (11.2 g) as a dark oil which was used in the next step without further purification.

Step 7: Preparation of ethyl 6-(aminomethyl)-9,10-diethoxy-2-oxo-6,7-dihydrobenzo[a]quinolizine-3-carboxylate

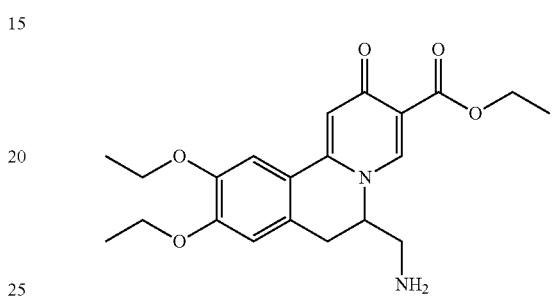

A mixture of crude ethyl 6-[(1,3-dioxoisoindolin-2-yl)methyl]-9,10-diethoxy-2-oxo-6,7-dihydrobenzo[a]quinolizine-3-carboxylate (9.1 g, 17.6 mmol) and 85% hydrazine monohydrate (3.1 g, 52.8 mmol) in ethanol (100 mL) was heated at 50° C. for 5 h. After being cooled to rt, the mixture was diluted with water and then filtered. The filter cake was dried to give ethyl 6-(aminomethyl)-9,10-diethoxy-2-oxo-6,7-dihydrobenzo[a]quinolizine-3-carboxylate (2.59 g) as a brown solid. The mother liquid was extracted with DCM for three times. The combined organic layers were washed with brine, dried over anhydrous Na$_2$SO$_4$ and concentrated to give crude ethyl 6-(aminomethyl)-9,10-diethoxy-2-oxo-6,7-dihydrobenzo[a]quinolizine-3-carboxylate (2.67 g) as brown solid.

Step 8: Preparation of 6-(aminomethyl)-9,10-diethoxy-2-oxo-6,7-dihydrobenzo[a]quinolizine-3-carboxylic acid

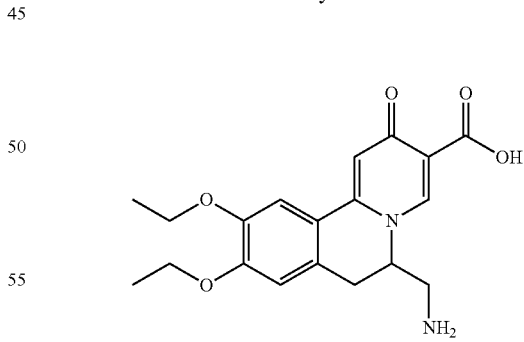

To a solution of ethyl 6-(aminomethyl)-9,10-diethoxy-2-oxo-6,7-dihydrobenzo[a]quinolizine-3-carboxylate (116 mg, 0.3 mmol) in methanol (4 mL) and water (1 mL) was added LiOH.H$_2$O (50 mg, 1.2 mmol). The resulting mixture was stirred at rt for 2 h. The mixture was diluted with water and acidified with 1 M hydrochloric acid to pH=6. Then the mixture was extracted with DCM (50 mL) 3 times, and the combined organic layers were washed with brine, dried over anhydrous Na$_2$SO$_4$ and concentrated. The residue was purified by prep-HPLC to afford 6-(aminomethyl)-9,10-diethoxy-2-oxo-6,7-dihydrobenzo[a]quinolizine-3-carboxylic acid (2.3 mg) as an off-white solid. $^1$H NMR (400 MHz, MeOD): δ 8.92-8.62 (br.s, 1H), 8.55 (s, 1H), 7.43 (s, 1H), 7.25 (s, 1H), 6.98 (s, 1H), 4.75-4.41 (m, 1H), 4.26-4.09 (m, 4H), 3.53-3.39 (m, 1H), 3.20-3.05 (m, 1H), 2.91-2.67 (m, 2H), 1.47 (m, 6H). MS obsd. (ESI$^+$) [(M+H)$^+$]: 359.

Example 38

9,10-Diethoxy-6-(methanesulfonamidomethyl)-2-oxo-6,7-dihydrobenzo[a]quinolizine-3-carboxylic acid

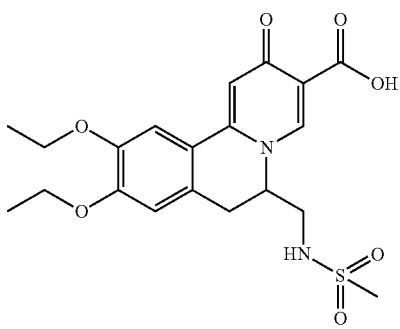 [SMILES: CCOc1cc2c(cc1OCC)-c1cc(=O)c(C(=O)O)cn1C(CNS(C)(=O)=O)C2]

Step 1: Preparation of ethyl 9,10-diethoxy-6-(methanesulfonamidomethyl)-2-oxo-6,7-dihydrobenzo[a]quinolizine-3-carboxylate

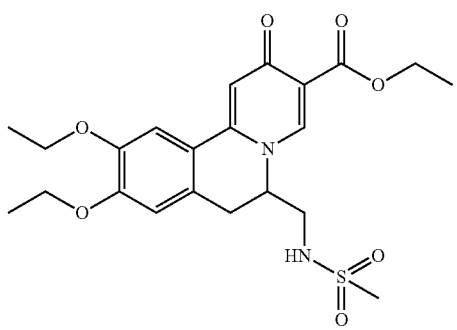 [SMILES: CCOC(=O)c1cn2c(cc1=O)-c1cc(OCC)c(OCC)cc1CC2CNS(C)(=O)=O]

To a solution of ethyl 6-(aminomethyl)-9,10-diethoxy-2-oxo-6,7-dihydrobenzo[a]quinolizine-3-carboxylate (116 mg, 0.3 mmol), triethylamine (91 mg, 0.9 mmol) in DCM (3 mL) was added methanesulfonyl chloride (46 mg, 0.4 mmol) at 0° C. The resulting mixture was allowed to warm to rt and stirred for 2 h. The resulting mixture was diluted with water and extracted with DCM three times. The combined organic layers were washed with brine, dried over anhydrous Na$_2$SO$_4$ and concentrated to give crude ethyl 9,10-diethoxy-6-(methanesulfonamidomethyl)-2-oxo-6,7-dihydrobenzo[a]quinolizine-3-carboxylate (184 mg) which was used for the next step without purification.

Step 2: Preparation of 9,10-diethoxy-6-(methanesulfonamidomethyl)-2-oxo-6,7-dihydrobenzo[a]quinolizine-3-carboxylic acid

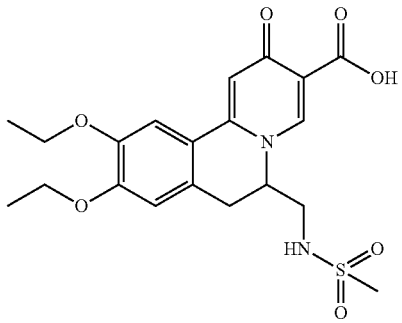 [SMILES: CCOc1cc2c(cc1OCC)-c1cc(=O)c(C(=O)O)cn1C(CNS(C)(=O)=O)C2]

To a solution of crude ethyl 9,10-diethoxy-6-(methanesulfonamidomethyl)-2-oxo-6,7-dihydrobenzo[a]quinolizine-3-carboxylate (184 mg, 0.3 mmol) in methanol (4 mL) and water (1 mL) was added LiOH.H$_2$O (50 mg, 1.2 mmol). The resulting mixture was stirred at rt for 16 h. The mixture was diluted with water and acidified with 1 M hydrochloric acid to pH=2-3. Then the mixture was extracted with DCM three times, and the combined organic layers were washed with brine, dried over anhydrous Na$_2$SO$_4$ and concentrated. The residue was purified by prep-HPLC to afford 9,10-diethoxy-6-(methanesulfonamidomethyl)-2-oxo-6,7-dihydrobenzo[a]quinolizine-3-carboxylic acid (8.8 mg) as a yellow solid. $^1$H NMR (400 MHz, DMSO-d6): δ 8.61 (s, 1H), 7.53 (s, 1H), 7.46 (s, 1H), 7.39 (t, 1H), 6.98 (s, 1H), 4.69 (td, 1H), 4.28-4.17 (m, 1H), 4.16-4.08 (m, 3H), 3.39 (dd, 1H), 3.12 (td, 1H), 3.03 (d, 1H), 3.00-2.91 (m, 1H), 2.82 (s, 3H), 1.36 (td, 6H). MS obsd. (ESI$^+$) [(M+H)$^+$]: 437.

Example 39

6-(Benzamidomethyl)-9,10-diethoxy-2-oxo-6,7-dihydrobenzo[a]quinolizine-3-carboxylic acid

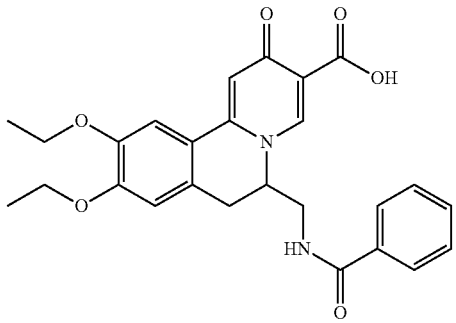 [SMILES: CCOc1cc2c(cc1OCC)-c1cc(=O)c(C(=O)O)cn1C(CNC(=O)c1ccccc1)C2]

Step 1: Preparation of ethyl 6-(benzamidomethyl)-9,10-diethoxy-2-oxo-6,7-dihydrobenzo[a]quinolizine-3-carboxylate

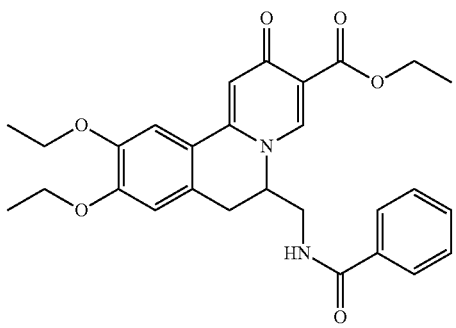 [SMILES: CCOC(=O)c1cn2c(cc1=O)-c1cc(OCC)c(OCC)cc1CC2CNC(=O)c1ccccc1]

To a solution of ethyl 6-(aminomethyl)-9,10-diethoxy-2-oxo-6,7-dihydrobenzo[a]quinolizine-3-carboxylate (116 mg, 0.3 mmol) and triethylamine (91 mg, 0.9 mmol) in DCM (3 mL) was added benzoyl chloride (56 mg, 0.4 mmol) at 0° C. The resulting mixture was allowed to warm to rt and stirred overnight. The mixture was diluted with water and then extracted with DCM three times. The combined organic layers were washed with brine, dried over anhydrous $Na_2SO_4$ and concentrated to give crude ethyl 6-(benzamidomethyl)-9,10-diethoxy-2-oxo-6,7-dihydrobenzo[a]quinolizine-3-carboxylate (175 mg) which was used for the next step without purification.

Step 2: Preparation of 6-(benzamidomethyl)-9,10-diethoxy-2-oxo-6,7-dihydrobenzo[a]quinolizine-3-carboxylic acid

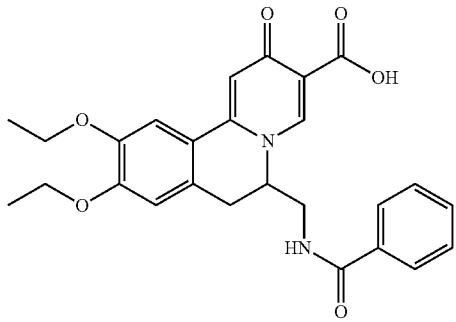 [SMILES: CCOc1cc2c(cc1OCC)-c1cc(=O)c(C(=O)O)cn1C(CNC(=O)c1ccccc1)C2]

To a solution of crude ethyl 6-(benzamidomethyl)-9,10-diethoxy-2-oxo-6,7-dihydrobenzo[a]quinolizine-3-carboxylate (175 mg, 0.3 mmol) in methanol (4 mL) and water (1 mL) was added $LiOH \cdot H_2O$ (50 mg, 1.2 mmol). The resulting mixture was stirred at rt for 2 h, and then diluted with water, and acidified with 1 M hydrochloric acid to pH=2-3. Then the mixture was extracted with DCM three times, and the combined organic layers were washed with brine, dried over anhydrous $Na_2SO_4$ and concentrated. The residue was purified by prep-HPLC to afford 6-(benzamidomethyl)-9,10-diethoxy-2-oxo-6,7-dihydrobenzo[a]quinolizine-3-carboxylic acid (5.8 mg) as a yellow solid. $^1H$ NMR (400 MHz, DMSO-d6) δ 8.60 (dd, 1H), 8.53 (s, 1H), 7.67-7.61 (m, 2H), 7.55 (s, 1H), 7.54-7.49 (m, 1H), 7.46 (s, 1H), 7.45-7.39 (m, 2H), 7.01 (s, 1H), 4.88-4.79 (m, 1H), 4.27-4.18 (m, 1H), 4.17-4.07 (m, 3H), 3.53-3.39 (m, 2H), 3.32-3.28 (m, 1H), 3.08 (d, 1H), 1.37 (td, 6H). MS obsd. ($ESI^+$) $[(M+H)^+]$: 463.

Example 40

9,10-Diethoxy-2-oxo-6-[(2-oxopyrrolidin-1-yl)methyl]-6,7-dihydrobenzo[a]quinolizine-3-carboxylic acid

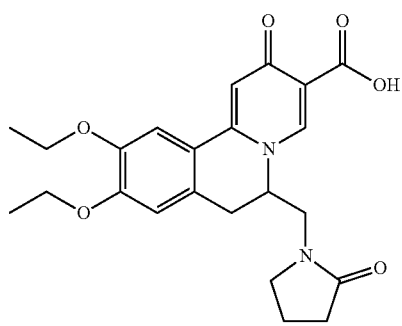 [SMILES: CCOc1cc2c(cc1OCC)-c1cc(=O)c(C(=O)O)cn1C(CN1CCCC1=O)C2]

Step 1: Preparation of ethyl 6-[(4-chlorobutanoylamino)methyl]-9,10-diethoxy-2-oxo-6,7-dihydrobenzo[a]quinolizine-3-carboxylate

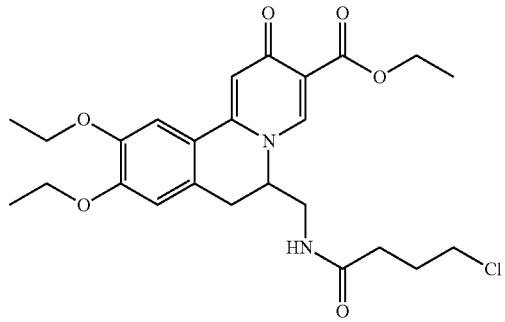 [SMILES: CCOC(=O)c1cn2c(cc1=O)-c1cc(OCC)c(OCC)cc1CC2CNC(=O)CCCCl]

To a solution of ethyl 6-(aminomethyl)-9,10-diethoxy-2-oxo-6,7-dihydrobenzo[a]quinolizine-3-carboxylate (116 mg, 0.3 mmol) and triethylamine (91 mg, 0.9 mmol) in DCM (3 mL) was added 4-chlorobutyryl chloride (56 mg, 0.4 mmol) at 0° C. The resulting mixture was allowed to warm to rt and stirred for 2 h. The mixture was diluted with water and then extracted with DCM three times. The combined organic layers were washed with brine, dried over anhydrous $Na_2SO_4$ and concentrated to give crude ethyl 6-[(4-chlorobutanoylamino)methyl]-9,10-diethoxy-2-oxo-6,7-dihydrobenzo[a]quinolizine-3-carboxylate (215 mg) as a brown oil which was used for the next step without purification.

Step 2: Preparation of 9,10-diethoxy-2-oxo-6-[(2-oxopyrrolidin-1-yl)methyl]-6,7-dihydrobenzo[a]quinolizine-3-carboxylic acid

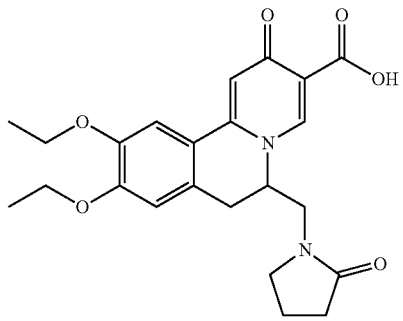 [SMILES: CCOc1cc2c(cc1OCC)-c1cc(=O)c(C(=O)O)cn1C(CN1CCCC1=O)C2]

To a solution of crude ethyl 6-[(4-chlorobutanoylamino)methyl]-9,10-diethoxy-2-oxo-6,7-dihydrobenzo[a]quinolizine-3-carboxylate (215 mg, 0.3 mmol) in THF (5 mL) was added potassium tert-butylate (101 mg, 0.9 mmol) at 0° C. The resulting mixture was allowed to warm to rt and stirred for 3 h. Water (1 mL) was added to the above reaction mixture, followed by addition of $LiOH \cdot H_2O$ (50 mg, 1.2 mmol). The resulting mixture was stirred at rt overnight, then diluted with water and acidified with 1 M hydrochloric acid to pH=2-3. Then the mixture was extracted with DCM three times. The combined organic layers were washed with brine, dried over anhydrous $Na_2SO_4$ and concentrated. The residue was purified by prep-HPLC to afford 9,10-diethoxy-2-oxo-6-[(2-oxopyrrolidin-1-yl)methyl]-6,7-dihydrobenzo

[a]quinolizine-3-carboxylic acid (5.6 mg) as a yellow solid. ¹H NMR (400 MHz, DMSO-d6): δ 8.52 (s, 1H), 7.53 (s, 1H), 7.44 (s, 1H), 6.98 (s, 1H), 4.98-4.86 (m, 1H), 4.27-4.19 (m, 1H), 4.17-4.08 (m, 3H), 3.68-3.57 (m, 1H), 3.51-3.39 (m, 2H), 3.20-3.07 (m, 2H), 2.98 (d, 1H), 2.17-2.05 (m, 1H), 2.01-1.91 (m, 1H), 1.91-1.81 (m, 2H), 1.36 (m, 6H). MS obsd. (ESI⁺) [(M+H)⁺]: 427.

Example 41

6-[[Acetyl(methyl)amino]methyl]-9,10-diethoxy-2-oxo-6,7-dihydrobenzo[a]quinolizine-3-carboxylic acid

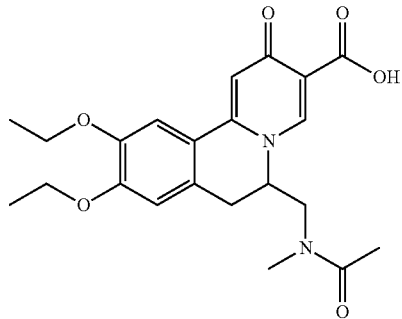 [SMILES: CCOc1cc2c(cc1OCC)-c1cc(=O)c(C(=O)O)cn1C(CN(C)C(C)=O)C2]

Step 1: Preparation of ethyl 6-(acetamidomethyl)-9,10-diethoxy-2-oxo-6,7-dihydrobenzo[a]quinolizine-3-carboxylate

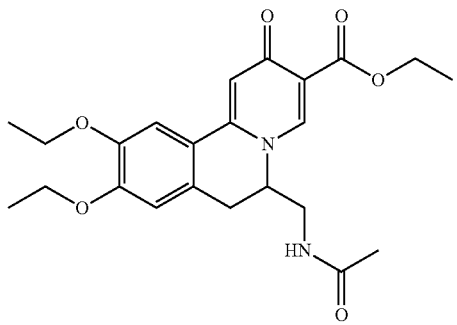 [SMILES: CCOC(=O)c1cn2c(cc1=O)-c1cc(OCC)c(OCC)cc1CC2CNC(C)=O]

To a solution of ethyl 6-(aminomethyl)-9,10-diethoxy-2-oxo-6,7-dihydrobenzo[a]quinolizine-3-carboxylate (116 mg, 0.3 mmol) and triethylamine (91 mg, 0.9 mmol) in DCM (3 mL) was added acetyl chloride (31 mg, 0.4 mmol) at 0° C. The resulting mixture was allowed to warm to rt and stirred at rt for 64 h. The mixture was diluted with H₂O, and then extracted with DCM three times. The combined organic layers were washed with brine, dried over anhydrous Na₂SO₄ and concentrated to give crude ethyl 6-(acetamidomethyl)-9,10-diethoxy-2-oxo-6,7-dihydrobenzo[a]quinolizine-3-carboxylate (148 mg) as a brown oil which was used for the next step without purification.

Step 2: Preparation of 6-[[acetyl(methyl)amino]methyl]-9,10-diethoxy-2-oxo-6,7-dihydrobenzo[a]quinolizine-3-carboxylic acid

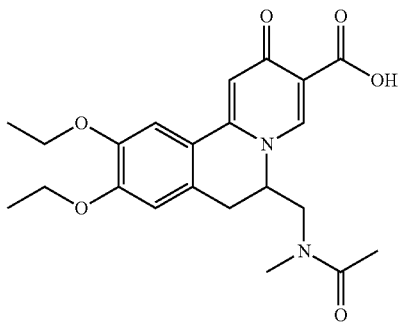 [SMILES: CCOc1cc2c(cc1OCC)-c1cc(=O)c(C(=O)O)cn1C(CN(C)C(C)=O)C2]

To a solution of crude ethyl 6-(acetamidomethyl)-9,10-diethoxy-2-oxo-6,7-dihydrobenzo[a]quinolizine-3-carboxylate (148 mg, 0.3 mmol) in DMF (3 mL) was added 60% NaH (24 mg, 0.6 mmol) at 0° C. under argon. The mixture was stirred at 0° C. for 30 minutes, and then to the mixture was added iodomethane (213 mg, 1.5 mmol). The mixture was allowed to warm to rt and stirred overnight. The mixture was concentrated, and then the residue was dissolved in methanol (4 mL) and H₂O (1 mL). To the resulting solution was added LiOH.H₂O (50 mg, 1.2 mmol). The resulting mixture was stirred at rt for 2 h, and then diluted with water and acidified with 1 M hydrochloric acid to pH=2-3. The mixture was extracted with DCM three times, and the combined organic layers were washed with brine, dried over anhydrous Na₂SO₄ and concentrated. The residue was purified by prep-HPLC to afford 6-[[acetyl(methyl)amino]methyl]-9,10-diethoxy-2-oxo-6,7-dihydrobenzo[a]quinolizine-3-carboxylic acid (4.8 mg) as a yellow solid. ¹H NMR (400 MHz, DMSO-d6): δ 8.43 (s, 1H), 7.52 (s, 1H), 7.42 (s, 1H), 6.98 (s, 1H), 4.90 (m, 1H), 4.14-4.09 (m, 4H), 3.65 (dd, 1H), 3.39 (m, 1H), 3.12 (dd, 1H), 3.08-2.93 (m, 1H), 2.89 (s, 3H), 1.81 (s, 3H), 1.37 (t, 6H). And about 0.4:1 rotamer: δ 8.60 (s, 1H), 7.57 (s, 1H), 7.49 (s, 1H), 7.05 (s, 1H), 5.04 (m, 1H), 4.24-4.15 (m, 4H), 3.65 (dd, 1H), 3.43-3.37 (m, 3H), 2.75 (s, 3H), 1.54 (s, 3H), 1.33 (t, 6H). MS obsd. (ESI⁺) [(M+H)⁺]: 415.

Example 42

9,10-Diethoxy-2-oxo-6-(pyrrolidin-1-ylmethyl)-6,7-dihydrobenzo[a]quinolizine-3-carboxylic acid

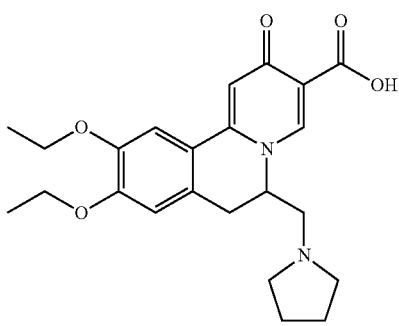 [SMILES: CCOc1cc2c(cc1OCC)-c1cc(=O)c(C(=O)O)cn1C(CN1CCCC1)C2]

Step 1: Preparation of ethyl 9,10-diethoxy-2-oxo-6-(pyrrolidin-1-ylmethyl)-6,7-dihydrobenzo[a]quinolizine-3-carboxylate

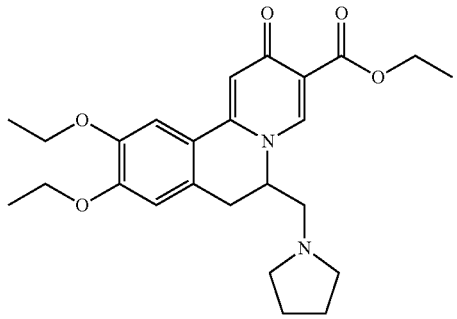 [SMILES: CCOC(=O)c1cn2c(cc1=O)-c1cc(OCC)c(OCC)cc1CC2CN1CCCC1]

To a solution of ethyl 6-(aminomethyl)-9,10-diethoxy-2-oxo-6,7-dihydrobenzo[a]quinolizine-3-carboxylate (232 mg, 0.6 mmol) and triethylamine (158 mg, 1.56 mmol) in acetonitrile (3 mL) was added 1,4-dibromobutane (168 mg, 0.78 mmol). The resulting mixture was stirred at 85° C. for 16 h, and then concentrated to give ethyl 9,10-diethoxy-2-oxo-6-(pyrrolidin-1-ylmethyl)-6,7-dihydrobenzo[a]quinolizine-3-carboxylate (534 mg) as a brown oil which was used for the next step without purification.

Step 2: Preparation of 9,10-diethoxy-2-oxo-6-(pyrrolidin-1-ylmethyl)-6,7-dihydrobenzo[a]quinolizine-3-carboxylic acid

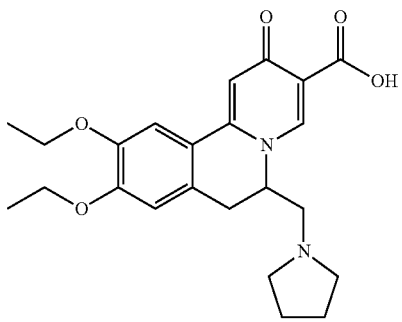 [SMILES: CCOc1cc2c(cc1OCC)-c1cc(=O)c(C(=O)O)cn1C(CN1CCCC1)C2]

To a solution of crude ethyl 9,10-diethoxy-2-oxo-6-(pyrrolidin-1-ylmethyl)-6,7-dihydrobenzo[a]quinolizine-3-carboxylate (534 mg, 0.6 mmol) in methanol (8 mL) and water (2 mL) was added LiOH.H$_2$O (101 mg, 2.4 mmol). The resulting mixture was stirred at rt for 3 h. The mixture was diluted with water, acidified with 1 M hydrochloric acid to pH=2-3, and then extracted with DCM three times. The combined organic layers were washed with brine, dried over anhydrous Na$_2$SO$_4$ and concentrated. The residue was purified by prep-HPLC to afford 9,10-diethoxy-2-oxo-6-(pyrrolidin-1-ylmethyl)-6,7-dihydrobenzo[a]quinolizine-3-carboxylic acid (8.2 mg) as a yellow solid. $^1$H NMR (400 MHz, DMSO-d6): δ 8.61 (s, 1H), 7.52 (s, 1H), 7.44 (s, 1H), 6.99 (s, 1H), 4.88-4.78 (m, 1H), 4.24-4.17 (m, 1H), 4.16-4.08 (m, 3H), 3.02 (d, 1H), 2.60-2.54 (m, 2H), 2.48-2.38 (m, 2H), 2.35-2.26 (m, 2H), 1.62 (m, 4H), 1.36 (m, 6H). MS obsd. (ESI$^+$) [(M+H)$^+$]: 413.

Example 43

6-[(Dimethylamino)methyl]-9,10-diethoxy-2-oxo-6,7-dihydrobenzo[a]quinolizine-3-carboxylic acid

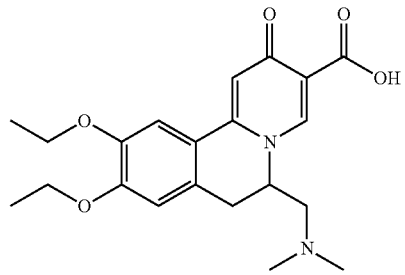 [SMILES: CCOc1cc2c(cc1OCC)-c1cc(=O)c(C(=O)O)cn1C(CN(C)C)C2]

A mixture of ethyl 6-(aminomethyl)-9,10-diethoxy-2-oxo-6,7-dihydrobenzo[a]quinolizine-3-carboxylate (193 mg, 0.5 mmol) and 37 wt % formaldehyde (1.22 g, 15 mmol) in formic acid (690 mg, 15 mmol) was heated to 95° C. for 16 h. The mixture was concentrated and the residue was purified by prep-HPLC to afford 6-[(dimethylamino)methyl]-9,10-diethoxy-2-oxo-6,7-dihydrobenzo[a]quinolizine-3-carboxylic acid (12.3 mg) as a yellow solid. $^1$H NMR (400 MHz, DMSO-d6): δ 8.63 (s, 1H), 7.52 (s, 1H), 7.44 (s, 1H), 6.99 (s, 1H), 4.93-4.81 (m, 1H), 4.26-4.17 (m, 1H), 4.16-4.06 (m, 3H), 3.33-3.28 (m, 1H), 2.99 (d, 1H), 2.36-2.17 (m, 2H), 2.13 (s, 6H), 1.36 (q, 6H). MS obsd. (ESI$^+$) [(M+H)$^+$]: 387.

Example 44

10-Methoxy-6-(2-methoxy-1,1-dimethyl-ethyl)-2-oxo-9-(3-pyrazol-1-ylpropoxy)-6,7-dihydrobenzo[a]quinolizine-3-carboxylic acid

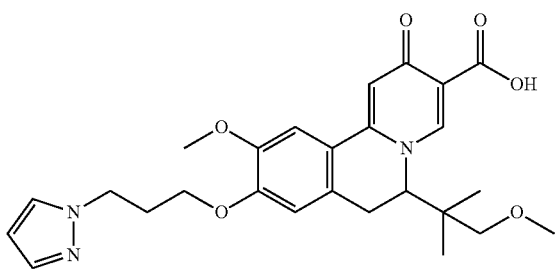 [SMILES: COCC(C)(C)C1Cc2cc(OCCCn3cccn3)c(OC)cc2-c2cc(=O)c(C(=O)O)cn21]

Step 1: Preparation of ethyl 9-(3-bromopropoxy)-10-methoxy-6-(2-methoxy-1,1-dimethyl-ethyl)-2-oxo-6,7-dihydrobenzo[a]quinolizine-3-carboxylate

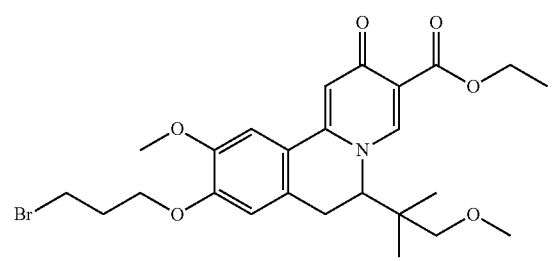 [SMILES: CCOC(=O)c1cn2c(cc1=O)-c1cc(OC)c(OCCCBr)cc1CC2C(C)(C)COC]

To a stirred solution of ethyl 9-hydroxy-10-methoxy-6-(2-methoxy-1,1-dimethyl-ethyl)-2-oxo-6,7-dihydrobenzo[a]quinolizine-3-carboxylate (from step 1 of Example 2, 50 mg, 0.124 mmol) and 1,3-dibromopropane (30 mg, 0.149 mmol) in DMF (2 mL) was added K$_2$CO$_3$ (26 mg, 0.186 mmol). The mixture was stirred at 30° C. for 12 hrs, and then partitioned between EtOAc (30 mL) and H$_2$O (10 mL). The separated organic layer was washed with brine twice, dried over anhydrous Na$_2$SO$_4$ and concentrated under reduced pressure to afford ethyl 9-(3-bromopropoxy)-10-methoxy-6-(2-methoxy-1,1-dimethyl-ethyl)-2-oxo-6,7-dihydrobenzo[a]quinolizine-3-carboxylate (80 mg, crude) as brown oil, which was used directly in the next step without purification.

Step 2: Preparation of ethyl 10-methoxy-6-(2-methoxy-1,1-dimethyl-ethyl)-2-oxo-9-(3-pyrazol-1-ylpropoxy)-6,7-dihydrobenzo[a]quinolizine-3-carboxylate

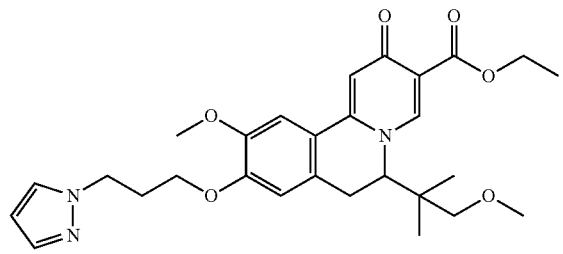 [SMILES: CCOC(=O)c1cn2c(cc1=O)-c1cc(OC)c(OCCCn3cccn3)cc1CC2C(C)(C)COC]

To a stirred solution of ethyl 9-(3-bromopropoxy)-10-methoxy-6-(2-methoxy-1,1-dimethyl-ethyl)-2-oxo-6,7-dihydrobenzo[a]quinolizine-3-carboxylate (80 mg, 0.153 mmol) and pyrazole (21 mg, 0.306 mmol) in DMF (2 mL) was added K$_2$CO$_3$ (42 mg, 0.306 mmol). The mixture was stirred at 30° C. for 12 hrs, and then partitioned between EtOAc (30 mL) and H$_2$O (10 mL). The separated organic layer was washed with brine twice, dried over anhydrous Na$_2$SO$_4$ and concentrated under reduced pressure. The residue was purified by the column chromatography to afford ethyl 10-methoxy-6-(2-methoxy-1,1-dimethyl-ethyl)-2-oxo-9-(3-pyrazol-1-ylpropoxy)-6,7-dihydrobenzo[a]quinolizine-3-carboxylate (50 mg) as a yellow oil.

Step 3: Preparation of 10-methoxy-6-(2-methoxy-1,1-dimethyl-ethyl)-2-oxo-9-(3-pyrazol-1-ylpropoxy)-6,7-dihydrobenzo[a]quinolizine-3-carboxylic acid

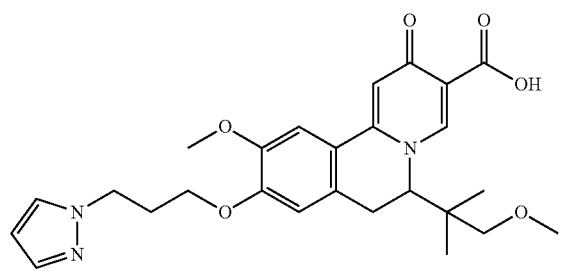 [SMILES: COCC(C)(C)C1Cc2cc(OCCCn3cccn3)c(OC)cc2-c2cc(=O)c(C(=O)O)cn21]

To a solution of ethyl 10-methoxy-6-(2-methoxy-1,1-dimethyl-ethyl)-2-oxo-9-(3-pyrazol-1-ylpropoxy)-6,7-dihydrobenzo[a]quinolizine-3-carboxylate (50 mg, 0.098 mmol) in EtOH (1.0 mL) was added 2 M NaOH aqueous solution (0.15 mL, 0.29 mmol). The mixture was stirred at 20° C. for 12 hrs, and then acidified with 1 M hydrochloric acid (1.0 mL). The resulting mixture was partitioned between EtOAc (60 mL) and H$_2$O (30 mL). The separated organic layer was washed with brine twice, dried over anhydrous Na$_2$SO$_4$ and concentrated under reduced pressure. The residue was purified by prep-HPLC to afford 10-methoxy-6-(2-methoxy-1,1-dimethyl-ethyl)-2-oxo-9-(3-pyrazol-1-ylpropoxy)-6,7-dihydrobenzo[a]quinolizine-3-carboxylic acid (5.3 mg) as a yellow solid. $^1$H NMR (400 MHz, DMSO-d6) δ 8.55 (s, 1H), 7.73 (d, 1H), 7.34-7.55 (m, 3H), 7.01 (s, 1H), 6.24 (m, 1H), 4.63 (m, 1H), 4.29 (m, 2H), 3.95-4.11 (m, 2H), 3.88 (s, 3H), 3.15-3.33 (m, 2H), 3.13 (s, 3H), 2.74-2.98 (m, 2H), 2.26 (m, 2H), 0.86 (s, 3H), 0.45 (s, 3H). MS obsd. (ESI$^+$) [(M+H$^+$)]: 482.

Example 45

9-Ethyl-10-methoxy-6-(2-methoxy-1,1-dimethyl-ethyl)-2-oxo-6,7-dihydrobenzo[a]quinolizine-3-carboxylic acid

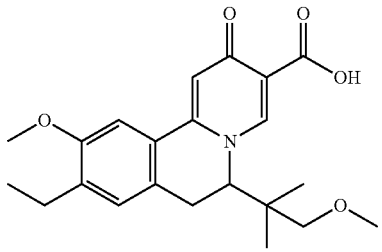

Step 1: Preparation of ethyl 10-methoxy-6-(2-methoxy-1,1-dimethyl-ethyl)-2-oxo-9-(trifluoromethylsulfonyloxy)-6,7-dihydrobenzo[a]quinolizine-3-carboxylate

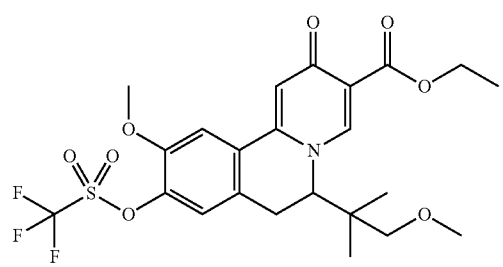 [SMILES: CCOC(=O)c1cn2c(cc1=O)-c1cc(OC)c(OS(=O)(=O)C(F)(F)F)cc1CC2C(C)(C)COC]

To a solution of ethyl 9-hydroxy-10-methoxy-6-(2-methoxy-1,1-dimethyl-ethyl)-2-oxo-6,7-dihydrobenzo[a]quinolizine-3-carboxylate (300 mg, 0.74 mmol) and Et$_3$N (227 mg, 2.24 mmol) in DCM (3 mL) was added a solution of PhN(SO$_2$CF$_3$)$_2$ (400 mg, 1.12 mmol) in DCM (3 mL) drop wise at 0° C. The mixture was allowed to be warmed to 20° C. and stirred at 20° C. for 16 hrs. The mixture was diluted with DCM (30 mL). Then the resulting organic mixture was separated, washed with 1 M hydrochloric acid (10 mL) and brine (10 mL), dried over anhydrous Na$_2$SO$_4$ and concentrated under reduced pressure. The residue was purified by the column chromatography to afford ethyl 10-methoxy-6-(2-methoxy-1,1-dimethyl-ethyl)-2-oxo-9-(trifluoromethylsulfonyloxy)-6,7-dihydrobenzo[a]quinolizine-3-carboxylate (120 mg) as a yellow solid.

Step 2: Preparation of ethyl 9-ethyl-10-methoxy-6-(2-methoxy-1,1-dimethyl-ethyl)-2-oxo-6,7-dihydrobenzo[a]quinolizine-3-carboxylate

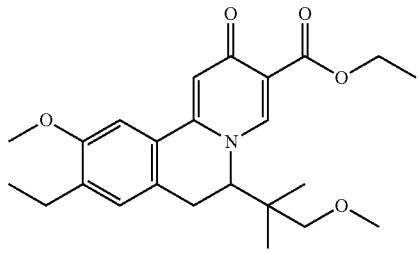 [SMILES: CCOC(=O)c1cn2c(cc1=O)-c1cc(OC)c(CC)cc1CC2C(C)(C)COC]

To a stirred solution of ethyl 10-methoxy-6-(2-methoxy-1,1-dimethyl-ethyl)-2-oxo-9-(trifluoromethylsulfonyloxy)-6,7-dihydrobenzo[a]quinolizine-3-carboxylate (20 mg, 0.037 mmol) and ethylboronic acid (4 mg, 0.056 mmol) in THF (1 mL) and H₂O (0.2 mL) was added Pd(dppf)Cl₂.CH₂Cl₂ (1 mg, 0.002 mmol). The resulting mixture was heated at 60° C. with stirring for 12 hrs under nitrogen atmosphere, and then diluted with EtOAc (30 mL). The resulting mixture was washed with H₂O and brine, dried over anhydrous Na₂SO₄ and concentrated under reduced pressure to afford crude ethyl 9-ethyl-10-methoxy-6-(2-methoxy-1,1-dimethyl-ethyl)-2-oxo-6,7-dihydrobenzo[a]quinolizine-3-carboxylate (30 mg) as a brown oil, which was used in the next step without further purification.

Step 3: Preparation of 9-ethyl-10-methoxy-6-(2-methoxy-1,1-dimethyl-ethyl)-2-oxo-6,7-dihydrobenzo[a]quinolizine-3-carboxylic acid

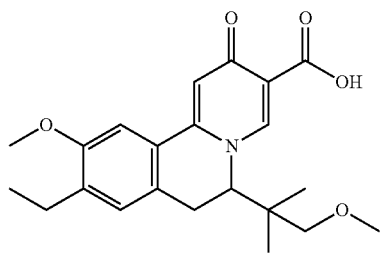

To a solution of ethyl 9-ethyl-10-methoxy-6-(2-methoxy-1,1-dimethyl-ethyl)-2-oxo-6,7-dihydrobenzo[a]quinolizine-3-carboxylate (30 mg, crude) in EtOH (1.0 mL) was added 2 M NaOH aqueous solution (0.11 mL, 0.22 mmol). The mixture was stirred at 20° C. for 12 hrs, and then acidified with 1 M hydrochloric acid (1.0 mL). The resulting mixture was partitioned between EtOAc (60 mL) and H₂O (30 mL). The separated organic layer was washed with brine (30 mL), dried over anhydrous Na₂SO₄ and concentrated under reduced pressure. The residue was purified by prep-HPLC to afford 9-ethyl-10-methoxy-6-(2-methoxy-1,1-dimethyl-ethyl)-2-oxo-6,7-dihydrobenzo[a]quinolizine-3-carboxylic acid (5.3 mg) as a yellow solid. $^1$H NMR (400 MHz, DMSO-d6) δ 8.59 (s, 1H), 7.39-7.59 (m, 2H), 7.22 (s, 1H), 4.65 (br. s., 1H), 3.90 (s, 3H), 3.20 (d, 2H), 3.11 (s, 3H), 2.93 (d, 1H), 2.80 (d, 1H), 2.56-2.69 (m, 2H), 1.15 (m, 3H), 0.86 (s, 3H), 0.43 (s, 3H). MS obsd. (ESI⁺) [(M+H⁺)]: 386.

Example 46

10-Methoxy-6-(2-methoxy-1,1-dimethyl-ethyl)-2-oxo-9-pyrrolidin-1-yl-6,7-dihydrobenzo[a]quinolizine-3-carboxylic acid

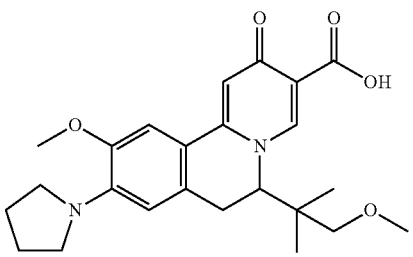 [SMILES: COCC(C)(C)C1Cc2cc(N3CCCC3)c(OC)cc2-c2cc(=O)c(C(=O)O)cn21]

Step 1: Preparation of ethyl 10-methoxy-6-(2-methoxy-1,1-dimethyl-ethyl)-2-oxo-9-pyrrolidin-1-yl-6,7-dihydrobenzo[a]quinolizine-3-carboxylate

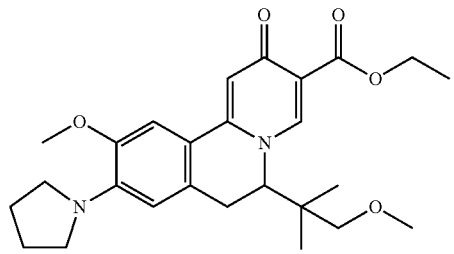 [SMILES: CCOC(=O)c1cn2c(cc1=O)-c1cc(OC)c(N3CCCC3)cc1CC2C(C)(C)COC]

To a solution of ethyl 10-methoxy-6-(2-methoxy-1,1-dimethyl-ethyl)-2-oxo-9-(trifluoromethylsulfonyloxy)-6,7-dihydrobenzo[a]quinolizine-3-carboxylate (70 mg, 0.131 mmol) in NMP (14 mL) was added pyrrolidine (47 mg, 0.656 mmol). The reaction vessel was sealed and heated under microwave at 150° C. for 1 hr. The resulting reaction mixture was partitioned between EtOAc (60 mL) and H₂O (30 mL). The separated organic layer was washed with brine, dried over anhydrous Na₂SO₄ and concentrated under reduced pressure to afford crude ethyl 10-methoxy-6-(2-methoxy-1,1-dimethyl-ethyl)-2-oxo-9-pyrrolidin-1-yl-6,7-dihydrobenzo[a]quinolizine-3-carboxylate (80 mg) as a brown oil, which was used in the next step without purification.

Step 2: Preparation of 10-methoxy-6-(2-methoxy-1,1-dimethyl-ethyl)-2-oxo-9-pyrrolidin-1-yl-6,7-dihydrobenzo[a]quinolizine-3-carboxylic acid

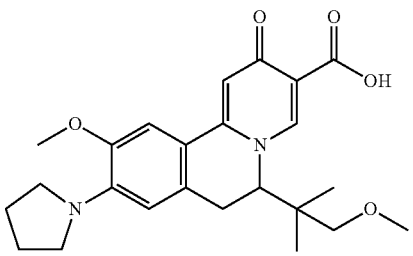 [SMILES: COCC(C)(C)C1Cc2cc(N3CCCC3)c(OC)cc2-c2cc(=O)c(C(=O)O)cn21]

To a solution of ethyl 10-methoxy-6-(2-methoxy-1,1-dimethyl-ethyl)-2-oxo-9-pyrrolidin-1-yl-6,7-dihydrobenzo[a]quinolizine-3-carboxylate (80 mg, crude) in EtOH (1 mL) was added 2 M NaOH aqueous solution (0.26 mL, 0.53 mmol). The mixture was stirred at 20° C. for 12 hrs, and then acidified with 1 M hydrochloric acid (1.0 mL). The mixture was portioned between EtOAc (60 mL) and H₂O (30 mL). The separated organic layer was washed with brine (30 mL), dried over anhydrous Na₂SO₄ and concentrated under reduced pressure. The residue was purified by prep-HPLC to afford 10-methoxy-6-(2-methoxy-1,1-dimethyl-ethyl)-2-oxo-9-pyrrolidin-1-yl-6,7-dihydrobenzo[a]quinolizine-3-carboxylic acid (4.5 mg) as a yellow solid. ¹H NMR (400 MHz, DMSO-d6) δ 8.47 (s, 1H), 7.32 (s, 1H), 7.26 (s, 1H), 6.55 (s, 1H), 4.58 (m, 1H), 3.82 (s, 3H), 3.44 (br. s., 4H), 3.27 (m, 1H), 3.15 (s, 3H), 3.05-3.14 (m, 1H), 2.95 (m, 1H), 2.81 (m, 1H), 1.87 (m., 4H), 0.87 (s, 3H), 0.47 (s, 3H). MS obsd. (ESI⁺) [(M+H⁺)]: 427.

Example 47

9-Cyano-10-methoxy-6-(2-methoxy-1,1-dimethyl-ethyl)-2-oxo-6,7-dihydrobenzo[a]quinolizine-3-carboxylic acid

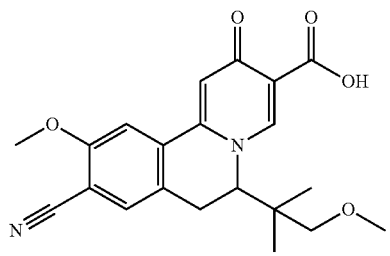

Step 1: Preparation of ethyl 9-formyl-10-methoxy-6-(2-methoxy-1,1-dimethyl-ethyl)-2-oxo-6,7-dihydrobenzo[a]quinolizine-3-carboxylate

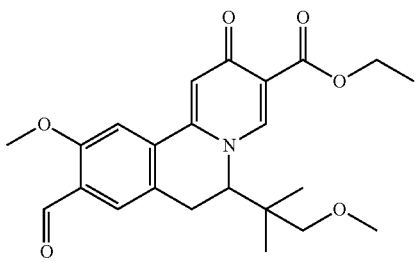 [SMILES: CCOC(=O)c1cn2c(cc1=O)-c1cc(OC)c(C=O)cc1CC2C(C)(C)COC]

To a solution of ethyl 10-methoxy-6-(2-methoxy-1,1-dimethyl-ethyl)-2-oxo-9-(trifluoromethylsulfonyloxy)-6,7-dihydrobenzo[a]quinolizine-3-carboxylate (170 mg, 0.32 mmol) in DMF (5 mL) was added Pd(dppf)Cl₂.CH₂Cl₂ (8 mg, 0.009 mmol), Na₂CO₃ (67 mg, 0.64 mmol) and triethylsilane (74 mg, 0.64 mmol). The mixture was heated at 80° C. with stirring under 60 psi of carbon monoxide for 12 hrs. Then the mixture was cooled to rt and diluted with EtOAc (60 mL). The organic mixture was washed with H₂O and brine, dried over anhydrous Na₂SO₄ and concentrated under reduced pressure. The residue was purified by the column chromatography to afford crude ethyl 9-formyl-10-methoxy-6-(2-methoxy-1,1-dimethyl-ethyl)-2-oxo-6,7-dihydrobenzo[a]quinolizine-3-carboxylate (100 mg) as a black oil.

Step 2: Preparation of ethyl 9-(hydroxyiminomethyl)-10-methoxy-6-(2-methoxy-1,1-dimethyl-ethyl)-2-oxo-6,7-dihydrobenzo[a]quinolizine-3-carboxylate

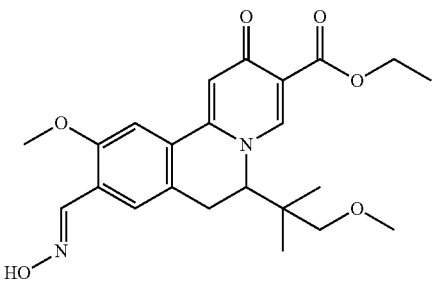 [SMILES: CCOC(=O)c1cn2c(cc1=O)-c1cc(OC)c(/C=N/O)cc1CC2C(C)(C)COC]

To a solution of ethyl 9-formyl-10-methoxy-6-(2-methoxy-1,1-dimethyl-ethyl)-2-oxo-6,7-dihydrobenzo[a]quinolizine-3-carboxylate (100 mg, 0.24 mmol) in MeOH (2 mL) were added hydroxylamine hydrochloride (25 mg, 0.36 mmol) and K₂CO₃ (67 mg, 0.48 mmol). The mixture was stirred at 20° C. for 12 hrs, and then filtered. The filtrate was concentrated under reduced pressure to afford crude ethyl 9-(hydroxyiminomethyl)-10-methoxy-6-(2-methoxy-1,1-dimethyl-ethyl)-2-oxo-6,7-dihydrobenzo[a]quinolizine-3-carboxylate (60 mg) as a yellow solid which was used in the next step without further purification.

Step 3: Preparation of ethyl 9-cyano-10-methoxy-6-(2-methoxy-1,1-dimethyl-ethyl)-2-oxo-6,7-dihydrobenzo[a]quinolizine-3-carboxylate

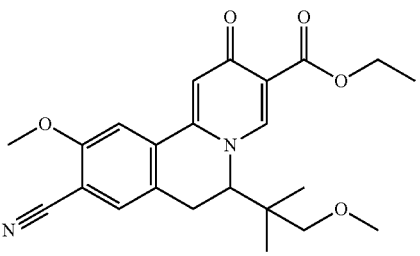 [SMILES: CCOC(=O)c1cn2c(cc1=O)-c1cc(OC)c(C#N)cc1CC2C(C)(C)COC]

To a solution of ethyl 9-(hydroxyiminomethyl)-10-methoxy-6-(2-methoxy-1,1-dimethyl-ethyl)-2-oxo-6,7-dihydrobenzo[a]quinolizine-3-carboxylate (60 mg, 0.14 mmol) in toluene (10 mL) was added acetic anhydride (143 mg, 1.4 mmol). The mixture was heated at 100° C. with stirring for 12 hrs. After being cooled to rt, the mixture was concentrated under reduced pressure and the residue was purified by the column chromatography to afford ethyl 9-cyano-10-methoxy-6-(2-methoxy-1,1-dimethyl-ethyl)-2-oxo-6,7-dihydrobenzo[a]quinolizine-3-carboxylate (50 mg, crude) as a yellow solid.

Step 4: Preparation of 9-cyano-10-methoxy-6-(2-methoxy-1,1-dimethyl-ethyl)-2-oxo-6,7-dihydrobenzo[a]quinolizine-3-carboxylic acid

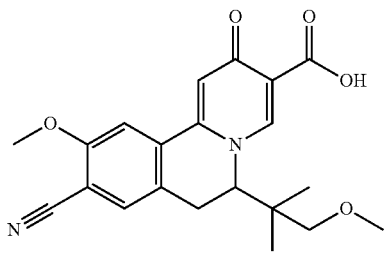

To a solution of ethyl 9-cyano-10-methoxy-6-(2-methoxy-1,1-dimethyl-ethyl)-2-oxo-6,7-dihydrobenzo[a]quinolizine-3-carboxylate (50 mg, 0.12 mmol) in THF (1 mL) was added 3 M LiOH aqueous solution (0.12 mL, 0.36 mmol). The resulting mixture was stirred at 20° C. for 12 hrs, and then concentrated under reduced pressure. The residue was diluted with EtOAc (30 mL) and $H_2O$ (10 mL). To the above mixture was added 1 M hydrochloric acid (3 mL). The organic layer was separated, washed with $H_2O$ and brine, dried over anhydrous $Na_2SO_4$ and concentrated under reduced pressure. The residue was purified by prep-TLC and prep-HPLC to afford 9-cyano-10-methoxy-6-(2-methoxy-1,1-dimethyl-ethyl)-2-oxo-6,7-dihydrobenzo[a]quinolizine-3-carboxylic acid (2 mg) as a light yellow solid. $^1$H NMR (400 MHz, DMSO-d6) δ 8.66 (s, 1H), 7.90 (s, 1H), 7.78 (s, 1H), 7.75 (s, 1H), 4.73 (m, 1H), 4.05 (s, 3H), 3.06 (s, 3H), 2.94 (d, 1H), 2.79 (d, 1H), 0.87 (s, 3H), 0.49 (s, 3H). MS obsd. (ESI$^+$) [(M+H$^+$)]: 383.

BIOLOGICAL EXAMPLES

Example 48

Materials and Methods

HBV Cell Line

HepG2.2.15 cells (Acs et al. *Proc Natl Acad Sci USA*, 84, (1987), 4641-4), a constitutively HBV-expressing cell line were cultured in DMEM+Glutamax-I medium (Invitrogen, Carlsbad, Calif., USA, Catalog number: 11320082), supplemented with 10% fetal bovine serum (Invitrogen, Catalog number: 10099141) and G418 (Invitrogen, Catalog number: 10131027) at a final concentration of 200 mg/L and maintained in 5% $CO_2$ at 37° C.

HBsAg Assay

HepG2.2.15 cells were seeded in duplicate into white, 96-well plates at 1.5×10$^4$ cells/well. The cells were treated with a three-fold serial dilution series of the compounds in DMSO. The final DMSO concentration in all wells was 1% and DMSO was used as no drug control.

The HBsAg chemiluminescence immunoassay (CLIA) kit (Autobio Diagnostics Co., Zhengzhou, China, Catalog number: CL0310-2) was used to measure the levels of secreted HBV antigens semi-quantitatively. For the detection 50 μL/well culture supernatant was used and HBsAg was quantified using HBsAg chemiluminescence immunoassay (CLIA) kit (Autobio Diagnostics Co., Zhengzhou, China, Catalog number: CL0310-2), 50 μl of the supernatant was transferred to the CLIA assay plate and 50 μL of enzyme conjugate reagent was added into each well. The plates were sealed and gently agitated for 1 hour at room temperature. The supernatant-enzyme-mixture was discarded and wells were washed 6 times with 300 μL of PBS. The residual liquid was removed by plating the CLIA plate right side down on absorbent tissue paper. 25 μL of substrates A and B were added to each well. Luminance was measured using a luminometer (Mithras LB 940 Multimode Microplate Reader) after 10 minutes incubation. Dose-response curves were generated and the $IC_{50}$ value was extrapolated by using the E-WorkBook Suite (ID Business Solutions Ltd., Guildford, UK). The $IC_{50}$ was defined as the compound concentration (or conditioned media log dilution) at which HBsAg secretion was reduced by 50% compared to the no drug control.

The compounds of the present invention were tested for their capacity to inhibit HBsAg as described herein. The Examples were tested in the above assay and found to have $IC_{50}$ below 50 μM. Particular compounds of formula I were found to have $IC_{50}$ below 0.10 μM. More Particular compounds of formula I were found to have $IC_{50}$ below 0.010 μM. Results of HBsAg assay are given in Table 1.

TABLE 1

Activity data of particular compounds

| Example No. | $IC_{50}$ (μM) |
|---|---|
| 1 | 0.007 |
| 2 | 0.034 |
| 3 | 0.009 |
| 4 | 0.014 |
| 5 | 0.006 |
| 6 | 0.022 |
| 7 | 0.009 |
| 8 | 0.012 |
| 9 | 0.004 |
| 10 | 0.006 |
| 11 | 0.519 |
| 12 | 0.19 |
| 13 | 0.579 |
| 14 | 0.003 |
| 15 | 0.124 |
| 16 | 0.068 |
| 17 | 0.537 |
| 18 | 0.075 |
| 19 | 0.088 |
| 20 | 0.127 |
| 21 | 0.041 |
| 22 | 4.017 |
| 23 | 0.018 |
| 24 | 0.005 |
| 25 | 0.002 |
| 26 | 0.084 |
| 27 | 0.005 |
| 28 | 0.003 |
| 29 | 0.396 |
| 30 | 0.004 |
| 31 | 0.003 |
| 32 | 8.27 |
| 33 | 0.117 |
| 34 | 3.38 |
| 35 | 0.868 |
| 36 | 0.254 |
| 37 | 1.544 |
| 38 | 33.285 |
| 39 | 19.783 |
| 40 | 7.453 |
| 41 | 4.86 |
| 42 | 0.216 |
| 43 | 0.134 |
| 44 | 0.19 |
| 45 | 0.074 |
| 46 | 0.009 |
| 47 | 0.23 |

HBV DNA Assay

The assay employs real-time qPCR (TaqMan) to directly measure extracellular HBV DNA copy number. HepG2.2.15 cells were plated in 96-well microtiter plates. Only the interior wells were utilized to reduce "edge effects" observed during cell culture, the exterior wells were filled with complete medium to help minimize sample evaporation. On the following day, the HepG2.2.15 cells were washed and the medium was replaced with complete medium containing various concentrations of a test compound in triplicate. 3TC was used as the positive control, while media alone was added to cells as a negative control (virus control, VC). Three days later, the culture medium was replaced with fresh medium containing the appropriately diluted drug. Six days following the initial administration of the test compound, the cell culture supernatant was collected, treated with pronase and then used in a real-time qPCR/TaqMan assay to determine HBV DNA copy numbers. Antiviral activity was calculated from the reduction in HBV DNA levels ($IC_{50}$).

The compounds of the present invention were tested for their capacity to inhibit HBV DNA as described herein. The Examples were tested in the above assay and found to have $IC_{50}$ below 50 μM. Particular compounds of formula I were found to have $IC_{50}$ below 0.10 μM. More Particular compounds of formula I were found to have $IC_{50}$ below 0.010 μM. Results of HBV DNA assay are given in Table 2.

TABLE 2

Anti HBV DNA production activity in HepG2.2.15 cells

| Example No. | $IC_{50}$ (μM) |
|---|---|
| 25 | <0.032 |
| 28 | 0.0005 |

The invention claimed is:
1. A compound of formula (I)

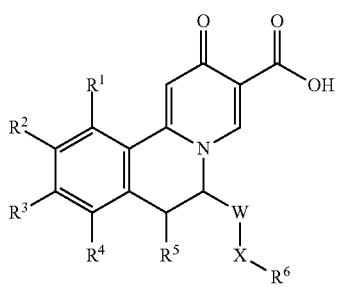

wherein
$R^1$, $R^2$, $R^3$ and $R^4$ are independently selected from the group consisting of hydrogen, halogen, $C_{1-6}$alkyl, di-$C_{1-6}$alkylamino, cyano, N-containing monocyclic heterocycloalkyl and $OR^7$, wherein
$R^7$ is hydrogen; $C_{1-6}$alkyl; or $C_{1-6}$alkyl which is substituted one or more times by fluoro, $C_{3-7}$cycloalkyl, phenyl, hydroxyl, amino, $C_{1-6}$alkoxy, $C_{1-6}$alkylsulfanyl, $C_{1-6}$alkylsulfonyl, di$C_{1-6}$alkylamino, $C_{1-6}$alkoxycarbonylamino, monocyclic heterocycloalkyl, pyrazoyl or imidazolyl;
$R^5$ is hydrogen or $C_{1-6}$alkyl;
$R^6$ is hydrogen, $C_{1-6}$alkyl, phenyl-$C_xH_{2x}$—, $C_{1-6}$alkylcarbonyl, $C_{1-6}$alkylsulfonyl, benzoyl or monocyclic heterocycloalkyl, wherein
x is 1-6;
W is a bond, $C_yH_{2y}C(R^8)(R^9)C_zH_{2z}$ or $C_yH_{2y}CH(R^8)CH(R^9)C_zH_{2z}$, wherein
$R^8$ and $R^9$ are independently selected from the group consisting of hydrogen, fluoro, hydroxy and $C_{1-6}$alkyl,
y is 0-6;
z is 0-6;
X is a bond; O; S; $S(O)_2$; or $NR^{10}$, wherein $R^{10}$ is hydrogen or $C_{1-6}$alkyl;
or $R^6$ and $R^{10}$, together with the nitrogen to which they are attached, form monocyclic heterocycloalkyl;
with the proviso that when X is a bond, $R^6$ is not hydrogen, $C_{1-6}$alkyl or phenyl-$C_xH_{2x}$—;
or a pharmaceutically acceptable salt, enantiomer, or diastereoisomer thereof.

2. The compound according to claim 1, wherein
$R^1$, $R^2$, $R^3$ and $R^4$ are independently selected from the group consisting of hydrogen, fluoro, chloro, methyl, ethyl, methoxy, ethoxy, benzyloxy, trifluoromethylmethoxy, methoxyethoxy, methoxypropoxy, ethoxyethoxy, cyclopropylmethoxy, hydroxypropoxy, hydroxydimethylpropoxy, hydoxyhexoxy, (methylpyrrolidinyl)ethoxy, aminohexoxy, dimethylaminopropoxy, (tert-butoxycarb onylamino)hexoxy, methyl sulfanylpropoxy, methyl sulfonylpropoxy, pyrrolidinylpropoxy, (2-oxo-pyrrolidinyl)propoxy, pyrazoylpropoxy, imidazolylpropoxy, morpholinyl-propoxy, dimethylamino, cyano and pyrrolidinyl;
$R^5$ is hydrogen;
$R^6$ is hydrogen, methyl, benzyl, acetyl, methylsulfonyl, benzoyl, pyrrolidin-1-yl, 2-oxo-pyrrolidinyl or tetrahydropyranyl;
W is a bond, $CH_2$, $C(CH_3)_2$ or $C(CH_3)_2CH_2$;
X is a bond; O; S; $S(O)_2$; or $NR^{10}$, wherein $R^{10}$ is hydrogen or methyl;
or $R^6$ and $R^{10}$, together with the nitrogen to which they are attached, form pyrrolidinyl or 2-oxo-pyrrolidinyl;
or a pharmaceutically acceptable salt, enantiomer or diastereomer thereof.

3. The compound according to claim 1, wherein
$R^1$ is hydrogen;
$R^2$ is halogen or $C_{1-6}$alkoxy;
$R^3$ is cyano, $C_{1-6}$alkyl, pyrrolidinyl or $OR^7$, wherein
$R^7$ is $C_{1-6}$alkyl; or $C_{1-6}$alkyl which is substituted one or more times by fluoro, hydroxy, amino, $C_{3-7}$cycloalkyl, phenyl, $C_{1-6}$alkoxy, $C_{1-6}$alkylsulfanyl, $C_{1-6}$alkylsulfonyl, morpholinyl, 2-oxo-pyrrolidinyl, pyrrolidinyl, di$C_{1-6}$alkylamino, $C_{1-6}$alkoxycarbonylamino, pyrazoyl or $C_{1-6}$alkylpyrrolidinyl;
$R^4$ is hydrogen;
$R^5$ is hydrogen;
$R^6$ is hydrogen, $C_{1-6}$alkyl, phenyl-$C_xH_{2x}$, $C_{1-6}$alkylcarbonyl, $C_{1-6}$alkylsulfonyl, benzoyl or tetrahydropyranyl, wherein
x is 1-6;
W is a bond, $C(R^8)(R^9)C_zH_{2z}$, wherein
$R^8$ and $R^9$ are independently selected from the group consisting of hydrogen and $C_{1-6}$alkyl,
z is 0-6;
X is a bond; O; S; $S(O)_2$; or $NR^{10}$, wherein $R^{10}$ is hydrogen or $C_{1-6}$alkyl;
or $R^6$ and $R^{10}$, together with the nitrogen to which they are attached, form pyrrolidinyl or 2-oxo-pyrrolidinyl;
or a pharmaceutically acceptable salt, enantiomer or diastereomer thereof.

4. The compound according to claim 3, wherein
$R^1$ is hydrogen;
$R^2$ is chloro, methoxy or ethoxy;
$R^3$ is cyano, ethyl, pyrrolidinyl, methoxy, ethoxy, benzyloxy, trifluoromethylmethoxy, methoxyethoxy, methoxypropoxy, ethoxyethoxy, cyclopropylmethoxy, hydroxypropoxy, hydroxy-dimethylpropoxy, hydoxyhexoxy, (methylpyrrolidinyl)ethoxy, aminohexoxy, dimethylaminopropoxy, morpholinylpropoxy, pyrrolidinylpropoxy, (2-oxo-pyrrolidinyl)propoxy, (tert-butoxycarbonylamino)hexoxy, methyl sulfanylpropoxy, methyl sulfonylpropoxy or pyrazoylpropoxy;

$R^4$ is hydrogen;

$R^5$ is hydrogen;

$R^6$ is hydrogen, methyl, benzyl, acetyl, methylsulfonyl, benzoyl or tetrahydropyranyl;

W is a bond, $CH_2$, $C(CH_3)_2$ or $C(CH_3)_2CH_2$;

X is a bond; O; S; $S(O)_2$; or $NR^{10}$, wherein $R^{10}$ is hydrogen or methyl;

or $R^6$ and $R^{10}$, together with the nitrogen to which they are attached, form pyrrolidinyl or 2-oxo-pyrrolidinyl;

or a pharmaceutically acceptable salt, enantiomer or diastereomer thereof.

5. The compound of formula (IA) according to claim 3, wherein

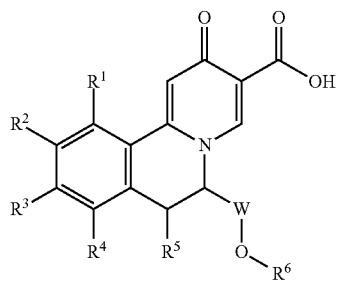

(IA)

$R^1$ is hydrogen;

$R^2$ is halogen or $C_{1-6}$alkoxy;

$R^3$ is cyano, $C_{1-6}$alkyl, pyrrolidinyl or $OR^7$, wherein $R^7$ is $C_{1-6}$alkyl; or $C_{1-6}$alkyl which is substituted one or more times by fluoro, hydroxy, amino, $C_{3-7}$cycloalkyl, phenyl, $C_{1-6}$alkoxy, $C_{1-6}$alkylsulfanyl, $C_{1-6}$alkylsulfonyl, morpholinyl, 2-oxo-pyrrolidinyl, pyrrolidinyl, $diC_{1-6}$alkylamino, $C_{1-6}$alkoxycarbonylamino, $C_{1-6}$alkylpyrrolidinyl or pyrazoyl;

$R^4$ is hydrogen;

$R^5$ is hydrogen;

$R^6$ is hydrogen, $C_{1-6}$alkyl, phenyl-$C_xH_{2x}$ or $C_{1-6}$alkylcarbonyl, wherein x is 1-6;

W is $C(R^8)(R^9)C_zH_{2z}$, wherein $R^8$ and $R^9$ are independently selected from the group consisting of hydrogen and $C_{1-6}$alkyl, z is 0-6;

or a pharmaceutically acceptable salt, enantiomer or diastereomer thereof.

6. The compound according to claim 5, wherein $R^1$ is hydrogen;

$R^2$ is chloro, methoxy or ethoxy;

$R^3$ is cyano, ethyl, pyrrolidinyl, methoxy, ethoxy, benzyloxy, trifluoromethylmethoxy, methoxypropoxy, ethoxyethoxy, cyclopropylmethoxy, hydroxypropoxy, hydroxydimethylpropoxy, hydoxyhexoxy, (methylpyrrolidinyl)ethoxy, aminohexoxy, dimethylaminopropoxy, morpholinylpropoxy, pyrrolidinylpropoxy, (2-oxo-pyrrolidinyl)propoxy, (tert-butoxycarbonylamino)hexoxy, methyl sulfanylpropoxy, methyl sulfonylpropoxy or pyrazoylpropoxy;

$R^4$ is hydrogen;

$R^5$ is hydrogen;

$R^6$ is hydrogen, methyl, benzyl or acetyl;

W is $CH_2$, $C(CH_3)_2$ or $C(CH_3)_2CH_2$;

or a pharmaceutically acceptable salt, enantiomer or diastereomer thereof.

7. The compound according to claim 5, wherein $R^1$ is hydrogen;

$R^2$ is halogen or $C_{1-6}$alkoxy;

$R^3$ is $OR^7$, wherein $R^7$ is $C_{1-6}$alkyl; or $C_{1-6}$alkyl which is substituted one or more times by fluoro, hydroxy, amino, $C_{3-7}$cycloalkyl, phenyl, $C_{1-6}$alkoxy, $C_{1-6}$alkylsulfanyl, morpholinyl or $C_{1-6}$alkoxycarbonylamino;

$R^4$ is hydrogen;

$R^5$ is hydrogen;

$R^6$ is hydrogen or $C_{1-6}$alkyl;

W is $C(R^8)(R^9)C_zH_{2z}$, wherein $R^8$ and $R^9$ are independently selected from the group consisting of hydrogen and $C_{1-6}$alkyl, z is 0-6;

X is O;

or a pharmaceutically acceptable salt, enantiomer or diastereomer thereof.

8. The compound according to claim 7, wherein $R^1$ is hydrogen;

$R^2$ is chloro or methoxy;

$R^3$ is methoxy, benzyloxy, trifluoromethylmethoxy, methoxypropoxy, ethoxyethoxy, cyclopropylmethoxy, hydroxypropoxy, hydroxydimethylpropoxy, aminohexoxy, morpholinylpropoxy, (tert-butoxycarbonylamino)hexoxy or methyl sulfanylpropoxy;

$R^4$ is hydrogen;

$R^5$ is hydrogen;

$R^6$ is hydrogen or methyl;

W is $C(CH_3)_2CH_2$;

X is O;

or a pharmaceutically acceptable salt, enantiomer or diastereomer thereof.

9. The compound according claim 1, wherein $R^2$ is halogen or $C_{1-6}$alkoxy, or a pharmaceutically acceptable salt, enantiomer or diastereomer thereof.

10. The compound according to claim 9, wherein $R^2$ is methoxy or chloro, or a pharmaceutically acceptable salt, enantiomer or diastereomer thereof.

11. The compound according to claim 10, wherein $R^3$ is $C_{1-6}$alkoxy$C_{1-6}$alkoxy, or a pharmaceutically acceptable salt, enantiomer or diastereomer thereof.

12. The compound according to claim 11, wherein $R^3$ is methoxypropoxy, or a pharmaceutically acceptable salt, enantiomer or diastereomer thereof.

13. The compound according to claim 12, wherein $R^6$ is hydrogen or $C_{1-6}$alkyl, or a pharmaceutically acceptable salt, enantiomer or diastereomer thereof.

14. The compound according to claim 13, wherein $R^6$ is methyl, or a pharmaceutically acceptable salt, enantiomer or diastereomer thereof.

15. The compound according to claim 14, wherein W is $C(CH_3)_2CH_2$, or a pharmaceutically acceptable salt, enantiomer or diastereomer thereof.

16. The compound according to claim 1, selected from the group consisting of

9-Benzyloxy-10-methoxy-6-(2-methoxy-1,1-dimethylethyl)-2-oxo-6,7-dihydrobenzo[a]quinolizine-3-carboxylic acid;

9,10-Dimethoxy-6-(2-methoxy-1,1-dimethyl-ethyl)-2-oxo-6,7-dihydrobenzo[a]quinolizine-3-carboxylic acid;

10-Methoxy-6-(2-methoxy-1,1-dimethyl-ethyl)-2-oxo-9-(2,2,2-trifluoroethoxy)-6,7-dihydrobenzo[a]quinolizine-3-carboxylic acid;

10-Methoxy-6-(2-methoxy-1,1-dimethyl-ethyl)-9-(3-morpholinopropoxy)-2-oxo-6,7-dihydrobenzo[a]quinolizine-3-carboxylic acid;

9-(6-Hydroxyhexoxy)-10-methoxy-6-(2-methoxy-1,1-dimethyl-ethyl)-2-oxo-6,7-dihydrobenzo[a]quinolizine-3-carboxylic acid;

9-(3-Hydroxypropoxy)-10-methoxy-6-(2-methoxy-1,1-dimethyl-ethyl)-2-oxo-6,7-dihydrobenzo[a]quinolizine-3-carboxylic acid;

9-(3-Hydroxy-2,2-dimethyl-propoxy)-10-methoxy-6-(2-methoxy-1,1-dimethyl-ethyl)-2-oxo-6,7-dihydrobenzo[a]quinolizine-3-carboxylic acid;

9-(2-Ethoxyethoxy)-10-methoxy-6-(2-methoxy-1,1-dimethyl-ethyl)-2-oxo-6,7-dihydrobenzo[a]quinolizine-3-carboxylic acid;

9-(Cyclopropylmethoxy)-10-methoxy-6-(2-methoxy-1,1-dimethyl-ethyl)-2-oxo-6,7-dihydrobenzo[a]quinolizine-3-carboxylic acid;

10-Methoxy-6-(2-methoxy-1,1-dimethyl-ethyl)-9-(3-methylsulfanylpropoxy)-2-oxo-6,7-dihydrobenzo[a]quinolizine-3-carboxylic acid;

10-Methoxy-6-(2-methoxy-1,1-dimethyl-ethyl)-2-oxo-9-(3-pyrrolidin-1-ylpropoxy)-6,7-dihydrobenzo[a]quinolizine-3-carboxylic acid;

10-Methoxy-6-(2-methoxy-1,1-dimethyl-ethyl)-2-oxo-9-[3-(2-oxopyrrolidin-1-yl)propoxy]-6,7-dihydrobenzo[a]quinolizine-3-carboxylic acid;

9-[3-(Dimethylamino)propoxy]-10-methoxy-6-(2-methoxy-1,1-dimethyl-ethyl)-2-oxo-6,7-dihydrobenzo[a]quinolizine-3-carboxylic acid;

9-[6-(tert-Butoxycarb onylamino)hexoxy]-10-methoxy-6-(2-methoxy-1,1-dimethyl-ethyl)-2-oxo-6,7-dihydrobenzo[a]quinolizine-3-carb oxylic acid;

10-Methoxy-6-(2-methoxy-1,1-dimethyl-ethyl)-9-(3-methylsulfonylpropoxy)-2-oxo-6,7-dihydrobenzo[a]quinolizine-3-carboxylic acid;

9-(6-Aminohexoxy)-10-methoxy-6-(2-methoxy-1,1-dimethyl-ethyl)-2-oxo-6,7-dihydrobenzo[a]quinolizine-3-carboxylic acid;

10-Methoxy-6-(2-methoxy-1,1-dimethyl-ethyl)-9-[2-(1-methylpyrrolidin-2-yl)ethoxy]-2-oxo-6,7-dihydrobenzo[a]quinolizine-3-carboxylic acid;

10-Methoxy-6-(methoxymethyl)-9-(3-methoxypropoxy)-2-oxo-6,7-dihydrobenzo[a]quinolizine-3-carboxylic acid;

6-(1-Hydroxy-1-methyl-ethyl)-10-methoxy-9-(3-methoxypropoxy)-2-oxo-6,7-dihydrobenzo[a]quinolizine-3-carboxylic acid;

(+)-6-(1-Hydroxy-1-methyl-ethyl)-10-methoxy-9-(3-methoxypropoxy)-2-oxo-6,7-dihydrobenzo[a]quinolizine-3-carboxylic acid;

(−)-6-(1-Hydroxy-1-methyl-ethyl)-10-methoxy-9-(3-methoxypropoxy)-2-oxo-6,7-dihydrobenzo[a]quinolizine-3-carboxylic acid;

6-(2-Benzyloxy-1,1-dimethyl-ethyl)-10-methoxy-9-(3-methoxypropoxy)-2-oxo-6,7-dihydrobenzo[a]quinolizine-3-carboxylic acid;

6-(2-Hydroxy-1,1-dimethyl-ethyl)-10-methoxy-9-(3-methoxypropoxy)-2-oxo-6,7-dihydrobenzo[a]quinolizine-3-carboxylic acid;

(+)-6-(2-Hydroxy-1,1-dimethyl-ethyl)-10-methoxy-9-(3-methoxypropoxy)-2-oxo-6,7-dihydrobenzo[a]quinolizine-3-carboxylic acid;

(−)-6-(2-Hydroxy-1,1-dimethyl-ethyl)-10-methoxy-9-(3-methoxypropoxy)-2-oxo-6,7-dihydrobenzo[a]quinolizine-3-carboxylic acid;

10-Methoxy-6-(2-methoxy-1,1-dimethyl-ethyl)-9-(3-methoxypropoxy)-2-oxo-6,7-dihydrobenzo[a]quinolizine-3-carboxylic acid;

(+)-10-Methoxy-6-(2-methoxy-1,1-dimethyl-ethyl)-9-(3-methoxypropoxy)-2-oxo-6,7-dihydrobenzo[a]quinolizine-3-carboxylic acid;

(−)-10-Methoxy-6-(2-methoxy-1,1-dimethyl-ethyl)-9-(3-methoxypropoxy)-2-oxo-6,7-dihydrobenzo[a]quinolizine-3-carboxylic acid;

10-Chloro-6-(2-methoxy-1,1-dimethyl-ethyl)-9-(3-methoxypropoxy)-2-oxo-6,7-dihydrobenzo[a]quinolizine-3-carboxylic acid;

(+)-10-Chloro-6-(2-methoxy-1,1-dimethyl-ethyl)-9-(3-methoxypropoxy)-2-oxo-6,7-dihydrobenzo[a]quinolizine-3-carboxylic acid;

(−)-10-Chloro-6-(2-methoxy-1,1-dimethyl-ethyl)-9-(3-methoxypropoxy)-2-oxo-6,7-dihydrobenzo[a]quinolizine-3-carboxylic acid;

9,10-Diethoxy-6-(hydroxymethyl)-2-oxo-6,7-dihydrobenzo[a]quinolizine-3-carboxylic acid;

6-(Acetoxymethyl)-9,10-diethoxy-2-oxo-6,7-dihydrobenzo[a]quinolizine-3-carboxylic acid;

10-Methoxy-6-(2-methoxy-1,1-dimethyl-ethyl)-2-oxo-9-(3-pyrazol-1-ylpropoxy)-6,7-dihydrobenzo[a]quinolizine-3-carboxylic acid;

9-Ethyl-10-methoxy-6-(2-methoxy-1,1-dimethyl-ethyl)-2-oxo-6,7-dihydrobenzo[a]quinolizine-3-carb oxylic acid;

10-Methoxy-6-(2-methoxy-1,1-dimethyl-ethyl)-2-oxo-9-pyrrolidin-1-yl-6,7-dihydrobenzo[a]quinolizine-3-carboxylic acid; and 9-Cyano-10-methoxy-6-(2-methoxy-1,1-dimethyl-ethyl)-2-oxo-6,7-dihydrobenzo[a]quinolizine-3-carboxylic acid;

or a pharmaceutically acceptable salt, enantiomer or diastereomer thereof.

17. The compound according to claim 1, selected from the group consisting of 9-Benzyloxy-10-methoxy-6-(2-methoxy-1,1-dimethyl-ethyl)-2-oxo-6,7-dihydrobenzo[a]quinolizine-3-carboxylic acid;

9,10-Dimethoxy-6-(2-methoxy-1,1-dimethyl-ethyl)-2-oxo-6,7-dihydrobenzo[a]quinolizine-3-carboxylic acid;

10-Methoxy-6-(2-methoxy-1,1-dimethyl-ethyl)-2-oxo-9-(2,2,2-trifluoroethoxy)-6,7-dihydrobenzo[a]quinolizine-3-carboxylic acid;

10-Methoxy-6-(2-methoxy-1,1-dimethyl-ethyl)-9-(3-morpholinopropoxy)-2-oxo-6,7-dihydrobenzo[a]quinolizine-3-carboxylic acid;

9-(3-Hydroxypropoxy)-10-methoxy-6-(2-methoxy-1,1-dimethyl-ethyl)-2-oxo-6,7-dihydrobenzo[a]quinolizine-3-carboxylic acid;

9-(3-Hydroxy-2,2-dimethyl-propoxy)-10-methoxy-6-(2-methoxy-1,1-dimethyl-ethyl)-2-oxo-6,7-dihydrobenzo[a]quinolizine-3-carboxylic acid;

9-(2-Ethoxyethoxy)-10-methoxy-6-(2-methoxy-1,1-dimethyl-ethyl)-2-oxo-6,7-dihydrobenzo[a]quinolizine-3-carboxylic acid;

9-(Cyclopropylmethoxy)-10-methoxy-6-(2-methoxy-1,1-dimethyl-ethyl)-2-oxo-6,7-dihydrobenzo[a]quinolizine-3-carboxylic acid;

10-Methoxy-6-(2-methoxy-1,1-dimethyl-ethyl)-9-(3-methylsulfanylpropoxy)-2-oxo-6,7-dihydrobenzo[a]quinolizine-3-carboxylic acid;

9-[6-(tert-Butoxycarbonylamino)hexoxy]-10-methoxy-6-(2-methoxy-1,1-dimethyl-ethyl)-2-oxo-6,7-dihydrobenzo[a]quinolizine-3-carboxylic acid;

9-(6-Aminohexoxy)-10-methoxy-6-(2-methoxy-1,1-dimethyl-ethyl)-2-oxo-6,7-dihydrobenzo[a]quinolizine-3-carboxylic acid;

6-(2-Hydroxy-1,1-dimethyl-ethyl)-10-methoxy-9-(3-methoxypropoxy)-2-oxo-6,7-dihydrobenzo[a]quinolizine-3-carboxylic acid;

(+)-6-(2-Hydroxy-1,1-dimethyl-ethyl)-10-methoxy-9-(3-methoxypropoxy)-2-oxo-6,7-dihydrobenzo[a]quinolizine-3-carboxylic acid;

10-Methoxy-6-(2-methoxy-1,1-dimethyl-ethyl)-9-(3-methoxypropoxy)-2-oxo-6,7-dihydrobenzo[a]quinolizine-3-carboxylic acid;

(+)-10-Methoxy-6-(2-methoxy-1,1-dimethyl-ethyl)-9-(3-methoxypropoxy)-2-oxo-6,7-dihydrobenzo[a]quinolizine-3-carboxylic acid;

10-Chloro-6-(2-methoxy-1,1-dimethyl-ethyl)-9-(3-methoxypropoxy)-2-oxo-6,7-dihydrobenzo[a]quinolizine-3-carboxylic acid; and (+)-10-Chloro-6-(2-methoxy-1,1-dimethyl-ethyl)-9-(3-methoxypropoxy)-2-oxo-6,7-dihydrobenzo[a]quinolizine-3-carboxylic acid;

or a pharmaceutically acceptable salt, enantiomer or diastereomer thereof.

18. The compound according to claim 3, wherein
$R^1$ is hydrogen;
$R^2$ is halogen or $C_{1-6}$alkoxy;
$R^3$ is $C_{1-6}$alkoxy or $C_{1-6}$alkoxy$C_{1-6}$alkoxy;
$R^4$ is hydrogen;
$R^5$ is hydrogen;
$R^6$ is hydrogen, $C_{1-6}$alkyl, $C_{1-6}$alkylcarbonyl, $C_{1-6}$alkylsulfonyl, benzoyl or tetrahydropyranyl;
W is a bond, $C(R^8)(R^9)C_zH_{2z}$, wherein
$R^8$ and $R^9$ are independently selected from the group consisting of hydrogen and $C_{1-6}$alkyl,
z is 0-6;
X is a bond; S; $S(O)_2$; or $NR^{10}$, wherein $R^{10}$ is hydrogen or $C_{1-6}$alkyl;
or $R^6$ and $R^{10}$, together with the nitrogen to which they are attached, form pyrrolidinyl or 2-oxo-pyrrolidinyl;
or a pharmaceutically acceptable salt, enantiomer or diastereomer thereof.

19. The compound according to claim 18; wherein
$R^1$ is hydrogen;
$R^2$ is chloro or ethoxy;
$R^3$ is ethoxy, methoxyethoxy or methoxypropoxy;
$R^4$ is hydrogen;
$R^5$ is hydrogen;
$R^6$ is hydrogen, methyl, acetyl, methylsulfonyl, benzoyl or tetrahydropyranyl;
W is a bond or $CH_2$;
X is a bond; S; $S(O)_2$; or $R^{10}$, wherein $R^{10}$ is hydrogen or methyl;
or $R^6$ and $R^{10}$, together with the nitrogen to which they are attached, form pyrrolidinyl or 2-oxo-pyrrolidinyl;
or a pharmaceutically acceptable salt, enantiomer or diastereomer thereof.

20. The compound according to claim 1, selected from the group consisting of
10-Chloro-9-(3-methoxypropoxy)-2-oxo-6-tetrahydropyran-4-yl-6,7-dihydrobenzo[a]quinolizine-3-carboxylic acid;

10-Chloro-9-(2-methoxyethoxy)-6-(methylsulfanylmethyl)-2-oxo-6,7-dihydrobenzo[a]quinolizine-3-carboxylic acid;

10-Chloro-9-(2-methoxyethoxy)-6-(methylsulfonylmethyl)-2-oxo-6,7-dihydrobenzo[a]quinolizine-3-carboxylic acid;

6-(Aminomethyl)-9,10-diethoxy-2-oxo-6,7-dihydrobenzo[a]quinolizine-3-carboxylic acid;

9,10-Diethoxy-6-(methanesulfonamidomethyl)-2-oxo-6,7-dihydrobenzo[a]quinolizine-3-carboxylic acid;

6-(Benzamidomethyl)-9,10-diethoxy-2-oxo-6,7-dihydrobenzo[a]quinolizine-3-carboxylic acid;

9,10-Diethoxy-2-oxo-6-[(2-oxopyrrolidin-1-yl)methyl]-6,7-dihydrobenzo[a]quinolizine-3-carboxylic acid;

6-[[Acetyl(methyl)amino]methyl]-9,10-diethoxy-2-oxo-6,7-dihydrobenzo[a]quinolizine-3-carboxylic acid;

9,10-Diethoxy-2-oxo-6-(pyrrolidin-1-ylmethyl)-6,7-dihydrobenzo[a]quinolizine-3-carboxylic acid; and 6-[(Dimethylamino)methyl]-9,10-diethoxy-2-oxo-6,7-dihydrobenzo[a]quinolizine-3-carboxylic acid;

or a pharmaceutically acceptable salt, enantiomer or diastereomer thereof.

21. A pharmaceutical composition comprising a compound according to claim 1, or a pharmaceutically acceptable salt, enantiomer or diastereomer thereof, and a therapeutically inert carrier.

22. A compound which is 9-(2-Ethoxyethoxy)-10-methoxy-6-(2-methoxy-1,1-dimethyl-ethyl)-2-oxo-6,7-dihydrobenzo[a]quinolizine-3-carboxylic acid or a pharmaceutically acceptable salt thereof.

23. A compound which is 10-Methoxy-6-(2-methoxy-1,1-dimethyl-ethyl)-9-(3-methoxypropoxy)-2-oxo-6,7-dihydrobenzo[a]quinolizine-3-carboxylic acid or a pharmaceutically acceptable salt thereof.

24. A compound which is (+)-10-Methoxy-6-(2-methoxy-1,1-dimethyl-ethyl)-9-(3-methoxypropoxy)-2-oxo-6,7-dihydrobenzo[a]quinolizine-3-carboxylic acid or a pharmaceutically acceptable salt thereof.

25. A compound which is (−)-10-Methoxy-6-(2-methoxy-1,1-dimethyl-ethyl)-9-(3-methoxypropoxy)-2-oxo-6,7-dihydrobenzo[a]quinolizine-3-carboxylic acid or a pharmaceutically acceptable salt thereof.

* * * * *